(12) United States Patent
Yerkes et al.

(10) Patent No.: US 8,912,120 B2
(45) Date of Patent: Dec. 16, 2014

(54) HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND SYNTHETIC AUXIN HERBICIDES

(71) Applicants: Carla N. Yerkes, Crawfordsville, IN (US); Richard K. Mann, Franklin, IN (US); Norbert M. Satchivi, Westfield, IN (US); Paul R. Schmitzer, Indianapolis, IN (US)

(72) Inventors: Carla N. Yerkes, Crawfordsville, IN (US); Richard K. Mann, Franklin, IN (US); Norbert M. Satchivi, Westfield, IN (US); Paul R. Schmitzer, Indianapolis, IN (US)

(73) Assignee: Dow AgroSciences, LLC., Indianapolis, IN (US)

(*) Notice: Subject to any disclaimer, the term of this patent is extended or adjusted under 35 U.S.C. 154(b) by 0 days.

(21) Appl. No.: 13/833,923

(22) Filed: Mar. 15, 2013

(65) Prior Publication Data
US 2014/0031214 A1 Jan. 30, 2014

Related U.S. Application Data

(60) Provisional application No. 61/675,070, filed on Jul. 24, 2012.

(51) Int. Cl.
A01N 25/26 (2006.01)
A01N 43/40 (2006.01)
A01N 43/60 (2006.01)
A01N 43/42 (2006.01)
A01N 43/54 (2006.01)
A01N 37/10 (2006.01)
A01N 37/38 (2006.01)

(52) U.S. Cl.
CPC .............. A01N 43/40 (2013.01); A01N 43/42 (2013.01); A01N 43/54 (2013.01); A01N 37/10 (2013.01); A01N 37/38 (2013.01)
USPC ........................... 504/100; 504/130; 504/136

(58) Field of Classification Search
None
See application file for complete search history.

(56) References Cited

U.S. PATENT DOCUMENTS

| 7,314,849 | B2 | 1/2008 | Balko et al. | |
|---|---|---|---|---|
| 7,622,641 | B2 | 11/2009 | McCutchen et al. | |
| 2009/0062121 | A1 | 3/2009 | Satchivi et al. | |
| 2010/0137137 | A1 | 6/2010 | Rosinger et al. | |
| 2011/0082162 | A1 | 4/2011 | Lorsbach et al. | |
| 2011/0207607 | A1 | 8/2011 | Satchivi et al. | |
| 2012/0115727 | A1 | 5/2012 | Satchivi et al. | |
| 2012/0190551 | A1 | 7/2012 | Yerkes et al. | |
| 2013/0109569 | A1* | 5/2013 | Dave et al. | 504/130 |
| 2013/0310256 | A1 | 11/2013 | Yerkes et al. | |
| 2014/0031210 | A1 | 1/2014 | Yerkes et al. | |
| 2014/0031211 | A1 | 1/2014 | Yerkes et al. | |
| 2014/0031212 | A1 | 1/2014 | Yerkes et al. | |
| 2014/0031213 | A1 | 1/2014 | Yerkes et al. | |
| 2014/0031215 | A1 | 1/2014 | Yerkes et al. | |
| 2014/0031216 | A1 | 1/2014 | Yerkes et al. | |
| 2014/0031217 | A1 | 1/2014 | Yerkes et al. | |
| 2014/0031218 | A1 | 1/2014 | Mann et al. | |
| 2014/0031219 | A1 | 1/2014 | Yerkes et al. | |
| 2014/0031220 | A1 | 1/2014 | Yerkes et al. | |
| 2014/0031221 | A1 | 1/2014 | Yerkes et al. | |
| 2014/0031222 | A1 | 1/2014 | Yerkes et al. | |
| 2014/0031227 | A1 | 1/2014 | Yerkes et al. | |
| 2014/0031228 | A1 | 1/2014 | Mann et al. | |
| 2014/0031229 | A1 | 1/2014 | Mann et al. | |

FOREIGN PATENT DOCUMENTS

WO   WO 2007/082098   7/2007

OTHER PUBLICATIONS

Thomas, S., Written Opinion of the International Search Authority for PCT/US2013/051313, Dec. 6, 2013, pp. 1-5, ISA/US.

(Continued)

Primary Examiner — Alton Pryor
(74) Attorney, Agent, or Firm — Michael R. Asam; Faegre Baker Daniels LLP.

(57) ABSTRACT

Provided herein are herbicidal compositions containing and methods for controlling undesirable vegetation utilizing (a) a compound of formula (I):

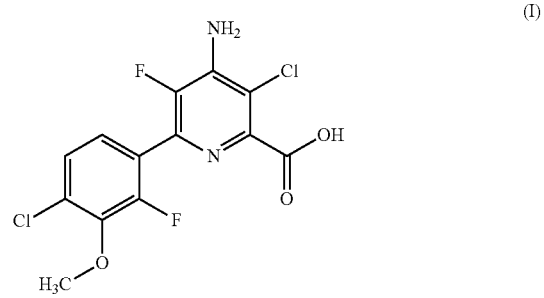

or an agriculturally acceptable salt or ester thereof and (b) a synthetic auxin herbicide, e.g., 2,4-D, aminocyclopyrachlor, aminopyralid, clomeprop-P, clopyralid, dicamba, diclorprop-P, fluoroxypyr methylheptyl ester (MHE), MCPA, picloram, quinclorac, triclopyr, and halauxifen-methyl(methyl 4-amino-3-chloro-6-(4-chloro-2-fluoro-3-methoxyphenyl) picolinate), or an agriculturally acceptable salt or ester thereof. The compositions and methods provided herein provide control of undesirable vegetation, e.g., in direct-seeded, water-seeded and transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) or rights-of-way (ROW).

26 Claims, No Drawings

(56) References Cited

OTHER PUBLICATIONS

Thomas, S., International Search Report for PCT/US2013/051313, Dec. 6, 2013, pp. 1-4, ISA/US.

Synthesis of Esters: Esterification Reactions, obtained via google.com in U.S. Appl. No. 13/840,306, obtained online Mar. 8, 2014.

Chui, M.P., Non-Final Office Action in U.S. Appl. No. 13/840,306, Mar. 13, 2014, pp. 1-12, USPTO.

Pryor, A.N., Notice of Allowance and Fee(s) Due for U.S. Appl. No. 13/832,978, Apr. 9, 2014, pp. 1-13, USPTO.

Pryor, A.N., Notice of Allowance and Fee(s) Due for U.S. Appl. No. 13/833,315, May 12, 2014, pp. 1-8, USPTO.

Pryor, A.N., Notice of Allowance and Fee(s) Due for U.S. Appl. No. 13/833,315, Mar. 20, 2014, pp. 1-11, USPTO.

Pryor, A.N., Notice of Allowance and Fee(s) Due for U.S. Appl. No. 13/833,362, May 29, 2014, pp. 1-8, USPTO.

Pryor, A.N., Notice of Allowance and Fee(s) Due for U.S. Appl. No. 13/833,372, May 14, 2014, pp. 1-8, USPTO.

Pryor, A.N., Notice of Allowance and Fee(s) Due for U.S. Appl. No. 13/833,659, Mar. 17, 2014, pp. 1-12, USPTO.

Pryor, A.N., Notice of Allowance and Fee(s) Due for U.S. Appl. No. 13/840,488, May 2, 2014, pp. 1-8, USPTO.

Pryor, A.N., Notice of Allowance and Fee(s) Due for U.S. Appl. No. 13/833,965, Apr. 1, 2014, pp. 1-8, USPTO.

Pryor, A.N., Notice of Allowance and Fee(s) Due for U.S. Appl. No. 13/834,326, May 13, 2014, pp. 1-4, USPTO.

Pryor, A.N., Notice of Allowance and Fee(s) Due for U.S. Appl. No. 13/834,326, Apr. 2, 2014, pp. 1-9, USPTO.

Pryor, A.N., Notice of Allowance and Fee(s) Due for U.S. Appl. No. 13/836,653, Apr. 2, 2014, pp. 1-8, USPTO.

Pryor, A.N., Notice of Allowance and Fee(s) Due for U.S. Appl. No. 13/836,653, Jun. 17, 2014, pp. 1-5, USPTO.

Pryor, A.N., Notice of Allowance and Fee(s) Due for U.S. Appl. No. 13/837,990, Apr. 1, 2014, pp. 1-8, USPTO.

Pryor, A.N., Notice of Allowance and Fee(s) Due for U.S. Appl. No. 13/839,043, May 27, 2014, pp. 1-5, USPTO.

Pryor, A.N., Notice of Allowance and Fee(s) Due for U.S. Appl. No. 13/839,043, Mar. 24, 2014, pp. 1-8, USPTO.

Pryor, A.N., Notice of Allowance and Fee(s) Due for U.S. Appl. No. 13/840,303, Apr. 25, 2014, pp. 1-8, USPTO.

Pryor, A.N., Notice of Allowance and Fee(s) Due for U.S. Appl. No. 13/834,706, Mar. 12, 2014, pp. 1-13, USPTO.

Pryor, A.N., Notice of Allowance and Fee(s) Due for U.S. Appl. No. 13/840,346, Jun. 4, 2014, pp. 1-8, USPTO.

Pryor, A.N., Notice of Allowance and Fee(s) Due for U.S. Appl. No. 13/840,419, May 5, 2014, pp. 1-8, USPTO.

Pryor, A.N., Notice of Allowance and Fee(s) Due for U.S. Appl. No. 13/840,236, Apr. 25, 2014, pp. 1-8, USPTO.

* cited by examiner

HERBICIDAL COMPOSITIONS COMPRISING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND SYNTHETIC AUXIN HERBICIDES

PRIORITY CLAIM

This application claims the benefit of U.S. provisional patent application No. 61/675,070 filed on Jul. 24, 2012, this provisional application is incorporated herein by reference in its entirety.

FIELD

Provided herein are herbicidal compositions comprising (a) 4-amino-3-chloro-5-fluoro-6-(4-chloro-2-fluoro-3-methoxyphenyl)pyridine-2-carboxylic acid or an agriculturally acceptable ester or salt thereof and (b) synthetic auxin herbicides.

Provided herein are also methods of controlling undesirable vegetation comprising applying (a) 4-amino-3-chloro-5-fluoro-6-(4-chloro-2-fluoro-3-methoxyphenyl)pyridine-2-carboxylic acid or an agriculturally acceptable ester or salt thereof and (b) a synthetic auxin herbicide or an agriculturally acceptable salt or ester thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for compositions and methods that are effective in controlling undesirable vegetation.

SUMMARY

A first embodiment of the invention provided herein includes herbicidal compositions comprising an herbicidally effective amount of (a) a compound of the formula (I)

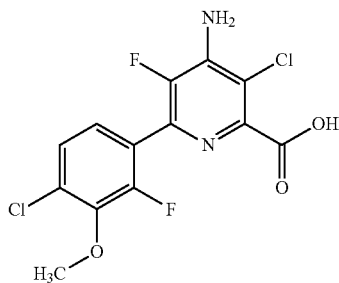

(I)

or an agriculturally acceptable salt or ester thereof, and (b) a synthetic auxin herbicide.

A second embodiment includes the mixture of the first embodiment in which formula (I), is present in at least one of the following forms: a carboxylic acid, a carboxylate salt, an aralkyl, an alkyl ester, an unsubstituted benzyl, a substituted benzyl, a $C_{1-4}$ alkyl, and/or an n-butyl ester.

A third embodiment includes the mixture according to either the first or second embodiments wherein the (b) at least one synthetic auxin herbicide is at least one compound selected from the group consisting of: 2,4-D, 2,4-D EHE, 2,4-DMA, 2,4-D choline, aminocyclopyrachlor, aminopyralid, aminopyralid TIPA, clomeprop-P, clopyralid, clopyralid MEA, dicamba, dicamba DMA, diclorprop-P, fluoroxypyr, fluoroxypyr MHE, MCPA, MCPA EHE, mecoprop-P, picloram, picloram $K^+$ salt, quinclorac, triclopyr, triclopyr TEA, triclopyr choline, triclopyr BEE, halauxifen-methyl, halauxifen-methyl(methyl 4-amino-3-chloro-6-(4-chloro-2-fluoro-3-methoxyphenyl)picolinate) or its carboxylate potassium salt, or an agriculturally acceptable salt, ester, or carboxylate salt thereof of at least one of the aforementioned synthetic auxin herbicide.

A fourth embodiment includes the mixtures according to any of the first, second, or third embodiments in which the synthetic auxin herbicide in the mixture is 2,4-D, 2,4-D EHE, 2,4-DMA, or 2,4-D choline wherein the weight ratio of the compound of formula (I) to 2,4-D, 2,4-D EHE, 2,4-DMA, or 2,4-D choline given in units of gae/ha to gai/ha or gae/ha to gae/ha is selected from the group of ranges of ratios and ratios consisting of 1:2, 1:3.5, 1:4, 1:6, 1:7, 1:8, 1:11, 1:12, 1:14, 1:16, 1:17, 1:23, 1:24, 1:28, 1:32, 1:45, 1:48, 1:55, 1:56, 1:64, 1:96, 1:110, from 1:16 to 1:64, from 1:3.5 to 1:28, from 1:8 to 1:64, from 1:2, to 1:16, from 1:11 to 1:45, from 1:6 to 1:96, from 1:4 to 1:64, from 1:4 to 1:32, from 1:7 to 1:55, from 1:7 to 1:28, from 1:14 to 1:110, from 1:28 to 1:56, from 1:2 to 1:110, or within any range defined between any pair of the foregoing values.

A fifth embodiment includes the mixtures according to any of the first, second, or third embodiments in which the synthetic auxin herbicide in the mixture is aminocyclopyrachlor wherein the weight ratio of the compound of formula (I) to aminocyclopyrachlor given in units of gae/ha to gai/ha or gae/ha to gae/ha is selected from the group of ranges of ratios and ratios consisting of: 1:1, 1:2, 1:4, from 1:1 to 1:4, or within any range defined between any pair of the foregoing values.

A sixth embodiment includes the mixtures according to any of the first, second, or third embodiments in which the synthetic auxin herbicide in the mixture is aminopyralid or aminopyralid TIPA wherein the weight ratio of the compound of formula (I) to aminopyralid or aminopyralid TIPA given in units of gae/ha to gai/ha or gae/ha to gae/ha is selected from the group of ranges of ratios and ratios consisting of: 1:1, 1:2, 1:4, 1:8, 3:1, from 1:1 to 1:8, or within any range defined between any pair of the foregoing values.

A seventh embodiment includes the mixtures according to any of the first, second, or third embodiments in which the synthetic auxin herbicide in the mixture is clomeprop-P having a weight ratio of the compound of formula (I) or salt or ester thereof to clomeprop-P or salt or ester thereof is within the range of from 1:159 to about 1:1 or about 1:200 to about 6:1.

An eighth embodiment includes the mixtures according to any of the first, second, or third embodiments in which the synthetic auxin herbicide in the mixture is clopyralid or clopyralid MEA wherein the weight ratio of the compound of formula (I) to clopyralid or clopyralid MEA given in units of gae/ha to gai/ha or gae/ha to gae/ha is selected from the group of ranges of ratios and ratios consisting of: 1:4, 1:5.7, 1:8, 1:16, from 1:4 to 1:16, or within any range defined between any pair of the foregoing values.

A ninth embodiment includes the mixtures according to any of the first, second, or third embodiments in which the synthetic auxin herbicide in the mixture is dicamba or dicamba DMA wherein the weight ratio of the compound of formula (I) to dicamba or dicamba DMA given in units of gae/ha to gai/ha or gae/ha to gae/ha is selected from the group of ranges of ratios and ratios consisting of: 1:3.3, 1:4, 1:6.6, 1:8, 1:11, 1:16, 1:26, 1:45, 1:53, 1:64, from 1:26 to 1:53, from 1:8 to 1:64, from 1:3.3 to 1:26, from 1:11 to 1:45, from 1:3.3 to 1:64, or within any range defined between any pair of the foregoing values.

A tenth embodiment includes the mixtures according to any of the first, second, or third embodiments in which the synthetic auxin herbicide in the mixture is diclorprop-P wherein the weight ratio of the compound of formula (I) to diclorprop-P given in units of gae/ha to gai/ha or gae/ha to gae/ha is selected from the group of ranges of ratios and ratios consisting of: 1:16.

An eleventh embodiment includes the mixtures according to any of the first, second, or third embodiments in which the synthetic auxin herbicide in the mixture is fluoroxypyr or fluoroxypyr MHE wherein the weight ratio of the compound of formula (I) to fluoroxypyr or fluoroxypyr MHE given in units of gae/ha to gai/ha or gae/ha to gae/ha is selected from the group of ranges of ratios and ratios consisting of: 1:2, 1:3.6, 1:4, 1:8, 1:9, 1:14, 1:16, 1:18, 1:32, 1:35, from 1:2 to 1:32, from 1:2 to 1:16, from 1:4 to 1:35, from 1:36 to 1:64, from 1:8 to 1:32, from 1:4.4 to 1:64, from 1:2 to 1:35, or within any range defined between any pair of the foregoing values.

A twelfth embodiment includes the mixtures according to any of the first, second, or third embodiments in which the synthetic auxin herbicide in the mixture is MCPA or MCPA EHE wherein the weight ratio of the compound of formula (I) to MCPA or MCPA EHE given in units of gae/ha to gai/ha or gae/ha to gae/ha is selected from the group of ranges of ratios and ratios consisting of: 1:2, 1:2.2, 1:4, 1:4.4, 1:6.6, 1:8, 1:8.8, 1:11, 1:16, 1:17.5, 1:32, 1:35, from 1:2 to 1:16, from 1:5.7 to 1:32, from 1:8 to 1:32, from 1:2.2 to 1:35, from 1:2 to 1:35, or within any range defined between any pair of the foregoing values.

A thirteenth embodiment includes the mixtures according to any of the first, second, or third embodiments in which the synthetic auxin herbicide in the mixture is mecoprop-P wherein the weight ratio of the compound of formula (I) to mecoprop-P given in units of gae/ha to gai/ha or gae/ha to gae/ha is selected from the group of ranges of ratios and ratios consisting of: 1:23.

A fourteenth embodiment includes the mixtures according to any of the first, second, or third embodiments in which the synthetic auxin herbicide in the mixture is picloram or picloram K$^+$ salt wherein the weight ratio of the compound of formula (I) to picloram or picloram K$^+$ salt given in units of gae/ha to gai/ha or gae/ha to gae/ha is selected from the group of ranges of ratios and ratios consisting of: 1:1.1, 1:2, 1:4, 1:8, 1:16, from 1:2 to 1:16, from 1:1.1 to 1:16, or within any range defined between any pair of the foregoing values.

A fifteenth embodiment includes the mixtures according to any of the first, second, or third embodiments in which the synthetic auxin herbicide in the mixture is quinclorac wherein the weight ratio of the compound of formula (I) to quinclorac given in units of gae/ha to gai/ha or gae/ha to gae/ha is selected from the group of ranges of ratios and ratios consisting of: 1:1.7, 1:2, 1:3, 1:4, 1:7, 1:13, 1:16, 1:18, 1:26, 1:32, 1:35, 1:64, 1:70, 1:128, from 1:9 to 1:70, from 1:3 to 1:128, from 1:16 to 1:64, from 1:7 to 1:13, from 1:7 to 1:64, from 1:8 to 1:64, from 1:4 to 1:16, from 1:2 to 1:128, from 1:1.7 to 1:32, from 1:1.7 to 1:16, or within any range defined between any pair of the foregoing values.

A sixteenth embodiment includes the mixtures according to any of the first, second, or third embodiments in which the synthetic auxin herbicide in the mixture is triclopyr, triclopyr TEA, triclopyr choline or triclopyr BEE wherein the weight ratio of the compound of formula (I) to triclopyr, triclopyr TEA, triclopyr choline or triclopyr BEE given in units of gae/ha to gai/ha or gae/ha to gae/ha is selected from the group of ranges of ratios and ratios consisting of: 1:1.7, 1:2, 1:3.3, 1:4, 1:5, 1:5.6, 1:6.6, 1:8, 1:11, 1:13, 1:14, 1:16, 1:22, 1:17.5, 1:22, 1:26, 1:32, 1:45, from 1:5 to 1:45, from 1:11 to 1:45, from 1:2 to 1:16, from 1:2 to 1:32, from 1:4 to 1:32, from 1:1.7 to 1:26, from 1:1.7 to 1:13, from 1:7 to 1:45, or within any range defined between any pair of the foregoing values.

A seventeenth embodiment includes the mixtures according to any of the first, second, or third embodiments in which the synthetic auxin herbicide in the mixture is halauxifen-methyl(methyl 4-amino-3-chloro-6-(4-chloro-2-fluoro-3-methoxyphenyl)picolinate) or its carboxylate potassium salt wherein the weight ratio of the compound of formula (I) to halauxifen-methyl(methyl 4-amino-3-chloro-6-(4-chloro-2-fluoro-3-methoxyphenyl)picolinate) or its carboxylate potassium salt given in units of gae/ha to gai/ha or gae/ha to gae/ha is selected from the group of ranges of ratios and ratios consisting of: 1:4, 1:2, 1.2:1, 1:1, 2:1, 2.4:1, 4:1, 5:1, 8:1, 10:1 from 1:2 to 4:1, from 1:1 to 8:1, from 1.2:1 to 10:1, from 1:4 to 4:1, from 1:4 to 10:1, or within any range defined between any pair of the foregoing values.

An eighteenth embodiment includes any composition according to any of the first through the seventeenth embodiments wherein the mixture further comprises at least one an agriculturally acceptable agent selected from the group consisting of an adjuvant, a carrier, or a safener.

A nineteenth embodiment includes methods of controlling undesirable vegetation comprising the step of applying or otherwise contacting vegetation and/or soil, and/or water with a herbicidally effective amount of at least one mixture according to any of the first through the eighteenth embodiments.

A twentieth embodiment includes methods according to the nineteenth embodiment wherein undesirable vegetation is controlled according to at least technique selected from the group consisting of: direct-seeded, water-seeded, and/or transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM), or rights-of-way (ROW).

A twenty-first embodiment includes methods according to either of the nineteenth and twentieth embodiments wherein a herbicidally effective amount of the mixture is applied either pre- or post emergently to at least one of the following: a crop, a field, a ROW, or a paddy.

A twenty-second embodiment includes methods according to any of the nineteenth through the twentieth-first embodiments wherein the undesirable vegetation controlled by an application of a herbicidally effective amount of the mixture and at least one of the following phytotoxic actives: glyphosate-, 5-enolpyruvylshikimate-3-phosphate (EPSP) synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase (ACCase) inhibitor-, imidazolinone-, sulfonylurea-, pyrimidinylthiobenzoate-, triazolopyrimidine-, sulfonylaminocarbonyltriazolinone-, acetolactate synthase (ALS) or acetohydroxy acid synthase (AHAS) iinhibitor-, 4-hydroxyphenyl-pyruvate dioxygenase (HPPD) inhibitor-, phytoene desaturase inhibitor-, carotenoid biosynthesis inhibitor-, protoporphyrinogen oxidase (PPO) inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, protoporphyrinogen oxidase (PPO) inhibitor-, triazine-, or bromoxynil-tolerant crops.

A twenty-third embodiment includes a at least one method according to any of the nineteenth through twenty-second embodiments wherein a plant that is tolerant to at least one herbicide is treated, and where the tolerant crop possesses multiple or stacked traits conferring tolerance to multiple herbicides or inhibitors of multiple modes of action, in some embodiments the treated plant that expresses resistance to a herbicide is a itself undesirable vegetation.

A twenty-fourth embodiment includes methods according to the twenty-third embodiment, wherein the resistant or tolerant weed is a biotype with resistance or tolerance to multiple herbicides, multiple chemical classes, inhibitors of multiple herbicide modes-of-action, or via multiple resistance mechanisms.

A twenty-fifth embodiment includes at least one of the methods according to either the twenty-third or twenty-fourth embodiments, wherein the resistant or tolerant undesirable plant is a biotype resistant or tolerant to at least on agent selected from the groups consisting of: acetolactate synthase (ALS) inhibitors or acetohydroxy acid synthase (AHAS), photosystem II inhibitors, acetyl CoA carboxylase (ACCase) inhibitors, synthetic auxins, auxin transport inhibitors, photosystem I inhibitors, 5-enolpyruvylshikimate-3-phosphate (EPSP) synthase inhibitors, microtubule assembly inhibitors, fatty acid and lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

A twenty-sixth embodiment includes methods of controlling undesirable vegetation comprising the step of applying a herbicidally effective amount of at least one mixture according to the fourth embodiment wherein the amount of the mixture is applied at a rate, expressed in gai/ha or gae/ha of 2,4-D, 2,4-D EHE, 2,4-DMA, or 2,4-D choline selected from the group of rates and ranges of rates consisting of, about: 35, 50, 52.5, 70, 105, 140, 150, 210, 240, 280, 420, 480, from 70 to 280, from 105 to 420, from 52.5 to 105, from 240 to 480, from 35 to 70, from 35 to 480, or within any range defined between any pair of the foregoing values.

A twenty-seventh embodiment includes methods according to either of the fourth and twenty-sixth embodiments wherein the controlled plant is at least one plant selected from the group consisting of: ECHCG, DIGSA, ECHCO, CYPES, CYPIR, BRAPP, LEFCH, ECHOR, CYPRO, SCPJU, SCPMA, PANDI, ELEIN, CENMA, PANMI, POLCO, SINAR, SONAR, CASOB, still other embodiments include controlling plants from the genera consisting of: *Echinochloa, Digitaria, Cyperus, Brachiaria, Urochloa, Leptochloa, Schoenop, Schoenoplactus, Panicum, Polygonum, Sinapis, Sonchus*, and *Cassia*

A twenty-eighth embodiment includes methods of controlling undesirable vegetation comprising the step of applying a herbicidally effective amount of at least one a mixture according to the fifth embodiment wherein the amount of the mixture is applied at a rate, expressed in gai/ha or gae/ha of aminocyclopyrachlor selected from the group of rates and ranges of rates consisting of, about: 8.75, 17.5, from 8.75 to 17.5, or within any range defined between any pair of the foregoing values.

A twenty-ninth embodiment includes methods according to either of the fifth and twenty-eighth embodiments wherein the controlled plant is at least one plant selected from the group consisting of: TRFRE, SINAR, CENMA, still other embodiments include controlling plants from the genera consisting of: *Trifolium, Sinapis*, and *Centaurea*.

A thirtieth embodiment includes methods of controlling undesirable vegetation comprising the step of applying a herbicidally effective amount of at least one a mixture according to the sixth embodiment wherein the amount of the mixture is applied at a rate, expressed in gai/ha or gae/ha of aminopyralid or aminopyralid TIPA selected from the group of rates and ranges of rates consisting of, about: 3, 17.5, 35, from 17.5 to 35, or within any range defined between any pair of the foregoing values.

A thirty-first embodiment includes methods according to either of the sixth and thirtieth embodiments wherein the controlled plant is at least one plant selected from the group consisting of: POLCO, CIRAR, BRSNN, TRFRE, SINAR, SOOSS, still other embodiments include controlling plants from the genera consisting of: *Polygonum, Cirsium, Brassica, Trifolium, Sinapis*, and *Solidago*.

A thirty-second embodiment includes methods of controlling undesirable vegetation comprising the step of applying a herbicidally effective amount of at least one a mixture according to the seventh embodiment wherein the amount of the mixture is applied at a rate, expressed in gai/ha or gae/ha of clomeprop-P selected from the group of rates and ranges of rates consisting of, about: 50 gae/ha to about 400 gae/ha, or within any range defined between any pair of the foregoing values.

A thirty-third embodiment includes methods according to either of the seventh and thirty-second embodiments wherein the controlled plant is at least one plant selected from the group consisting of, AMARE, CIRAR, or SOOSS, still other embodiments include controlling plants from the genera consisting of: *Amaranthus, Cirsium*, and *Solidago*.

A thirty-fourth embodiment includes methods of controlling undesirable vegetation comprising the step of applying a herbicidally effective amount of at least one mixture according to the eighth embodiment wherein the amount of the mixture is applied at a rate, expressed in gai/ha or gae/ha of clopyralid or clopyralid MEA selected from the group of rates and ranges of rates consisting of, about 35, 50, from 35 to 50, or within any range defined between any pair of the foregoing values.

A thirty-fifth embodiment includes methods according to either of the eighth and thirty-fourth embodiments wherein the controlled plant is at least one plant selected from the group consisting of: AMARE, CIRAR, SOOS, still other embodiments include controlling plants from the genera consisting of: *Amaranthus, Cirsium*, and *Solidago*.

A thirty-sixth embodiment includes methods of controlling undesirable vegetation comprising the step of applying a herbicidally effective amount of at least one a mixture according to the ninth embodiment wherein the amount of the mixture is applied at a rate, expressed in gai/ha or gae/ha of dicamba or dicamba DMA selected from the group of rates and ranges of rates consisting of, about: 35, 50, 70, 140, 280, from 140 to 280, from 35 to 280, or within any range defined between any pair of the foregoing values.

A thirty-seventh embodiment includes methods according to either of the ninth and thirty-sixth embodiments wherein the controlled plant is at least one plant selected from the group consisting of: AMARE, POLCO, BRSNN, LEFCH, CYPIR, ECHCO, ECHCG, ECHOR, SCPMA, SIDSP, SINAR, CASOB, still other embodiments include controlling plants from the genera consisting of: *Amaranthus, Polygonum, Brassica, Leptochloa, Cyperus, Echinochloa, Schoenoplectus, Bolboschoenus, Sida, Sinapis*, and *Cassia*.

A thirty-eighth embodiment includes methods of controlling undesirable vegetation comprising the step of applying a herbicidally effective amount of at least one a mixture according to the tenth embodiment wherein the amount of the mixture is applied at a rate, expressed in gai/ha or gae/ha of diclorprop-P selected from the group of rates and ranges of rates consisting of, about 140, or within any range defined between any pair of the foregoing values.

A thirty-ninth embodiment includes methods according to either of the tenth and thirty-eighth embodiments wherein the controlled plant is at least one plant selected from the group consisting of: VIOTR, BRSNN, still other embodiments include controlling plants from the genera consisting of: *Viola*, and *Brassica*.

A fortieth embodiment includes methods of controlling undesirable vegetation comprising the step of applying a herbicidally effective amount of at least one a mixture according to the eleventh embodiment wherein the amount of the mixture is applied at a rate, expressed in gai/ha or gae/ha of fluoroxypyr or fluoroxypyr MHE selected from the group of rates and ranges of rates consisting of, about: 35, 70, 140, 149, 280, from 70 to 280, from 35 to 280, or within any range defined between any pair of the foregoing values.

A forty-first embodiment includes methods according to either of the eleventh and fortieth embodiments wherein the controlled plant is at least one plant selected from the group consisting of, CENMA, SONAR, TRFRE, SOOSS, ECHCG, ECHCO, CYPDI, LEFCH, ECHOR, SCPJU, AMARE, SCPMA, VIOTR, POLCO, CIRAR, still other embodiments include controlling plants from the genera consisting of: *Centaurea, Sonchus, Trifolium, Solidago, Echinochloa, Cyperus, Leptochloa, Schoenoplectus, Viola, Polygonum*, and *Cirsium*.

A forty-second embodiment includes methods of controlling undesirable vegetation comprising the step of applying a herbicidally effective amount of at least one a mixture according to the twelfth embodiment wherein the amount of the mixture is applied at a rate, expressed in gai/ha or gae/ha of MCPA or MCPA EHE selected from the group of rates and ranges of rates consisting of, about: 50, 70, 140, 280, from 50 to 140, from 70 to 140, from 50 to 280, from 70 to 280, or within any range defined between any pair of the foregoing values.

A forty-third embodiment includes methods according to either of the twelfth and forty-second embodiments wherein the controlled plant is at least one plant selected from the group consisting of, BRAPP, DIGSA, ECHCG, ECHOR, LEFCH, SCPJU, still other embodiments include controlling plants from the genera consisting of: *Brachiaria, Digitaria, Echinochloa, Leptochloa*, and *Schoenoplectus*.

A forty-fourth embodiment includes methods of controlling undesirable vegetation comprising the step of applying a herbicidally effective amount of at least one mixture according to the thirteenth embodiment wherein the amount of the mixture is applied at a rate, expressed in gai/ha or gae/ha of mecoprop-P selected from the group of rates and ranges of rates consisting of, about: 200 or within any range defined between any pair of the foregoing values.

A forty-fifth embodiment includes methods according to either of the thirteenth and forty-fourth embodiments wherein the controlled plant is at least one plant selected from the group consisting of: BRSNN, still other embodiments include controlling plants from the genera consisting of: *Brassica*.

A forty-sixth embodiment includes methods of controlling undesirable vegetation comprising the step of applying a herbicidally effective amount of at least one a mixture according to the fourteenth embodiment wherein the amount of the mixture is applied at a rate, expressed in gai/ha or gae/ha of picloram or picloram $K^+$ salt selected from the group of rates and ranges of rates consisting of, about: 10, 35, 70, from 35 to 70, or within any range defined between any pair of the foregoing values.

A forty-seventh embodiment includes methods according to either of the fourteenth and forty-sixth embodiments wherein the controlled plant is at least one plant selected from the group consisting of: VIOTR, STEME, POLCO, CENMA, SINAR, still other embodiments include controlling plants from the genera consisting of: *Viola, Stellaria, Polygonum, Centaurea*, and *Sinapis*.

A forty-eighth embodiment includes methods of controlling undesirable vegetation comprising the step of applying a herbicidally effective amount of at least one a mixture according to the fifteenth embodiment wherein the amount of the mixture is applied at a rate, expressed in gai/ha or gae/ha of quinclorac selected from the group of rates and ranges of rates consisting of, about: 70, 140, 280, 560, from 70 to 280, from 70 to 560, or within any range defined between any pair of the foregoing values.

A forty-ninth embodiment includes methods according to either of the fifteenth and forty-eighth embodiments wherein the controlled plant is at least one plant selected from the group consisting of: AMARE, VIOTR, ECHOR, SCPMA, POLCO, CYPES, DIGSA, CYPIR, ECHCG, ISCRU, still other embodiments include controlling plants from the genera consisting of: *Amaranthus, Viola, Echinochloa, Schoenoplectus, Bolboschoenus, Polygonum, Cyperus, Digitaria*, and *Ischaemum*.

A fiftieth embodiment includes methods of controlling undesirable vegetation comprising the step of applying a herbicidally effective amount of at least one a mixture according to the sixteenth embodiment wherein the amount of the mixture is applied at a rate, expressed in gai/ha or gae/ha of triclopyr, triclopyr TEA, triclopyr choline or triclopyr BEE selected from the group of rates and ranges of rates consisting of, about: 35, 50, 70, 98.3, 140, 196.6, 280, from 35 to 140, from 98.3 to 280, from 70 to 280 from 70 to 140, from 35 to 280, or within any range defined between any pair of the foregoing values.

A fifty-first embodiment includes methods according to either of the sixteenth and forty-ninth embodiments wherein the controlled plant is at least one plant selected from the group consisting of, BRAPP, SCPJU, DIGSA, ECHOR, ECHCG, SCPMA, ECHCO, LEFCH, CENMA, SONAR, CIRAR, CASOB, still other embodiments include controlling plants from the genera consisting of: *Brachiaria, Schoenoplectus, Digitaria, Echinochloa, Bolboschoenus, Leptochloa, Centaurea, Sonchus, Cirsium*, and *Cassia*.

A fifty-second embodiment includes methods of controlling undesirable vegetation comprising the step of applying a herbicidally effective amount of at least one a mixture according to the seventeenth embodiment wherein the amount of the mixture is applied at a rate, expressed in gai/ha or gae/ha of halauxifen-methyl(methyl 4-amino-3-chloro-6-(4-chloro-2-fluoro-3-methoxyphenyl)picolinate) or its carboxylate potassium salt selected from the group of rates and ranges of rates consisting of, about: 2.19, 3.75, 4.38, 7.5, 8.75, 15, from 2.19 to 4.38, from 4.38 to 8.75, from 3.75 to 15, from 2.19 to 15, or within any range defined between any pair of the foregoing values.

A fifty-third embodiment includes methods according to either of the seventeenth and fifty-second embodiments wherein the controlled plant is at least one plant selected from the group consisting of, LEFCH, IPOHE, CYPIR, ECHCG, ECHOR, CYPRO, SORHA, ELEIN, still other embodiments include controlling plants from the genera consisting of: *Leptochloa, Ipomoea, Cyperus, Echinochloa, Sorghum, Eleusine.*

Provided herein are herbicidal compositions comprising a herbicidally effective amount of (a) a compound of the formula (I)

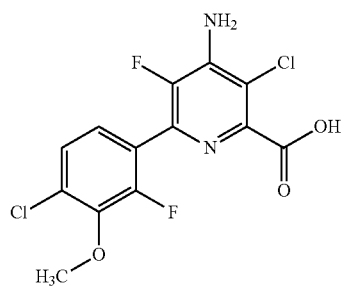

(I)

or an agriculturally acceptable salt or ester of thereof, and (b) a synthetic auxin herbicide. The compositions may also contain an agriculturally acceptable adjuvant or carrier.

Provided herein are also methods of controlling undesirable vegetation comprising applying (a) a compound of formula (I) or an agriculturally acceptable ester or salt thereof and (b) a synthetic auxin herbicide or an agriculturally acceptable salt or ester thereof.

DETAILED DESCRIPTION

Definitions

As used herein, the compound of formula (I) has the following structure:

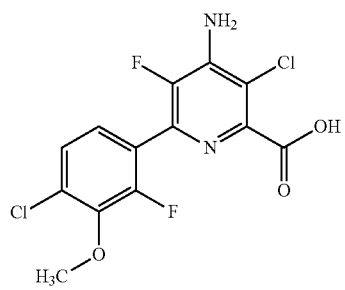

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

Without being limited to any theory, synthetic auxin herbicides are a class of herbicides that generally mimic auxin, a plant growth hormone. They are often called growth regulators because they upset the natural hormone balance in the plant. Exemplary synthetic auxin herbicides include, but are not limited to, 2,4-D, 2,4-DB, aminocyclopyrachlor, aminopyralid, clomeprop-P, clopyralid, dicamba, diclorprop-P, fluoroxypyr methylheptyl ester (MHE), MCPA, mecoprop-P, picloram, quinclorac, triclopyr, and halauxifen-methyl(methyl 4-amino-3-chloro-6-(4-chloro-2-fluoro-3-methoxyphenyl)picolinate), or an agriculturally acceptable salt or ester thereof.

As used herein, 2,4-D is 2-(2,4-dichlorophenoxy)acetic acid and possesses the following structure:

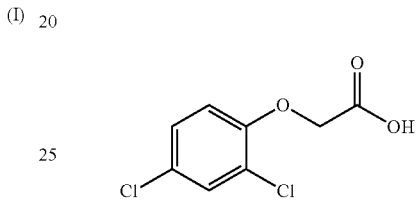

Exemplary uses of 2,4-D are described in Tomlin, C., ed. A World Compendium The Pesticide Manual. 15$^{th}$ ed. Alton: BCPC Publications, 2009 (hereafter "*The Pesticide Manual*, Fifteenth Edition, 2009."). Exemplary uses of 2,4-D include its use for post-emergence control of annual and perennial broadleaf weeds, e.g., in cereals, maize, sorghum, grassland, established turf, grass seed crops, orchards, cranberries, asparagus, sugar cane, rice forestry and non-crop land. Exemplary chemical forms of 2,4-D include salt or ester forms, for example, 2,4-D EHE, which is 2-ethylhexyl 2-(2,4-dichlorophenoxy)acetate and possesses the following structure:

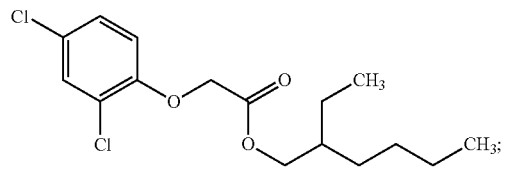 [SMILES: CCCCC(CC)COC(=O)COc1ccc(Cl)cc1Cl]

2,4-D DMA, which is 2-(2,4-dichlorophenoxy)acetic acid with N-methylmethanamine and possesses the following structure:

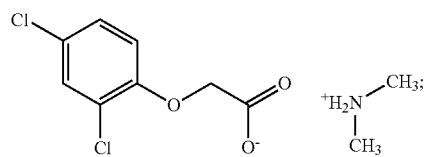

2,4-D choline, which is 2-hydroxy-N,N,N-trimethylethanaminium 2-(2,4-dichlorophenoxy)acetate and possesses the following structure:

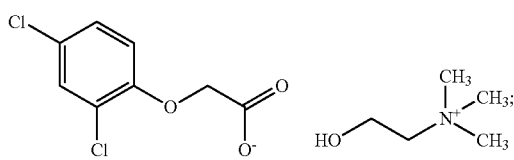

and 2,4-DB, which is 2-(2,4-dichlorophenoxy)butyric acid and possesses the following structure:

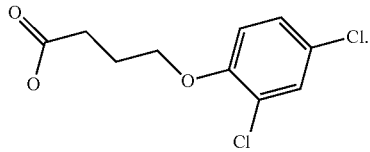 [SMILES: O=C(O)CCCOc1ccc(Cl)cc1Cl]

As used herein, aminocyclopyrachlor is 6-amino-5-chloro-2-cyclopropyl-4-pyrimidinecarboxylic acid and possesses the following structure:

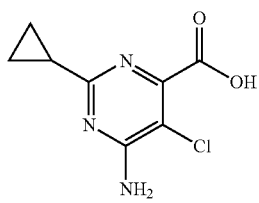 [SMILES: Nc1nc(C2CC2)nc(C(=O)O)c1Cl]

Exemplary uses of aminocyclopyrachlor are described in *The Pesticide Manual*, Fifteenth Edition, 2009. Exemplary uses of aminocyclopyrachlor include its use for control of broadleaf weeds and woody species, e.g., in rights of way, industrial sites, rangeland, permanent grass pastures and natural areas.

As used herein, aminopyralid is 4-amino-3,6-dichloro-2-pyridinecarboxylic acid and possesses the following structure:

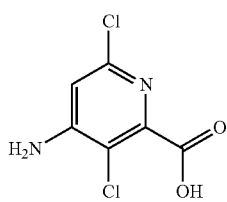

Exemplary uses of aminopyralid are described in *The Pesticide Manual*, Fifteenth Edition, 2009. Exemplary uses of aminopyralid include its use for long-term control of annual and perennial broadleaf weeds, e.g., in range and pasture. Exemplary chemical forms of aminopyralid include, for example, aminopyralid TIPA, which is 4-amino-3,6-dichloropyridine-2-carboxylic acid compound with 1,1',1''-nitrilotris[2-propanol] and possesses the following structure:

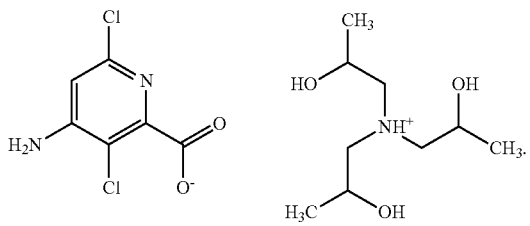

As used herein, clomeprop-P is 2-(2,4-dichloro-3-methylphenoxy)-N-phenylpropanamide and possesses the following structure:

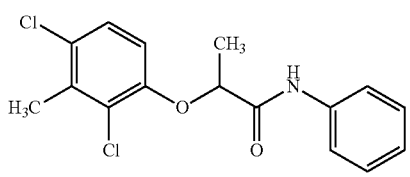 [SMILES: Cc1c(Cl)ccc(OC(C)C(=O)Nc2ccccc2)c1Cl]

Exemplary uses of clomeprop-P are described in *The Pesticide Manual*, Fifteenth Edition, 2009. Exemplary uses of clomeprop include its use for pre- or early post-emergence control of broadleaf and cyperaceous weeds, e.g., in paddy rice.

As used herein, clopyralid is 3,6-dichloro-2-pyridinecarboxylic acid and possesses the following structure:

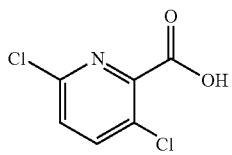 [SMILES: O=C(O)c1nc(Cl)ccc1Cl]

Exemplary uses of clopyralid are described in *The Pesticide Manual*, Fifteenth Edition, 2009. Exemplary uses of clopyralid include its use for post-emergence control of many annual and perennial broadleaf weeds, e.g., in sugar beet, fodder beet, oilseed rape, maize, cereals, brassicas, onions, leeks, strawberries and flax, and in grassland and non-crop land. Exemplary chemical forms of clopyralid include, for example, clopyralid MEA, which is 3,6-dichloro-2-pyridinecarboxylic acid with 2-aminoethanol and possesses the following structure:

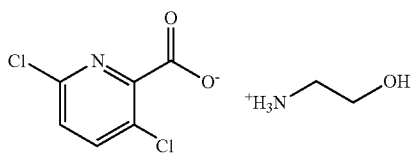

As used herein, dicamba is 3,6-dichloro-2-methoxybenzoic acid and possesses the following structure:

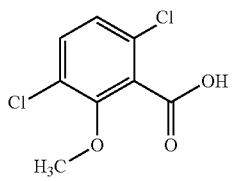

Exemplary uses of dicamba are described in *The Pesticide Manual*, Fifteenth Edition, 2009. Exemplary uses of dicamba include its use for control of annual and perennial broadleaf weeds and brush species, e.g., in cereals, maize, sorghum, sugar cane, asparagus, perennial seed grasses, turf, pastures, rangeland and non-crop land. Exemplary chemical forms of dicambe include, for example, dicamba DMA, which is 3,6-dichloro-2-methoxybenzoic acid compound with N-methyl-methanamine and possesses the following structure:

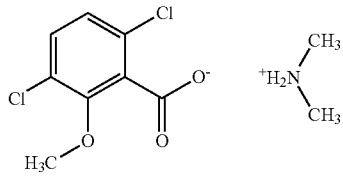

As use herein, dichlorprop-P is (2R)-2-(2,4-dichlorophenoxy)propanoic acid and possesses the following structure:

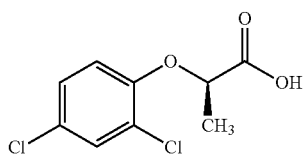

Exemplary uses of dichlorprop-P is described in *The Pesticide Manual*, Fifteenth Edition, 2009. Exemplary uses of dichlorprop-P include its use for post-emergence control of broadleaf weeds, e.g., in cereals.

As used herein, fluoroxypyr is 2-[(4-amino-3,5-dichloro-6-fluoro-2-pyridinyl)oxy]acetic acid and possesses the following structure:

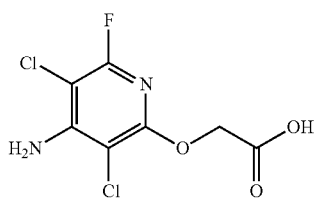 [SMILES: Nc1c(Cl)c(F)nc(OCC(=O)O)c1Cl]

Exemplary uses of fluoroxypyr is described in *The Pesticide Manual*, Fifteenth Edition, 2009. Exemplary uses of fluoroxypyr include its use for post-emergence foliar application to control broadleaf weeds, e.g., in small grain crops, control *Rumex* spp. and *Urtilca dioica* in pastures, and control *Trifolium repens* in amenity grassland. Other exemplary uses include its use to control herbaceous and woody broadleaf weeds, e.g., in orchards and plantation crops, and broadleaf brush, e.g., in conifer forests. Exemplary chemical forms of fluoroxypyr include, for example, fluoroxypyr MHE, which is 1-methylheptyl 2-[(4-amino-3,5-dichloro-6-fluoro-2-pyridinyl)oxy]acetate and possesses the following structure:

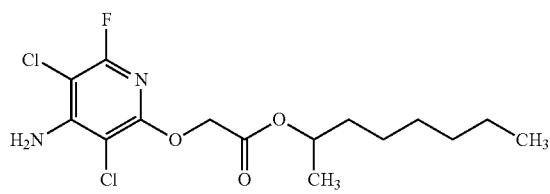 [SMILES: CCCCCCC(C)OC(=O)COc1nc(F)c(Cl)c(N)c1Cl]

As used herein, MCPA is 2-(4-chloro-2-methylphenoxy) acetic acid and possesses the following structure:

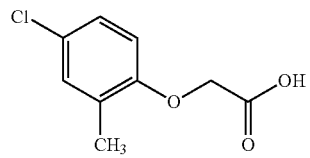

Exemplary uses of MCPA is described in *The Pesticide Manual*, Fifteenth Edition, 2009. Exemplary uses of MCPA include its use for post-emergence control of annual and perennial broadleaf weeds, e.g., in cereals, herbage seed crops, flax, rice vines, peas, potatoes, asparagas, grassland, turf, under fruit trees, and roadside verges and embankments. Other exemplary uses include its use to control broadleaf and woody weeds, e.g., in forestry, as well as aquatic broadleaf weeds. Exemplary chemical forms of MCPA include, for example, MCPA EHE is 2-ethylhexyl 2-(4-chloro-2-methylphenoxy)acetate and possesses the following structure:

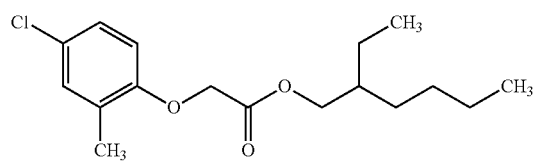 [SMILES: CCCCC(CC)COC(=O)COc1ccc(Cl)cc1C]

As used herein, mecoprop-P is (2R)-2-(4-chloro-2-methylphenoxy)propanoic acid and possesses the following structure:

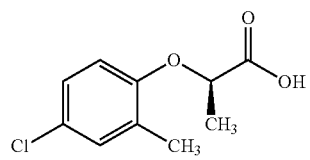

Exemplary uses of mecoprop-P are described in *The Pesticide Manual*, Fifteenth Edition, 2009. Exemplary uses of Mecoprop-P include its use for post-emergence control of broadleaf weeds, e.g., in wheat, barley, oats, herbage seed crops, and grassland.

As used herein, picloram is 4-amino-3,5,6-trichloro-2-pyridinecarboxylic acid and possesses the following structure:

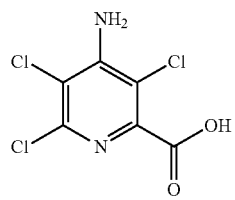 [SMILES: Nc1c(Cl)c(Cl)nc(C(=O)O)c1Cl]

Exemplary uses of picloram are described in *The Pesticide Manual*, Fifteenth Edition, 2009. Exemplary uses of picloram include its use for management of unwanted vegetation, e.g., in rangeland, grass pastures, forestry, as well as non-crop land and right-of-way sites. Exemplary chemical forms of picloram include, for example, picloram $K^+$ salt, which is 4-amino-3,5,6-trichloro-2-pyridinecarboxylic acid monopotassium salt and possesses the following structure:

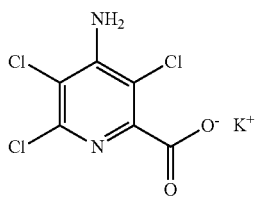 [SMILES: Nc1c(Cl)c(Cl)nc(C(=O)[O-])c1Cl ; [K+]]

As used herein, quinclorac is 3,7-dichloro-8-quinolinecarboxylic acid and possesses the following structure:

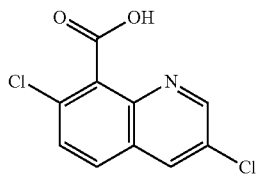 [SMILES: O=C(O)c1c(Cl)ccc2cc(Cl)cnc12]

Exemplary uses of quiclorac are described in *The Pesticide Manual*, Fifteenth Edition, 2009. Exemplary uses of quinclorac include its use for pre- and post-emergence control of specific grass and broadleaf weeds, e.g., in direct-seeded and transplanted rice.

As used herein, triclopyr is 2-[(3,5,6-trichloro-2-pyridinyl)oxy]acetate and possesses the following structure:

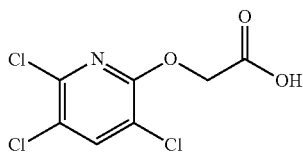 [SMILES: O=C(O)COc1nc(Cl)c(Cl)cc1Cl]

Exemplary uses of triclopyr are described in *The Pesticide Manual*, Fifteenth Edition, 2009. Exemplary uses of triclopyr include its use for control of woody plants and broadleaf weed species, e.g., in grassland, uncultivated land, industrial areas, coniferous forests, rice and plantation crops. Exemplary chemical forms of triclopyr include, for example, triclopyr TEA, which is 2-[(3,5,6-trichloro-2-pyridinyl)oxy]acetic acid compound with N,N-diethylethanamine and possesses the following structure:

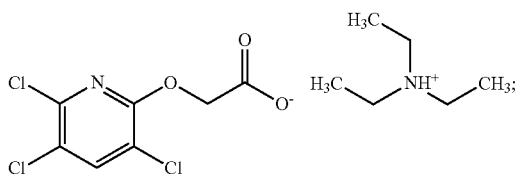

triclopyr choline, which is 2-hydroxy-N,N,N-trimethylethanaminium 2-((3,5,6-trichloropyridin-2-yl)oxy)acetate and possesses the following structure:

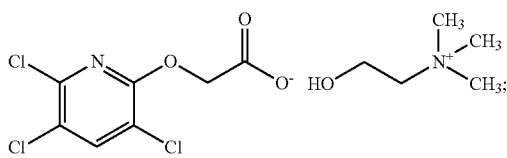

and
triclopyr BEE, which is 2-butoxyethyl 2-[(3,5,6-trichloro-2-pyridinyl)oxy]acetate and possesses the following structure:

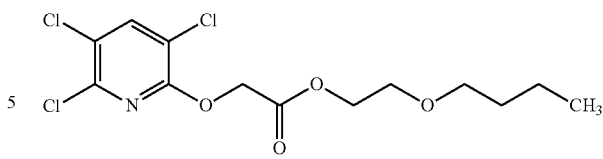

As used herein, halauxifen-methyl(methyl 4-amino-3-chloro-6-(4-chloro-2-fluoro-3-methoxyphenyl)picolinate) possesses the following structure:

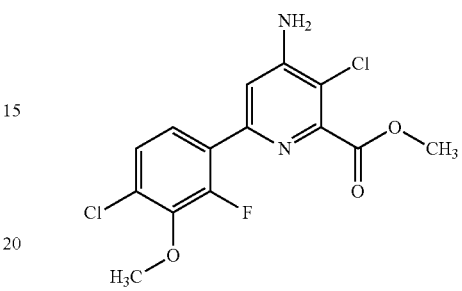

It is described in in U.S. Pat. No. 7,314,849 B2, which is incorporated herein by reference in its entirety. Exemplary uses of halauxifen-methyl include its use to control broadleaf weeds, e.g., in cereal crops. Halauxifen-methyl may be used as other forms, e.g., halauxifen $K^+$ (potassium 4-amino-3-chloro-6-(4-chloro-2-fluoro-3-methoxyphenyl)picolinate), which possesses the following structure:

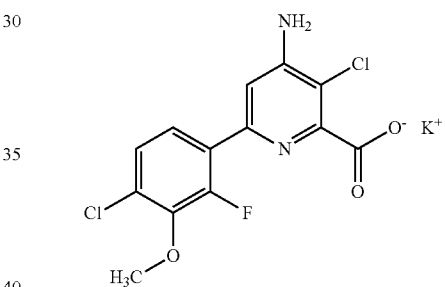

As used herein, herbicide means a compound, e.g., active ingredient that kills, controls or otherwise adversely modifies the growth of plants.

As used herein, a herbicidally effective or vegetation controlling amount is an amount of active ingredient which causes an adversely modifying effect to the vegetation e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as preemergence, postemergence, foliar (broadcast, directed, banded, spot, mechanical, over-the-top, or rescue), and in-water applications (emerged and submerged vegetation, broadcast, spot, mechanical, water-injected, granular broadcast, granular spot, shaker bottle, or stream spray) via hand, backpack, machine, tractor, or aerial (airplane and helicopter) application methods.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are herbicidal compositions comprising a herbicidally effective amount of (a) a compound of the formula (I)

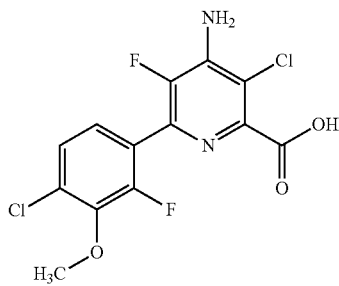

or an agriculturally acceptable salt or ester of thereof, and
(b) a synthetic auxin herbicide.

Provided herein are also methods of controlling undesirable vegetation comprising contacting the vegetation or the locus thereof, i.e., area adjacent to the vegetation, with or applying to the soil or water to prevent the emergence or growth of vegetation a herbicidally effective amount of the compound of formula (I) or agriculturally acceptable salt or ester thereof and (b) a synthetic auxin herbicide. In certain embodiments, the methods employ the compositions described herein. In certain embodiments, the synthetic auxin is 2,4-D, 2,4-DB, aminocyclopyrachlor, aminopyralid, clomeprop-P, clopyralid, dicamba, diclorprop-P, fluoroxypyr methylheptyl ester (MHE), MCPA, picloram, quinclorac, triclopyr, and halauxifen-methyl(methyl 4-amino-3-chloro-6-(4-chloro-2-fluoro-3-methoxyphenyl)picolinate), or an agriculturally acceptable salt or ester thereof.

Furthermore, in some embodiments, the combination of compound (I) or agriculturally acceptable salt or ester thereof and synthetic auxin herbicides, or an agriculturally acceptable salt or ester thereof exhibits synergism, e.g., the herbicidal active ingredients are more effective in combination than when applied individually. Synergism has been defined as "an interaction of two or more factors such that the effect when combined is greater than the predicted effect based on the response of each factor applied separately." Senseman, S., ed. Herbicide Handbook. $9^{th}$ ed. Lawrence: Weed Science Society of America, 2007. In certain embodiments, the compositions exhibit synergy as determined by the Colby's equation. Colby, S. R. 1967. Calculation of the synergistic and antagonistic response of herbicide combinations. Weeds 15:20-22.

In certain embodiments of the compositions and methods described herein, the compound of formula (I), i.e., the carboxylic acid, is employed. In certain embodiments, a carboxylate salt of the compound of formula (I) is employed. In certain embodiments, an aralkyl or alkyl ester is employed. In certain embodiments, a benzyl, substituted benzyl, or $C_{1-4}$ alkyl, e.g., n-butyl ester is employed. In certain embodiments, the benzyl ester is employed.

In some embodiments, the compound of formula (I) or salt or ester thereof and synthetic auxin are formulated in one composition, tank mixed, applied simultaneously, or applied sequentially.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature undesirable vegetation to achieve the maximum control of weeds.

In some embodiments, the compositions and methods provided herein are utilized to control weeds in crops, including but not limited to direct-seeded rice, water-seeded rice, transplanted rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In certain embodiments, the compositions and methods provided herein are utilized to control weeds in rice. In certain embodiments, the rice is direct-seeded, water-seeded, or transplanted rice.

The compositions and methods described herein may be used to control undesirable vegetation in glyphosate-tolerant-, 5-enolpyruvylshikimate-3-phosphate (EP SP) synthase inhibitor-tolerant-, glufosinate-tolerant-, glutamine synthetase inhibitor-tolerant-, dicamba-tolerant-, phenoxy auxin-tolerant-, pyridyloxy auxin-tolerant-, auxin-tolerant-, auxin transport inhibitor-tolerant-, aryloxyphenoxypropionate-tolerant-, cyclohexanedione-tolerant-, phenylpyrazoline-tolerant-, acetyl CoA carboxylase (ACCase) inhibitor-tolerant-, imidazolinone-tolerant-, sulfonylurea-tolerant-, pyrimidinylthiobenzoate-tolerant-, triazolopyrimidine-tolerant-, sulfonylaminocarbonyltriazolinone-tolerant-, acetolactate synthase (ALS) or acetohydroxy acid synthase (AHAS) inhibitor-tolerant-, 4-hydroxyphenyl-pyruvate dioxygenase (HPPD) inhibitor-tolerant-, phytoene desaturase inhibitor-tolerant-, carotenoid biosynthesis inhibitor-tolerant-, protoporphyrinogen oxidase (PPO) inhibitor-tolerant-, cellulose biosynthesis inhibitor-tolerant-, mitosis inhibitor-tolerant-, microtubule inhibitor-tolerant-, very long chain fatty acid inhibitor-tolerant-, fatty acid and lipid biosynthesis inhibitor-tolerant-, photosystem I inhibitor-tolerant-, photosystem II inhibitor-tolerant-, triazine-tolerant-, and bromoxynil-tolerant-crops (such as, but not limited to, soybean, cotton, canola/oilseed rape, rice, cereals, corn, sorghum, sunflower, sugar beet, sugarcane, turf, etc.), for example, in conjunction with glyphosate, EPSP synthase inhibitors, glufosinate, glutamine synthase inhibitors, dicamba, phenoxy auxins, pyridyloxy auxins, synthetic auxins, auxin transport inhibitors, aryloxyphenoxypropionates, cyclohexanediones, phenylpyrazolines, ACCase inhibitors, imidazolinones, sulfonylureas, pyrimidinylthiobenzoates, triazolopyrimidines, sulfonylaminocarbonyltriazolinones, ALS or AHAS inhibitors, HPPD inhibitors, phytoene desaturase inhibitors, carotenoid biosynthesis inhibitors, PPO inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil. The compositions and methods may be used in controlling undesirable vegetation in crops possessing multiple or stacked traits conferring tolerance to multiple chemistries and/or inhibitors of multiple modes of action. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation, as a tank mix, or sequentially.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture). The compositions and methods provided herein are utilized to control undesirable vegetation. Undesirable vegetation includes, but is not limited to, undesirable vegetation that occurs in rice, cereals, wheat, barley, oats, rye, sorghum, corn/maize, sugarcane, sunflower, oilseed rape, canola, sugar beet, soybean, cotton, pineapple, pastures, grasslands, rangelands, fallowland, turf, tree and vine orchards, aquatics, plantation crops, vegetables, industrial vegetation management (IVM) and rights-of-way (ROW).

In some embodiments, the methods provided herein are utilized to control undesirable vegetation in rice. In certain embodiments, the undesirable vegetation is *Brachiaria platyphylla* (Groseb.) Nash or *Urochloa platyphylla* (Nash) R. D. Webster (broadleaf signalgrass, BRAPP), *Digitaria sanguinalis* (L.) Scop. (large crabgrass, DIGSA), *Echinochloa* species (ECHSS), *Echinochloa crus-galli* (L.) P. Beauv. (barnyardgrass, ECHCG), *Echinochloa crus-pavonis* (Kunth) Schuh. (gulf cockspur, ECHCV), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Echinochloa phyllopogon* (Stapf) Koso-Pol. (rice barnyardgrass, ECHPH), *Echinochloa polystachya* (Kunth) Hitchc. (creeping river grass, ECHPO), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Pres') Hitchc. (Amazon sprangletop, LEFPA), *Oryza* species (red and weedy rice, ORYSS), *Panicum dichotomiflorum* (L.) Michx. (fall panicum, PANDI), *Paspalum dilatatum* Poir. (dallisgrass, PASDI), *Rottboellia cochinchinensis* (Lour.) W. D. Clayton (itchgrass, ROOEX), *Cyperus* species (CYPSS), *Cyperus difformis* L. (smallflower flatsedge, CYPDI), *Cyperus dubius* Rottb. (MAPDU), *Cyperus esculentus* L. (yellow nutsedge, CYPES), *Cyperus iria* L. (rice flatsedge, CYPIR), *Cyperus rotundus* L. (purple nutsedge, CYPRO), *Cyperus serotinus* Rottb./C. B. Clarke (CYPSE), *Eleocharis* species (ELOSS), *Fimbristylis miliacea* (L.) Vahl (globe fringerush, FIMMI), *Schoenoplectus* species (SCPSS), *Schoenoplectus juncoides* Roxb. (Japanese bulrush, SCPJU), *Bolboschoenus maritimus* (L.) Palla or *Schoenoplectus maritimus* L. Lye (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago-aquatica* L. (common waterplantain, ALSPA), *Amaranthus* species, (pigweeds and amaranths, AMASS), *Ammannia coccinea* Rottb. (redstem, AMMCO), *Commelina benghalensis* L. (Benghal dayflower, COMBE), *Eclipta alba* (L.) Hassk. (American false daisy, ECLAL), *Heteranthera limosa* (SW.) Willd./Vahl (ducksalad, HETLI), *Heteranthera reniformis* R. & P. (roundleaf mudplantain, HETRE), *Ipomoea* species (morningglories, IPOSS), *Ipomoea hederacea* (L.) Jacq. (ivyleaf morningglory, IPOHE), *Lindernia dubia* (L.) Pennell (low false pimpernel, LIDDU), *Ludwigia* species (LUDSS), *Ludwigia linifolia* Poir. (southeastern primrose-willow, LUDLI), *Ludwigia octovalvis* (Jacq.) Raven (longfruited primrose-willow, LUDOC), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals. In certain embodiments, the undesirable vegetation is *Alopecurus myosuroides* Huds. (blackgrass, ALOMY), *Apera spica-venti* (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.)

Roemer & J. A. Schultes (yellow foxtail, SETLU), *Setaria viridis* (L.) Beauv. (green foxtail, SETVI), *Amaranthus retroflexus* L. (redroot pigweed, AMARE), *Brassica* species (BRSSS), *Chenopodium album* L. (common lambsquarters, CHEAL), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Sinapis* species (SINSS), *Sinapis arvensis* L. (wild mustard, SINAR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture, fallowland, IVM and ROW. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Daucus carota* L. (wild carrot, DAUCA), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), Solidago species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops, tree and vine crops, and perennial crops. In certain embodiments, the undesirable vegetation is *Alopecurus myosuroides* Huds. (blackgrass, ALOMY), *Avena fatua* L. (wild oat, AVEFA), *Brachiaria decumbens* Stapf. or *Urochloa decumbens* (Stapf) R. D. Webster (Surinam grass, BRADC), *Brachiaria brizantha* (Hochst. ex A. Rich.) Stapf. or *Urochloa brizantha* (Hochst. ex A. Rich.) R.D. (beard grass, BRABR), *Brachiaria platyphylla* (Groseb.) Nash or *Urochloa platyphylla* (Nash) R. D. Webster (broadleaf signalgrass, BRAPP), *Brachiaria plantaginea* (Link) Hitchc. or *Urochloa plantaginea* (Link) R. D. Webster (alexandergrass, BRAPL), *Cenchrus echinatus* L. (southern sandbar, CENEC), *Digitaria horizontalis* Willd. (Jamaican crabgrass, DIGHO), *Digitaria insularis* (L.) Mez ex Ekman (sourgrass, TRCIN), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Eleusine indica* (L.) Gaertn. (goosegrass, ELEIN), *Lolium multiflorum* Lam. (Italian ryegrass, LOLMU), *Panicum dichotomiflorum* Michx. (fall panicum, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) Moench ssp. Arundinaceum (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), Amaranthus species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Anoda cristata* (L.) Schlecht. (spurred anoda, ANVCR), *Asclepias syriaca* L. (common milkweed, ASCSY), *Bidens pilosa* L. (hairy beggarticks, BIDPI), *Borreria* species (BOISS), *Borreria alata* (Aubl.) DC. or *Spermacoce alata* Aubl. (broadleaf buttonweed, BOILF), *Spermacose latifolia* (broadleaved button weed, BOILF), *Chenopodium album* L. (common lambsquarters, CHEAL), *Cirsium* arvense (L.) Scop. (Canada thistle, CIRAR), *Commelina benghalensis* L. (tropical spiderwort, COMBE), *Datura stramonium* L. (jimsonweed, DATST), *Daucus carota* L. (wild carrot, DAUCA), *Euphorbia heterophylla* L. (wild poinsettia, EPHHL), *Euphorbia hirta* L. or *Chamaesyce hirta* (L.) Millsp. (garden spurge, EPHHI), *Euphorbia dentata* Michx. (toothed spurge, EPHDE), *Erigeron bonariensis* L. or *Conyza bonariensis* (L.) Cronq. (hairy fleabane, ERIBO), *Erigeron canadensis* L. or *Conyza canadensis* (L.) Cronq. (Canadian fleabane, ERICA), *Conyza sumatrensis* (Retz.) E. H. Walker (tall fleabane, ERIFL), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Richardia* species (pusley, RCHSS), *Sida* species (sida, SIDSS), *Sida spinosa* L. (prickly sida, SIDSP), *Sinapis arvensis* L. (wild mustard, SINAR), *Solanum ptychanthum* Dunal (eastern black nightshade, SOLPT), *Tridax procumbens* L. (coat buttons, TRQPR), or *Xanthium strumarium* L. (common cocklebur, XANST).

In some embodiments, the methods provided herein are utilized to control undesirable vegetation in turf. In certain embodiments, the undesirable vegetation is *Bellis perennis* L. (English daisy, BELPE), *Cyperus esculentus* L. (yellow nutsedge, CYPES), *Cyperus* species (CYPSS), *Digitaria sanguinalis* (L.) Scop. (large crabgrass, DIGSA), *Diodia virginiana* L. (Virginia buttonweed, DIQVI), *Euphorbia* species (spurge, EPHSS), *Glechoma hederacea* L. (ground ivy, GLEHE), *Hydrocotyle umbellata* L. (dollarweed, HYDUM), *Kylling a* species (kylling a, KYLSS), *Lamium amplexicaule* L. (henbit, LAMAM), *Murdannia nudiflora* (L.) Brenan (doveweed, MUDNU), *Oxalis* species (woodsorrel, OXASS), *Plantago major* L. (broadleaf plantain, PLAMA), *Plantago lanceolata* L. (buckhornlnarrowleaf plantain, PLALA), *Phyllanthus urinaria* L. (chamberbitter, PYLTE), *Rumex obtusifolius* L. (broadleaf dock, RUMOB), *Stachys floridana* Shuttlew. (Florida betony, STAFL), *Stellaria media* (L.) Vill. (common chickweed, STEME), *Taraxacum officinale* G. H. Weber ex Wiggers (dandelion, TAROF), *Trifolium repens* L. (white clover, TRFRE), or *Viola* species (wild violet, VIOSS).

In some embodiments, the compositions and methods provided herein are utilized to control undesirable vegetation consisting of grass, broadleaf and sedge weeds. In certain embodiments, the compositions and methods provided herein are utilized to control undesirable vegetation including, but not limited to, Amaranthus, Brachiaria, Brassica, Cassia, Centaurea, Cirsium, Cyperus, Digitaria, Echinochloa, Eleusine, Ischaemum, Leptochloa, Panicum, Polygonum, Sida, Sinapis, Solidago, Sonchus, Sorghum, Schoenoplectus, Stellaria, Trifolium and Viola.

In some embodiments, the combination of compound (I) or agriculturally acceptable ester or salt thereof and 2,4-D, aminocyclopyrachlor, aminopyralid, clomeprop-P, clopyralid, dicamba, diclorprop-P, fluoroxypyr methylheptyl ester (MHE), MCPA, picloram, quinclorac, triclopyr, and halauxifen-methyl(methyl 4-amino-3-chloro-6-(4-chloro-2-fluoro- 3-methoxyphenyl)picolinate), or agriculturally acceptable salt or ester thereof, is used to control *Amaranthus retroflexus* (L.) (redroot pigweed, AMARE), *Brachiaria platyphylla* (Griseb.) Nash or *Urochloa platyphylla* (Nash) R. D. Webster (broadleaf signalgrass, BRAPP), *Brassica napus* (L.) (volunteer canola, BRSNN), *Cassia obtusifolia* L. (sicklepod, CASOB), *Cirsium arvense* (L.) Scop. (Canada thistle, CIRAR), *Centaurea maculosa* LAM. (knapweed, spotted, CENMA), *Cirsium arvense* (L.) SCOP. (thistle, Canada, CIRAR), *Cyperus difformis* L. (smallflower umbrella sedge, CYPDI), *Cyperus esculentus* (L). (yellow nutsedge, CYPES), *Cyperus iria* L. (rice flatsedge, CYPIR), *Cyperus rotundus* L. (purple nutsedge, CYPRO), *Digitaria sanguinalis* (L.) Scop. (large crabgrass, DIGSA), *Echinochloa crus-galli* (L.) Beauv. (barnyardgrass, ECHCG), *Echinochloa colona* (L.) Link (junglerice, ECHCO), *Echinochloa oryzoides* (Ard.) Fritsch (early watergrass, ECHOR), *Eleusine indica* (L.) Gaertn. (goosegrass, ELEIN), *Ischaemum rugosum* Salisb. (saramollagrass, ISCRU), *Leptochloa chinensis* (L.) Nees (Chinese sprangletop, LEFCH), *Panicum dichotomiflorum* Michx. (fall panicum, PANDI), *Panicum miliaceum* L. (wild-proso millet, PANMI), *Polygonum convolvulus* (L.), (wild buckwheat, POLCO), *Schoenoplectus juncoides* (Roxb.) Palla (Japanese bulrush, SCPJU), *Bolboschoenus maritimus* (L.) Palla or *Schoenoplectus maritimus* (L.) Lye (sea clubrush, SCPMA), *Sorghum halepense* (L.) Pers. (johnsongrass, *Sida spinosa* L. (sida, prickly, SIDSP), *Sinapis arvensis* L. (mustard, wild, SINAR), *Solidago* L. spec. (goldenrod, SOOSS), *Sonchus arvensis* L. (sowthistle, field, SONAR), *Sorghum halepense* (L.) Pers. (johnsongrass, SORHA), *Stellaria media* (L.) Vill. (common chickweed, STEME), *Trifolium repens* L. (clover, Dutch, TRFRE) and *Viola tricolor* (L.) (wild pansy, VIOTR).

The compounds of formula I or agriculturally acceptable salt or ester thereof may be used to control herbicide resistant or tolerant weeds. The methods employing the combination of a compound of formula I or agriculturally acceptable salt or ester thereof and the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), photosystem II inhibitors (e.g., phenylcarbamates, pyridazinones, triazines, triazinones, uracils, amides, ureas, benzothiadiazinones, nitriles, phenylpyridazines), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors, (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid biosynthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidindiones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, and multiple herbicide modes-of-action, and biotypes with multiple resistance or tolerance mechanisms (e.g., target site resistance or metabolic resistance).

In certain embodiments of the compositions and methods described herein, the compound of formula (I) or salt or ester thereof is used in combination with 2,4-D, or carboxylate salt or ester thereof. With regard to the compositions, in some embodiments, the weight ratio of the compound of formula (I) or salt or ester thereof to 2,4-D or carboxylate salt or ester thereof is within the range of from about 1:1120 to about 4:1. In certain embodiments, the weight ratio of the compound of formula (I) or salt or ester thereof to 2,4-D or carboxylate salt or ester thereof is within the range of from 1:128 to about 1:1. In certain embodiments, the weight ratio of the compound of formula (I) or salt or ester thereof to 2,4-D or carboxylate salt or ester thereof is within the range of from about 1:200 to about 1:1. In certain embodiments, the weight ratio of the compound of formula (I) or salt or ester thereof to 2,4-D or carboxylate salt or ester thereof is within the range of from about 1:96 to about 1:2. In certain embodiments, the compositions provided herein comprise the compound of formula (I) or its benzyl ester and 2,4-D DMA, 2,4-D choline, or 2,4-D EHE. In one embodiment, the composition comprises the compound of formula (I) and 2,4-D DMA, wherein the weight ratio of the compound of formula (I) to 2,4-D DMA is about 1:56 to about 1:4. In one embodiment, the composition comprises the benzyl ester of the compound of formula (I) and 2,4-D DMA, wherein the weight ratio of the benzyl ester of the compound of formula (I) to 2,4-D DMA is about 1:56 to about 1:2. In one embodiment, the composition comprises the compound of formula (I) and 2,4-D choline, wherein the weight ratio of the compound of formula (I) to 2,4-D choline is about 1:84 to about 1:6.9. In one embodiment, the composition comprises the benzyl ester of the compound of formula (I) and 2,4-D choline, wherein the weight ratio of the benzyl ester of the compound of formula (I) to 2,4-D choline is about 1:96 to about 1:6. In one embodiment, the composition comprises the compound of formula (I) and 2,4-D EHE, wherein the weight ratio of the compound of formula (I) to 2,4-D EHE is about 1:56 to about 1:4. In one embodiment, the composition comprises the benzyl ester of the compound of formula (I) and 2,4-D EHE, wherein the weight ratio of the benzyl ester of the compound of formula (I) to 2,4-D EHE is about 1:56 to about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 37 grams acid equivalent per hectare (gae/ha) to about 2540 gae/ha based on the total amount of active ingredients in the composition. In certain embodiments, the composition is applied at an application rate of from about 39 grams acid equivalent per hectare (gae/ha) to about 515 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and 2,4-D or carboxylate salt or ester thereof, e.g., sequentially or simultaneously. In some embodiments, the 2,4-D or carboxylate salt or ester thereof is applied at a rate from about 35 gae/ha to about 480 gae/ha and the compound of formula (I) of salt or ester thereof is applied at a rate from about 2 gae/ha to about 300 gae/ha. In some embodiments, the 2,4-D or carboxylate salt or ester thereof is 2,4-DB, 2,4-D choline, 2,4-D DMA or 2,4-D EHE. In some embodiments, the 2,4-D or carboxylate salt or ester thereof is applied at a rate from about 17 gai/ha to about 1000 gai/ha and the compound of formula (I) of salt or ester thereof is applied at a rate from about 0.5 g acid equivalent per hectare (gae/ha) to about 70 gae/ha. In some embodiments, the 2,4-D or carboxylate salt or ester thereof is applied at a rate from about 35 gai/ha to about 480 gai/ha and the compound of formula (I) of salt or ester thereof is applied at a rate from about 1.1 g acid equivalent per hectare (gae/ha) to about 35 gae/ha. In certain embodiments, the methods utilize the compound of formula (I), or its benzyl ester and 2,4-D DMA, 2,4-D choline, or 2,4-D EHE. In one embodiment, the methods utilize the compound of formula (I) and 2,4-D DMA, wherein the compound of formula (I) is applied at a rate of from about 3.75 g acid equivalent per hectare (gae/ha) to about 35 gae/ha, and 2,4-D DMA is applied at a rate of about 70 gai/ha to about 280 gai/ha. In one embodiment, the methods utilize the benzyl ester of the compound of formula (I) and 2,4-D DMA, wherein the benzyl ester of the compound of formula (I) is applied at a rate of from about 3.75 g acid equivalent per hectare (gae/ha) to about 35 gae/ha, and 2,4-D DMA is applied at a rate of about 35 gai/ha to about 280 gai/ha. In one embodiment, the methods utilize the compound of formula (I) and 2,4-D choline, wherein the compound of formula (I) is applied at a rate of from about 4.38 g acid equivalent per hectare (gae/ha) to about 35 gae/ha, and 2,4-D choline is applied at a rate of about 105 gai/ha to about 480 gai/ha. In one embodiment, the methods utilize the benzyl ester of the compound of formula (I) and 2,4-D choline, wherein the benzyl ester of the compound of formula (I) is applied at a rate of from about 1.1 g acid equivalent per hectare (gae/ha) to about 35 gae/ha, and 2,4-D choline is applied at a rate of about 50 gai/ha to about 480 gai/ha. In one embodiment, the methods utilize the compound of formula (I) and 2,4-D EHE, wherein the compound of formula (I) is applied at a rate of from about 4.38 g acid equivalent per hectare (gae/ha) to about 35 gae/ha, and 2,4-D EHE is applied at a rate of about 70 gai/ha to about 280 gai/ha. In one embodiment, the methods utilize the benzyl ester of the compound of formula (I) and 2,4-D EHE, wherein the benzyl ester of the compound of formula (I) is applied at a rate of from about 4.38 g acid equivalent per hectare (gae/ha) to about 17.5 gae/ha, and 2,4-D EHE is applied at a rate of about 70 gai/ha to about 280 gai/ha. In certain embodiments, the methods and compositions utilizing the compound of formula (I) or salt or ester thereof in combination with 2,4-D or carboxylate salt or ester thereof are used to control ECHCG, LEFCH, ECHOR, CYPRO, SCPJU, CENMA, SINAR, SONAR, POLCO, PANDI, ELEIN, PANMI, DIGSA, ECHCO, CYPES, CYPIR, SCPMA, CASOB, or BRAPP.

In certain embodiments of the compositions and methods described herein, the compound of formula (I) or salt or ester thereof is used in combination with aminocyclopyrachloror carboxylate salt or ester thereof. With regard to the compositions, in some embodiments, the weight ratio of the compound of formula (I) or salt or ester thereof aminocyclopyrachloror carboxylate salt or ester thereof is within the range of from about 1:140 to about 34:1. In certain embodiments, the weight ratio of the compound of formula (I) or salt or ester thereof to aminocyclopyrachloror carboxylate salt or ester thereof is within the range of from 1:91 to about 12:1. In certain embodiments, the weight ratio of the compound of formula (I) or salt or ester thereof to aminocyclopyrachloror carboxylate salt or ester thereof is within the range of from 1:4 to about 2:1. In certain embodiments, the compositions comprise the compound of formula (I) or its benzyl or n-butyl ester and aminocyclopyrachlor. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 10 grams acid equivalent per hectare (gae/ha) to about 580 gae/ha based on the total amount of active ingredients in the composition. In certain embodiments, the composition is applied at an application rate of from about 11 grams acid equivalent per hectare (gae/ha) to about 300 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and aminocyclopyrachloror carboxylate salt or ester thereof, e.g., sequentially or simultaneously. In some embodiments, the aminocyclopyrachloror carboxylate salt or ester thereof is applied at a rate from about 8.8 gae/ha to about 280 gae/ha and the compound of formula (I) of salt or ester thereof is applied at a rate from about 2 gae/ha to about 300 gae/ha. In one embodiment, the aminocyclopyrachloror carboxylate salt or ester thereof is applied at a rate from about 8.75 gae/ha to about 17.5 gae/ha and the compound of formula (I) of salt or ester thereof is applied at a rate from about 4.4 gae/ha to about 17.5 gae/ha. In certain embodiments, the methods utilize the compound of formula (I) or its benzyl or n-butyl ester and aminocyclopyrachlor. In certain embodiments, the methods and compositions utilizing the compound of formula (I) or salt or ester thereof in combination with aminocyclopyrachloror carboxylate salt or ester thereof are used to control TRFRE, SINAR, or CENMA.

In certain embodiments of the compositions and methods described herein, the compound of formula (I) or salt or ester thereof is used in combination with aminopyralid or carboxylate salt or ester thereof. With regard to the compositions, in some embodiments, the weight ratio of the compound of formula (I) or salt or ester thereof to aminopyralid or carboxylate salt or ester thereof is within the range of from about 1:60 to about 100:1. In certain embodiments, the weight ratio of the compound of formula (I) or salt or ester thereof to aminopyralid or carboxylate salt or ester thereof is within the range of from 1:8 to about 6:1. In certain embodiments, the weight ratio of the compound of formula (I) or salt or ester thereof to aminopyralid or carboxylate salt or ester thereof is within the range of from about 1:16 to about 6:1. In certain embodiments, the weight ratio of the compound of formula (I) or salt or ester thereof to aminopyralid or carboxylate salt or ester thereof is within the range of from about 1:8 to about 3:1. In certain embodiments, the compositions provided herein comprise the compound of formula (I) or its benzyl ester and aminopyralid or aminopyralid TIPA. In one embodiment, the composition comprises the benzyl ester of the compound of formula (I) and aminopyralid, wherein the weight ratio of the benzyl ester of the compound of formula (I) to aminopyralid is about 3:1. In one embodiment, the composition comprises the benzyl ester of the compound of formula (I) and aminopyralid TIPA, wherein the weight ratio of the benzyl ester of the compound of formula (I) to aminopyralid TIPA is about 1:8 to about 1:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 5 grams acid equivalent per hectare (gae/ha) to about 420 gae/ha based on the total amount of active ingredients in the composition. In certain embodiments, the composition is applied at an application rate of from about 7 grams acid equivalent per hectare (gae/ha) to about 53 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and aminopyralid or carboxylate salt or ester thereof, e.g., sequentially or simultaneously. In some embodiments, the aminopyralid or carboxylate salt or ester thereof is applied at a rate from about 3 gae/ha to about 120 gae/ha and the compound of formula (I) of salt or ester thereof is applied at a rate from about 2 gae/ha to about 300 gae/ha. In some embodiments, the aminopyralid or carboxylate salt or ester thereof is applied at a rate from about 1 gai/ha to about 70 gai/ha and the compound of formula (I) of salt or ester thereof is applied at a rate from about 2 g acid equivalent per hectare (gae/ha) to about 45 gae/ha. In some embodiments, the aminopyralid or carboxylate salt or ester thereof is applied at a rate from about 3 gai/ha to about 35 gai/ha and the compound of formula (I) of salt or ester thereof is applied at a rate from about 4.4 g acid equivalent per hectare (gae/ha) to about 17.5 gae/ha. In certain embodiments, the methods utilize the compound of formula (I), or its benzyl ester and aminopyralid or aminopyralid TIPA. In one embodiment, the methods utilize the benzyl ester of the compound of formula (I) and aminopyralid, wherein the benzyl ester of the compound of formula (I) is applied at a rate of about 8.75 g acid equivalent per hectare (gae/ha), and aminopyralid is applied at a rate of about 3 gai/ha. In one embodiment, the methods utilize the benzyl ester of the compound of formula (I) and aminopyralid TIPA, wherein the benzyl ester of the compound of formula (I) is applied at a rate of from about 4.4 g acid equivalent per hectare (gae/ha) to about 17.5 gae/ha, and aminopyralid TIPA is applied at a rate of about 3 gai/ha to about 35 gai/ha. In certain embodiments, the methods and compositions utilizing the compound of formula (I) or salt or ester thereof in combination with aminopyralid or carboxylate salt or ester thereof are used to control POLCO, CIRAR, BRSNN, TRFRE, SINAR, SOOSS, or CENMA.

In certain embodiments of the compositions and methods described herein, the compound of formula (I) or salt or ester thereof is used in combination with clomeprop-P or salt or ester thereof. With regard to the compositions, in some embodiments, the weight ratio of the compound of formula (I) or salt or ester thereof to clomeprop-P or salt or ester thereof is within the range of from about 1:200 to about 6:1. In certain embodiments, the weight ratio of the compound of formula (I) or salt or ester thereof to clomeprop-P or salt or ester thereof is within the range of from 1:159 to about 1:1. In certain embodiments, the compositions comprise the compound of formula (I) or its benzyl or n-butyl ester and clomeprop-P. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 52 grams acid equivalent per hectare (gae/ha) to about 700 gae/ha based on the total amount of active ingredients in the composition. In certain embodiments, the composition is applied at an application rate of from about 53 grams acid equivalent per hectare (gae/ha) to about 400 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and clomeprop-P or salt thereof, e.g., sequentially or simultaneously. In some embodiments, the clomeprop-P or salt or ester thereof is applied at a rate from about 50 gae/ha to about 400 gae/ha and the compound of formula (I) of salt or ester thereof is applied at a rate from about 2 gae/ha to about 300 gae/ha. In certain embodiments, the methods utilize the compound of formula (I) or its benzyl or n-butyl ester and clomeprop-P.

In certain embodiments of the compositions and methods described herein, the compound of formula (I) or salt or ester thereof is used in combination with clopyralid or carboxylate salt or ester thereof. With regard to the compositions, in some embodiments, the weight ratio of the compound of formula (I) or salt or ester thereof to clopyralid or carboxylate salt or ester thereof is within the range of from about 1:280 to about 9:1. In certain embodiments, the weight ratio of the compound of formula (I) or salt or ester thereof to clopyralid or carboxylate salt or ester thereof is within the range of from 1:23 to about 1:4. In certain embodiments, the weight ratio of the compound of formula (I) or salt or ester thereof to clopyralid or carboxylate salt or ester thereof is within the range of from about 1:32 to about 1:2. In certain embodiments, the weight ratio of the compound of formula (I) or salt or ester thereof to clopyralid or carboxylate salt or ester thereof is within the range of from about 1:16 to about 1:4. In certain embodiments, the compositions provided herein comprise the compound of formula (I) or its benzyl ester and clopyralid or clopyralid MEA. In one embodiment, the composition comprises the benzyl ester of the compound of formula (I) and clopyralid, wherein the weight ratio of the benzyl ester of the compound of formula (I) to clopyralid is about 1:5.7. In one embodiment, the composition comprises the benzyl ester of the compound of formula (I) and clopyralid MEA, wherein the weight ratio of the benzyl ester of the compound of formula (I) to clopyralid MEA is about 1:4 to about 1:16. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 37 grams acid equivalent per hectare (gae/ha) to about 860 gae/ha based on the total amount of active ingredients in the composition. In certain embodiments, the composition is applied at an application rate of from about 38 grams acid equivalent per hectare (gae/ha) to about 59 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and clopyralid or carboxylate salt or ester thereof, e.g., sequentially or simultaneously. In some embodiments, the clopyralid or carboxylate salt or ester thereof is applied at a rate from about 35 gae/ha to about 560 gae/ha and the compound of formula (I) of salt or ester thereof is applied at a rate from about 2 gae/ha to about 300 gae/ha. In some embodiments, the clopyralid or carboxylate salt or ester thereof is applied at a rate from about 17 gai/ha to about 100 gai/ha and the compound of formula (I) of salt or ester thereof is applied at a rate from about 1 g acid equivalent per hectare (gae/ha) to about 18 gae/ha. In some embodiments, the clopyralid or carboxylate salt or ester thereof is applied at a rate from about 35 gai/ha to about 50 gai/ha and the compound of formula (I) of salt or ester thereof is applied at a rate from about 2.2 g acid equivalent per hectare (gae/ha) to about 8.75 gae/ha. In certain embodiments, the methods utilize the compound of formula (I), or its benzyl ester and clopyralid or clopyralid MEA. In one embodiment, the methods utilize the benzyl ester of the compound of formula (I) and clopyralid, wherein the benzyl ester of the compound of formula (I) is applied at a rate of about 8.75 g acid equivalent per hectare (gae/ha), and clopyralid is applied at a rate of about 50 gai/ha. In one embodiment, the methods utilize the benzyl ester of the compound of formula (I) and clopyralid MEA, wherein the benzyl ester of the compound of formula (I) is applied at a rate of from about 2.2 g acid equivalent per hectare (gae/ha) to about 8.8 gae/ha, and clopyralid MEA is applied at a rate of about 35 gai/ha to 50 gai/ha. In certain embodiments, the methods and compositions utilizing the compound of formula (I) or salt or ester thereof in combination with clopyralid or carboxylate salt or ester thereof are used to control AMARE, CIRAR, or SOOSS.

In certain embodiments of the compositions and methods described herein, the compound of formula (I) or salt or ester thereof is used in combination with dicamba or carboxylate salt or ester thereof. With regard to the compositions, in some embodiments, the weight ratio of the compound of formula (I) or salt or ester thereof to dicamba or carboxylate salt or ester thereof is within the range of from about 1:1100 to about 8:1. In certain embodiments, the weight ratio of the compound of formula (I) or salt or ester thereof to dicamba or carboxylate salt or ester thereof is within the range of from 1:254 to about 1:1. In certain embodiments, the weight ratio of the compound of formula (I) or salt or ester thereof to dicamba or carboxylate salt or ester thereof is within the range of from about 1:120 to about 1:1. In certain embodiments, the weight ratio of the compound of formula (I) or salt or ester thereof to dicamba or carboxylate salt or ester thereof is within the range of from about 1:56 to about 1:3.3. In certain embodiments, the compositions provided herein comprise the compound of formula (I) or its benzyl ester and dicamba or dicamba DMA. In one embodiment, the composition comprises the compound of formula (I) and dicamba, wherein the weight ratio of the compound of formula (I) to dicamba is about 1:56 to about 1:3.3. In one embodiment, the composition comprises the benzyl ester of the compound of formula (I) and dicamba, wherein the weight ratio of the benzyl ester of the compound of formula (I) to dicamba is about 1:56 to about 1:4. In one embodiment, the composition comprises the benzyl ester of the compound of formula (I) and dicamba DMA, wherein the weight ratio of the benzyl ester of the compound of formula (I) to dicamba DMA is about 1:45.5 to about 1:11.4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 36 grams acid equivalent per hectare (gae/ha) to about 2500 gae/ha based on the total amount of active ingredients in the composition. In certain embodiments, the composition is applied at an application rate of from about 37 grams acid equivalent per hectare (gae/ha) to about 325 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and dicamba or carboxylate salt or ester thereof, e.g., sequentially or simultaneously. In some embodiments, the dicamba or carboxylate salt or ester thereof is applied at a rate from about 35 gae/ha to about 2200 gae/ha and the compound of formula (I) of salt or ester thereof is applied at a rate from about 2 gae/ha to about 300 gae/ha. In some embodiments, the dicamba or carboxylate salt or ester thereof is applied at a rate from about 17 gai/ha to about 600 gai/ha and the compound of formula (I) of salt or ester thereof is applied at a rate from about 0.5 g acid equivalent per hectare (gae/ha) to about 100 gae/ha. In some embodiments, the dicamba or carboxylate salt or ester thereof is applied at a rate from about 35 gai/ha to about 280 gai/ha and the compound of formula (I) of salt or ester thereof is applied at a rate from about 1.1 g acid equivalent per hectare (gae/ha) to about 42.4 gae/ha. In certain embodiments, the methods utilize the compound of formula (I), or its benzyl ester and dicamba or dicamba DMA. In one embodiment, the methods utilize the compound of formula (I) and dicamba, wherein the compound of formula (I) is applied at a rate of from about 5.3 g acid equivalent per hectare (gae/ha) to about 42.4 gae/ha, and dicamba is applied at a rate of about 140 gai/ha to about 280 gai/ha. In one embodiment, the methods utilize the benzyl ester of the compound of formula (I) and dicamba, wherein the benzyl ester of the compound of formula (I) is applied at a rate of from about 2.2 g acid equivalent per hectare (gae/ha) to about 35 gae/ha, and dicamba is applied at a rate of about 35 gai/ha to about 280 gai/ha. In one embodiment, the methods utilize the benzyl ester of the compound of formula (I) and dicamba DMA, wherein the benzyl ester of the compound of formula (I) is applied at a rate of about 1.1 g acid equivalent per hectare (gae/ha) to about 4.4 gae/ha, and dicamba DMA is applied at a rate of about 50 gai/ha. In certain embodiments, the methods and compositions utilizing the compound of formula (I) or salt or ester thereof in combination with dicamba or carboxylate salt or ester thereof are used to control LEFCH, CYPIR, ECHCO, ECHCG, ECHOR, SCPMA, AMARE, POLCO, BRSNN, SIDSP, SINAR, or CASOB.

In certain embodiments of the compositions and methods described herein, the compound of formula (I) or salt or ester thereof is used in combination with diclorprop-P or carboxylate salt or ester thereof. With regard to the compositions, in some embodiments, the weight ratio of the compound of formula (I) or salt or ester thereof to diclorprop-P or carboxylate salt or ester thereof is within the range of from about 1:5,700 to about 2:1. In certain embodiments, the weight ratio of the compound of formula (I) or salt or ester thereof to diclorprop-P or carboxylate salt or ester thereof is within the range of from 1:1000 to about 1:3. In certain embodiments, the compositions comprise the compound of formula (I) or its benzyl or n-butyl ester and diclorprop-P. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 142 grams acid equivalent per hectare (gae/ha) to about 11,700 gae/ha based on the total amount of active ingredients in the composition. In certain embodiments, the composition is applied at an application rate of from about 144 grams acid equivalent per hectare (gae/ha) to about 2290 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and diclorprop-P or salt thereof, e.g., sequentially or simultaneously. In some embodiments, the diclorprop-P or carboxylate salt or ester thereof is applied at a rate from about 140 gae/ha to about 11,400 gae/ha and the compound of formula (I) of salt or ester thereof is applied at a rate from about 2 gae/ha to about 300 gae/ha. In certain embodiments, the methods utilize the compound of formula (I) or its benzyl or n-butyl ester and diclorprop-P.

In certain embodiments of the compositions and methods described herein, the compound of formula (I) or salt or ester thereof is used in combination with fluoroxypyr or carboxylate salt or ester thereof. With regard to the compositions, in some embodiments, the weight ratio of the compound of formula (I) or salt or ester thereof to fluoroxypyr or carboxylate salt or ester thereof is within the range of from about 1:1120 to about 4:1. In certain embodiments, the weight ratio of the compound of formula (I) or salt or ester thereof to fluoroxypyr or carboxylate salt or ester thereof is within the range of from 1:127 to about 2:1. In certain embodiments, the weight ratio of the compound of formula (I) or salt or ester thereof to fluoroxypyr or carboxylate salt or ester thereof is within the range of from about 1:70 to about 1:1. In certain embodiments, the weight ratio of the compound of formula (I) or salt or ester thereof to fluoroxypyr or carboxylate salt or ester thereof is within the range of from about 1:35 to about 1:2. In certain embodiments, the compositions provided herein comprise the compound of formula (I) or its benzyl or n-butyl ester and fluoroxypyr or fluoroxypyr MHE. In one embodiment, the composition comprises the compound of formula (I) and fluoroxypyr MHE, wherein the weight ratio of the compound of formula (I) to fluoroxypyr MHE is about 1:28 to about 1:7. In one embodiment, the composition comprises the benzyl ester of the compound of formula (I) and fluoroxypyr MHE, wherein the weight ratio of the benzyl ester of the compound of formula (I) to fluoroxypyr MHE is about 1:35 to about 1:2. In one embodiment, the composition comprises the n-butyl ester of the compound of formula (I) and fluoroxypyr MHE, wherein the weight ratio of the n-butyl ester of the compound of formula (I) to fluoroxypyr MHE is about 1:17.5 to about 1:8.2. In one embodiment, the composition comprises the benzyl ester of the compound of formula (I) and fluoroxypyr, wherein the weight ratio of the benzyl ester of the compound of formula (I) to fluoroxypyr is about 1:4. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 37 grams acid equivalent per hectare (gae/ha) to about 860 gae/ha based on the total amount of active ingredients in the composition. In certain embodiments, the composition is applied at an application rate of from about 38 grams acid equivalent per hectare (gae/ha) to about 315 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and fluoroxypyr or carboxylate salt or ester thereof, e.g., sequentially or simultaneously. In some embodiments, the fluoroxypyr or carboxylate salt or ester thereof is applied at a rate from about 35 gae/ha to about 560 gae/ha and the compound of formula (I) of salt or ester thereof is applied at a rate from about 2 gae/ha to about 300 gae/ha. In some embodiments, the fluoroxypyr or carboxylate salt or ester thereof is applied at a rate from about 17 gae/ha to about 600 gae/ha and the compound of formula (I) of salt or ester thereof is applied at a rate from about 1 g acid equivalent per hectare (gae/ha) to about 70 gae/ha. In some embodiments, the fluoroxypyr or carboxylate salt or ester thereof is applied at a rate from about 35 gae/ha to about 280 gae/ha and the compound of formula (I) of salt or ester thereof is applied at a rate from about 2.2 g acid equivalent per hectare (gae/ha) to about 35 gae/ha. In some embodiments, the fluoroxypyr or carboxylate salt or ester thereof is applied at a rate from about 35 gae/ha to about 280 gae/ha and the compound of formula (I) of salt or ester thereof is applied at a rate from about 2.2 g acid equivalent per hectare (gae/ha) to about 64 gae/ha. In certain embodiments, the methods utilize the compound of formula (I), or its benzyl or n-butyl ester and fluoroxypyr or fluoroxypyr MHE. In one embodiment, the methods utilize the compound of formula (I) and fluoroxypyr MHE, wherein the compound of formula (I) is applied at a rate of from about 4.38 g acid equivalent per hectare (gae/ha) to about 64 gae/ha, and fluoroxypyr MHE is applied at a rate of about 70 gae/ha to about 280 gae/ha. In one embodiment, the methods utilize the benzyl ester of the compound of formula (I) and fluoroxypyr MHE, wherein the benzyl ester of the compound of formula (I) is applied at a rate of from about 2.2 g acid equivalent per hectare (gae/ha) to about 64 gae/ha, and fluoroxypyr MHE is applied at a rate of about 35 gae/ha to about 280 gae/ha. In one embodiment, the methods utilize the n-butyl ester of the compound of formula (I) and fluoroxypyr MHE, wherein the n-butyl ester of the compound of formula (I) is applied at a rate of about 16 g acid equivalent per hectare (gae/ha) to about 35 gae/ha, and fluoroxypyr MHE is applied at a rate of about 70 gae/ha to about 280 gae/ha. In one embodiment, the methods utilize the benzyl ester of the compound of formula (I) and fluoroxypyr, wherein the benzyl ester of the compound of formula (I) is applied at a rate of about 8.75 g acid equivalent per hectare (gae/ha) to about 64 gae/ha, and fluoroxypyr is applied at a rate of about 35 gae/ha to about 280 gae/ha. In certain embodiments, the methods and compositions utilizing the compound of formula (I) or salt or ester thereof in combination with fluoroxypyr or carboxylate salt or ester thereof are used to control SOOSS, CIRAR, CENMA, SONAR, TRFRE, ECHCG, ECHCO, CYPDI, LEFCH, ECHOR, SCPJU, SCPMA, AMARE, VIOTR, or POLCO.

In certain embodiments of the compositions and methods described herein, the compound of formula (I) or salt or ester thereof is used in combination with MCPA or carboxylate salt or ester thereof. With regard to the compositions, in some embodiments, the weight ratio of the compound of formula (I) or salt or ester thereof to MCPA or carboxylate salt or ester thereof is within the range of from about 1:850 to about 10:1. In certain embodiments, the weight ratio of the compound of formula (I) or salt or ester thereof to MCPA or carboxylate salt or ester thereof is within the range of from 1:509 to about 2:1. In certain embodiments, the weight ratio of the compound of formula (I) or salt or ester thereof to MCPA or carboxylate salt or ester thereof is within the range of from about 1:60 to about 1:1. In certain embodiments, the weight ratio of the compound of formula (I) or salt or ester thereof to MCPA or carboxylate salt or ester thereof is within the range of from about 1:28 to about 1:2. In certain embodiments, the compositions provided herein comprise the compound of formula (I) or its benzyl or n-butyl ester and MCPA, MCPA $K^+$, $Na^+$, DMA, or MCPA EHE. In one embodiment, the composition comprises the compound of formula (I) and MCPA K$^+$, Na$^+$, DMA, wherein the weight ratio of the compound of formula (I) to MCPA K$^+$, Na$^+$, DMA is about 1:28 to about 1:2. In one embodiment, the composition comprises the benzyl ester of the compound of formula (I) and MCPA K$^+$, Na$^+$, DMA, wherein the weight ratio of the benzyl ester of the compound of formula (I) to MCPA K$^+$, Na$^+$, DMA is about 1:28 to about 1:4. In one embodiment, the composition comprises the compound of formula (I) and MCPA EHE, wherein the weight ratio of the compound of formula (I) to MCPA EHE is about 1:6.6. In one embodiment, the composition comprises the benzyl ester of the compound of formula (I) and MCPA EHE, wherein the weight ratio of the benzyl ester of the compound of formula (I) to MCPA EHE is about 1:8. In one embodiment, the composition comprises the n-butyl ester of the compound of formula (I) and MCPA EHE, wherein the weight ratio of the n-butyl ester of the compound of formula (I) to MCPA EHE is about 1:17.5 to about 1:8. In one embodiment, the composition comprises the benzyl ester of the compound of formula (I) and MCPA, wherein the weight ratio of the benzyl ester of the compound of formula (I) to MCPA is about 1:16. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 32 grams acid equivalent per hectare (gae/ha) to about 2000 gae/ha based on the total amount of active ingredients in the composition. In certain embodiments, the composition is applied at an application rate of from about 33 grams acid equivalent per hectare (gae/ha) to about 1170 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and MCPA or carboxylate salt or ester thereof, e.g., sequentially or simultaneously. In some embodiments, the MCPA or carboxylate salt or ester thereof is applied at a rate from about 30 gae/ha to about 1700 gae/ha and the compound of formula (I) of salt or ester thereof is applied at a rate from about 2 gae/ha to about 300 gae/ha. In some embodiments, the MCPA or carboxylate salt or ester thereof is applied at a rate from about 35 gai/ha to about 600 gai/ha and the compound of formula (I) of salt or ester thereof is applied at a rate from about 2 g acid equivalent per hectare (gae/ha) to about 90 gae/ha. In some embodiments, the MCPA or carboxylate salt or ester thereof is applied at a rate from about 70 gai/ha to about 280 gai/ha and the compound of formula (I) of salt or ester thereof is applied at a rate from about 4.38 g acid equivalent per hectare (gae/ha) to about 42.4 gae/ha. In certain embodiments, the methods utilize the compound of formula (I), or its benzyl or n-butyl ester and MCPA, MCPA K$^+$, Na$^+$, DMA, or MCPA EHE. In one embodiment, the methods utilize the compound of formula (I) and MCPA K$^+$, Na$^+$, DMA, wherein the compound of formula (I) is applied at a rate of from about 4.38 g acid equivalent per hectare (gae/ha) to about 35 gae/ha, and MCPA K$^+$, Na$^+$, DMA is applied at a rate of about 70 gai/ha to about 140 gai/ha. In one embodiment, the methods utilize the benzyl ester of the compound of formula (I) and MCPA K$^+$, Na$^+$, DMA, wherein the benzyl ester of the compound of formula (I) is applied at a rate of from about 4.38 g acid equivalent per hectare (gae/ha) to about 17.5 gae/ha, and MCPA K$^+$, Na$^+$, DMA is applied at a rate of about 70 gai/ha to about 140 gai/ha. In one embodiment, the methods utilize the compound of formula (I) and MCPA EHE, wherein the compound of formula (I) is applied at a rate of about 42.4 g acid equivalent per hectare (gae/ha), and MCPA EHE is applied at a rate of about 280 gae/ha. In one embodiment, the methods utilize the benzyl ester of the compound of formula (I) and MCPA EHE, wherein the benzyl ester of the compound of formula (I) is applied at a rate of from about 35 g acid equivalent per hectare (gae/ha), and MCPA EHE is applied at a rate of about 280 gae/ha. In one embodiment, the methods utilize the n-butyl ester of the compound of formula (I) and MCPA EHE, wherein the n-butyl ester of the compound of formula (I) is applied at a rate of about 16 g acid equivalent per hectare (gae/ha) to about 35 gae/ha, and MCPA EHE is applied at a rate of about 280 gae/ha. In one embodiment, the methods utilize the benzyl ester of the compound of formula (I) and MCPA, wherein the benzyl ester of the compound of formula (I) is applied at a rate of about 8.75 g acid equivalent per hectare (gae/ha) to about 42 gae/ha, and MCPA is applied at a rate of about 70 gae/ha to about 280 gae/ha. In one embodiment, the methods utilize the benzyl ester of the compound of formula (I) and MCPA, wherein the benzyl ester of the compound of formula (I) is applied at a rate of about 8.75 g acid equivalent per hectare (gae/ha), and MCPA is applied at a rate of about 140 gae/ha. In certain embodiments, the methods and compositions utilizing the compound of formula (I) or salt or ester thereof in combination with MCPA or carboxylate salt or ester thereof are used to control DIGSA, ECHCG, LEFCH, BRAPP, ECHOR, SCPJU, VIOTR, POLCO, or BRSNN.

In certain embodiments of the compositions and methods described herein, the compound of formula (I) or salt or ester thereof is used in combination with mecoprop-P or carboxylate salt or ester thereof. With regard to the compositions, in some embodiments, the weight ratio of the compound of formula (I) or salt or ester thereof to mecoprop-P or carboxylate salt or ester thereof is within the range of from about 1:1680 to about 1.5:1. In certain embodiments, the weight ratio of the compound of formula (I) or salt or ester thereof to mecoprop-P or carboxylate salt or ester thereof is within the range of from 1:600 to about 1:4. In certain embodiments, the weight ratio of the compound of formula (I) or salt or ester thereof to mecoprop-P or carboxylate salt or ester thereof is within the range of from about 1:60 to about 1:7. In certain embodiments, the weight ratio of the compound of formula (I) or salt or ester thereof to mecoprop-P or carboxylate salt or ester thereof is within the range of from about 1:30 to about 1:15. In certain embodiments, the weight ratio of the compound of formula (I) or salt or ester thereof to mecoprop-P or carboxylate salt or ester thereof is about 1:22.9. In certain embodiments, the compositions provided herein comprise the compound of formula (I) or its benzyl ester and mecoprop-P. In one embodiment, the composition comprises the benzyl ester of the compound of formula (I) and mecoprop-P, wherein the weight ratio of the benzyl ester of the compound of formula (I) to mecoprop-P is about 1:22.9. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 202 grams acid equivalent per hectare (gae/ha) to about 3600 gae/ha based on the total amount of active ingredients in the composition. In certain embodiments, the composition is applied at an application rate of from about 204 grams acid equivalent per hectare (gae/ha) to about 1270 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and mecoprop-P or carboxylate salt or ester thereof, e.g., sequentially or simultaneously. In some embodiments, the mecoprop-P or carboxylate salt or ester thereof is applied at a rate from about 200 gae/ha to about 3360 gae/ha and the compound of formula (I) of salt or ester thereof is applied at a rate from about 2 gae/ha to about 300 gae/ha. In some embodiments, the mecoprop-P or carboxylate salt or ester thereof is applied at a rate from about 90 gai/ha to about 500 gai/ha and the compound of formula (I) of salt or ester thereof is applied at a rate from about 3 g acid equivalent per hectare (gae/ha) to about 24 gae/ha. In some embodiments, the mecoprop-P or carboxylate salt or ester thereof is applied at a rate from about 180 gai/ha to about 220 gai/ha and the compound of formula (I) of salt or ester thereof is applied at a rate from about 6 g acid equivalent per hectare (gae/ha) to about 12 gae/ha. In some embodiments, mecoprop-P or carboxylate salt or ester thereof is applied at a rate of about 200 gai/ha and the compound of formula (I) of salt or ester thereof is applied at a rate from about 8.75 g acid equivalent per hectare (gae/ha). In certain embodiments, the methods utilize the compound of formula (I), or its benzyl ester and mecoprop-P. In one embodiment, the methods utilize the benzyl ester of the compound of formula (I) and mecoprop-P, wherein the benzyl ester of the compound of formula (I) is applied at a rate of about 8.75 g acid equivalent per hectare (gae/ha), and mecoprop-P is applied at a rate of about 200 gai/ha. In certain embodiments, the methods and compositions utilizing the compound of formula (I) or salt or ester thereof in combination with mecoprop-P or carboxylate salt or ester thereof are used to control BRSNN.

In certain embodiments of the compositions and methods described herein, the compound of formula (I) or salt or ester thereof is used in combination with picloram or carboxylate salt or ester thereof. With regard to the compositions, in some embodiments, the weight ratio of the compound of formula (I) or salt or ester thereof to picloram or carboxylate salt or ester thereof is within the range of from about 1:560 to about 30:1. In certain embodiments, the weight ratio of the compound of formula (I) or salt or ester thereof to picloram or carboxylate salt or ester thereof is within the range of from 1:16 to about 1:1. In certain embodiments, the weight ratio of the compound of formula (I) or salt or ester thereof to picloram or carboxylate salt or ester thereof is within the range of from about 1:32 to about 2:1. In certain embodiments, the weight ratio of the compound of formula (I) or salt or ester thereof to picloram or carboxylate salt or ester thereof is within the range of from about 1:16 to about 1:1.1. In certain embodiments, the compositions provided herein comprise the compound of formula (I) or its benzyl ester and picloram or picloram K. In one embodiment, the composition comprises the benzyl ester of the compound of formula (I) and picloram, wherein the weight ratio of the benzyl ester of the compound of formula (I) to picloram is about 1:16 to about 1:2. In one embodiment, the composition comprises the benzyl ester of the compound of formula (I) and picloram $K^+$, wherein the weight ratio of the benzyl ester of the compound of formula (I) to picloram $K^+$ is about 1:1.1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 12 grams acid equivalent per hectare (gae/ha) to about 1420 gae/ha based on the total amount of active ingredients in the composition. In certain embodiments, the composition is applied at an application rate of from about 13 grams acid equivalent per hectare (gae/ha) to about 88 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and picloram or carboxylate salt or ester thereof, e.g., sequentially or simultaneously. In some embodiments, the picloram or carboxylate salt or ester thereof is applied at a rate from about 10 gae/ha to about 1120 gae/ha and the compound of formula (I) of salt or ester thereof is applied at a rate from about 2 gae/ha to about 300 gae/ha. In some embodiments, the picloram or carboxylate salt or ester thereof is applied at a rate from about 4 gai/ha to about 140 gai/ha and the compound of formula (I) of salt or ester thereof is applied at a rate from about 2 g acid equivalent per hectare (gae/ha) to about 45 gae/ha. In some embodiments, the picloram or carboxylate salt or ester thereof is applied at a rate from about 10 gai/ha to about 70 gai/ha and the compound of formula (I) of salt or ester thereof is applied at a rate from about 4.4 g acid equivalent per hectare (gae/ha) to about 17.5 gae/ha. In certain embodiments, the methods utilize the compound of formula (I), or its benzyl or n-butyl ester and picloram or picloram K. In one embodiment, the methods utilize the benzyl ester of the compound of formula (I) and picloram, wherein the benzyl ester of the compound of formula (I) is applied at a rate of from about 4.4 g acid equivalent per hectare (gae/ha) to about 17.5 gae/ha, and picloram is applied at a rate of about 10 gai/ha to about 70 gai/ha. In one embodiment, the methods utilize the benzyl ester of the compound of formula (I) and picloram $K^+$, wherein the benzyl ester of the compound of formula (I) is applied at a rate of about 8.75 g acid equivalent per hectare (gae/ha), and picloram $K^+$ is applied at a rate of about 10 gai/ha. In certain embodiments, the methods and compositions utilizing the compound of formula (I) or salt or ester thereof in combination with picloram or carboxylate salt or ester thereof are used to control CENMA, SINAR, VIOTR, STEME, or POLCO.

In certain embodiments of the compositions and methods described herein, the compound of formula (I) or salt or ester thereof is used in combination with quinclorac or carboxylate salt or ester thereof. With regard to the compositions, in some embodiments, the weight ratio of the compound of formula (I) or salt or ester thereof to quinclorac or carboxylate salt or ester thereof is within the range of from about 1:280 to about 4:1. In certain embodiments, the weight ratio of the compound of formula (I) or salt or ester thereof to quinclorac or carboxylate salt or ester thereof is within the range of from 1:127 to about 1:1. In certain embodiments, the weight ratio of the compound of formula (I) or salt or ester thereof to quinclorac or carboxylate salt or ester thereof is within the range of from about 1:130 to about 1:3. In certain embodiments, the weight ratio of the compound of formula (I) or salt or ester thereof to quinclorac or carboxylate salt or ester thereof is within the range of from about 1:64 to about 1:6.6. In certain embodiments, the compositions provided herein comprise the compound of formula (I) or its benzyl or n-butyl ester and quinclorac. In one embodiment, the composition comprises the compound of formula (I) and quinclorac, wherein the weight ratio of the compound of formula (I) to quinclorac is about 1:64 to about 1:6.6. In one embodiment, the composition comprises the benzyl ester of the compound of formula (I) and quinclorac, wherein the weight ratio of the benzyl ester of the compound of formula (I) to quinclorac is about 1:56 to about 1:8. In one embodiment, the composition comprises the n-butyl ester of the compound of formula (I) and quinclorac, wherein the weight ratio of the n-butyl ester of the compound of formula (I) to quinclorac is about 1:16 to about 1:8. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 72 grams acid equivalent per hectare (gae/ha) to about 860 gae/ha based on the total amount of active ingredients in the composition. In certain embodiments, the composition is applied at an application rate of from about 74 grams acid equivalent per hectare (gae/ha) to about 645 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and quinclorac or carboxylate salt or ester thereof, e.g., sequentially or simultaneously. In some embodiments, the quinclorac or carboxylate salt or ester thereof is applied at a rate from about 70 gae/ha to about 560 gae/ha and the compound of formula (I) of salt or ester thereof is applied at a rate from about 2 gae/ha to about 300 gae/ha. In some embodiments, the quinclorac or carboxylate salt or ester thereof is applied at a rate from about 35 gai/ha to about 1100 gai/ha and the compound of formula (I) of salt or ester thereof is applied at a rate from about 2 g acid equivalent per hectare (gae/ha) to about 170 gae/ha. In some embodiments, the quinclorac or carboxylate salt or ester thereof is applied at a rate from about 70 gai/ha to about 560 gai/ha and the compound of formula (I) of salt or ester thereof is applied at a rate from about 4.38 g acid equivalent per hectare (gae/ha) to about 84.8 gae/ha. In certain embodiments, the methods utilize the compound of formula (I), or its benzyl or n-butyl ester and quinclorac. In one embodiment, the methods utilize the compound of formula (I) and quinclorac, wherein the compound of formula (I) is applied at a rate of from about 4.38 g acid equivalent per hectare (gae/ha) to about 84.8 gae/ha, and quinclorac is applied at a rate of about 70 gai/ha to about 560 gai/ha. In one embodiment, the methods utilize the benzyl ester of the compound of formula (I) and quinclorac, wherein the benzyl ester of the compound of formula (I) is applied at a rate of from about 4.38 g acid equivalent per hectare (gae/ha) to about 35 gae/ha, and quinclorac is applied at a rate of about 70 gai/ha to about 560 gai/ha. In one embodiment, the methods utilize the n-butyl ester of the compound of formula (I) and quinclorac, wherein the n-butyl ester of the compound of formula (I) is applied at a rate of about 35 g acid equivalent per hectare (gae/ha) to about 70 gae/ha, and quinclorac is applied at a rate of about 560 gai/ha. In certain embodiments, the methods and compositions utilizing the compound of formula (I) or salt or ester thereof in combination with quinclorac or carboxylate salt or ester thereof are used to control CYPES, DIGSA, ECHCG, CYPIR ISCRU, ECHOR, SCPMA, AMARE, VIOTR, or POLCO.

In certain embodiments of the compositions and methods described herein, the compound of formula (I) or salt or ester thereof is used in combination with triclopyr or carboxylate salt or ester thereof. With regard to the compositions, in some embodiments, the weight ratio of the compound of formula (I) or salt or ester thereof to triclopyr or carboxylate salt or ester thereof is within the range of from about 1:1120 to about 4:1. In certain embodiments, the weight ratio of the compound of formula (I) or salt or ester thereof to triclopyr or carboxylate salt or ester thereof is within the range of from 1:64 to about 1:1. In certain embodiments, the weight ratio of the compound of formula (I) or salt or ester thereof to triclopyr or carboxylate salt or ester thereof is within the range of from about 1:100 to about 1:1. In certain embodiments, the weight ratio of the compound of formula (I) or salt or ester thereof to triclopyr or carboxylate salt or ester thereof is within the range of from about 1:44 to about 1:1.7. In certain embodiments, the compositions provided herein comprise the compound of formula (I) or its benzyl or n-butyl ester and triclopyr TEA, triclopyr choline, or triclopyr BEE. In one embodiment, the composition comprises the compound of formula (I) and triclopyr TEA, wherein the weight ratio of the compound of formula (I) to triclopyr TEA is about 1:44 to about 1:2. In one embodiment, the composition comprises the benzyl ester of the compound of formula (I) and triclopyr TEA, wherein the weight ratio of the benzyl ester of the compound of formula (I) to triclopyr TEA is about 1:44 to about 1:4. In one embodiment, the composition comprises the n-butyl ester of the compound of formula (I) and triclopyr TEA, wherein the weight ratio of the n-butyl ester of the compound of formula (I) to triclopyr TEA is about 1:17.5. In one embodiment, the composition comprises the compound of formula (I) and triclopyr choline, wherein the weight ratio of the compound of formula (I) to triclopyr choline is about 1:28 to about 1:1.7. In one embodiment, the composition comprises the benzyl ester of the compound of formula (I) and triclopyr choline, wherein the weight ratio of the benzyl ester of the compound of formula (I) to triclopyr choline is about 1:28 to about 1:4. In one embodiment, the composition comprises the benzyl ester of the compound of formula (I) and triclopyr BEE, wherein the weight ratio of the benzyl ester of the compound of formula (I) to triclopyr BEE is about 1:16 to about 1:2. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 37 grams acid equivalent per hectare (gae/ha) to about 2540 gae/ha based on the total amount of active ingredients in the composition. In certain embodiments, the composition is applied at an application rate of from about 40 grams acid equivalent per hectare (gae/ha) to about 325 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and triclopyr or carboxylate salt or ester thereof, e.g., sequentially or simultaneously. In some embodiments, the triclopyr or carboxylate salt or ester thereof is applied at a rate from about 35 gae/ha to about 2240 gae/ha and the compound of formula (I) of salt or ester thereof is applied at a rate from about 2 gae/ha to about 300 gae/ha. In some embodiments, the triclopyr salt or ester thereof is triclopyr TEA, triclopyr DMA or triclopyr choline salt. In some embodiments, the triclopyr or carboxylate salt or ester thereof is applied at a rate from about 17 gai/ha to about 600 gai/ha and the compound of formula (I) of salt or ester thereof is applied at a rate from about 2 g acid equivalent per hectare (gae/ha) to about 100 gae/ha. In some embodiments, the triclopyr or carboxylate salt or ester thereof is applied at a rate from about 35 gai/ha to about 280 gai/ha and the compound of formula (I) of salt or ester thereof is applied at a rate from about 4.38 g acid equivalent per hectare (gae/ha) to about 42.4 gae/ha. In certain embodiments, the methods utilize the compound of formula (I), or its benzyl or n-butyl ester and triclopyr TEA, triclopyr choline, or triclopyr BEE. In one embodiment, the methods utilize the compound of formula (I) and triclopyr TEA, wherein the compound of formula (I) is applied at a rate of from about 4.38 g acid equivalent per hectare (gae/ha) to about 42.4 gae/ha, and triclopyr TEA is applied at a rate of about 70 gai/ha to about 280 gai/ha. In one embodiment, the methods utilize the benzyl ester of the compound of formula (I) and triclopyr TEA, wherein the benzyl ester of the compound of formula (I) is applied at a rate of from about 4.38 g acid equivalent per hectare (gae/ha) to about 17.5 gae/ha, and triclopyr TEA is applied at a rate of about 70 gai/ha to about 280 gai/ha. In one embodiment, the methods utilize the n-butyl ester of the compound of formula (I) and triclopyr TEA, wherein the n-butyl ester of the compound of formula (I) is applied at a rate of about 16 g acid equivalent per hectare (gae/ha), and triclopyr TEA is applied at a rate of about 280 gai/ha. In one embodiment, the methods utilize the compound of formula (I) and triclopyr choline, wherein the compound of formula (I) is applied at a rate of from about 4.38 g acid equivalent per hectare (gae/ha) to about 42.4 gae/ha, and triclopyr choline is applied at a rate of about 35 gai/ha to about 140 gai/ha. In one embodiment, the methods utilize the benzyl ester of the compound of formula (I) and triclopyr choline, wherein the benzyl ester of the compound of formula (I) is applied at a rate of from about 4.38 g acid equivalent per hectare (gae/ha) to about 17.5 gae/ha, and triclopyr choline is applied at a rate of about 35 gai/ha to about 140 gai/ha. In one embodiment, the methods utilize the benzyl ester of the compound of formula (I) and triclopyr BEE, wherein the benzyl ester of the compound of formula (I) is applied at a rate of from about 4.4 g acid equivalent per hectare (gae/ha) to about 17.5 gae/ha, and triclopyr BEE is applied at a rate of about 35 gai/ha to about 70 gai/ha. In certain embodiments, the methods and compositions utilizing the compound of formula (I) or salt or ester thereof in combination with triclopyr or carboxylate salt or ester thereof are used to control BRAPP, DIGSA, ECHCG, ECHCO, LEFCH, SCPJU, SCPMA, ECHOR, CYPRO, FIMMI, CENMA, SONAR, CIRAR, or CASOB.

In certain embodiments of the compositions and methods described herein, the compound of formula (I) or salt or ester thereof is used in combination with halauxifen-methyl(methyl 4-amino-3-chloro-6-(4-chloro-2-fluoro-3-methoxyphenyl)picolinate) or carboxylic acid or carboxylate salt thereof or other ester. With regard to the compositions, in some embodiments, the weight ratio of the compound of formula (I) or salt or ester thereof to halauxifen-methyl or carboxylic acid or carboxylate salt thereof or other ester is within the range of from about 1:17.5 to about 600:1. In certain embodiments, the weight ratio of the compound of formula (I) or salt or ester thereof to halauxifen-methyl or carboxylic acid or carboxylate salt thereof or other ester is within the range of from 1:4 to about 20:1. In certain embodiments, the weight ratio of the compound of formula (I) or salt or ester thereof to halauxifen-methyl or carboxylic acid or carboxylate salt thereof or other ester is within the range of from about 1:4 to about 20:1. In certain embodiments, the weight ratio of the compound of formula (I) or salt or ester thereof to halauxifen-methyl or carboxylic acid or carboxylate salt thereof or other ester is within the range of from about 1:2 to about 9.6:1. In certain embodiments, the compositions provided herein comprise the compound of formula (I) or its benzyl ester and halauxifen-methyl or halauxifen K. In one embodiment, the composition comprises the compound of formula (I) and halauxifen-methyl, wherein the weight ratio of the compound of formula (I) to halauxifen-methyl is about 1:1 to about 9.6:1. In one embodiment, the composition comprises the benzyl ester of the compound of formula (I) and halauxifen-methyl, wherein the weight ratio of the benzyl ester of the compound of formula (I) to halauxifen-methyl is about 1:2 to about 8:1. In one embodiment, the composition comprises the benzyl ester of the compound of formula (I) and halauxifen K$^+$, wherein the weight ratio of the benzyl ester of the compound of formula (I) to halauxifen K$^+$ is about 1:2 to about 2:1. With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 2.5 grams acid equivalent per hectare (gae/ha) to about 335 gae/ha based on the total amount of active ingredients in the composition. In certain embodiments, the composition is applied at an application rate of from about 6 grams acid equivalent per hectare (gae/ha) to about 57 gae/ha based on the total amount of active ingredients in the composition. In some embodiments, the methods comprise contacting the undesirable vegetation or locus thereof or applying to the soil or water to prevent the emergence or growth of vegetation with a compound of formula (I) or salt or ester thereof and halauxifen-methyl or carboxylic acid or carboxylate salt thereof or other ester, e.g., sequentially or simultaneously. In some embodiments, halauxifen-methyl or carboxylic acid or carboxylate salt thereof or other ester is applied at a rate from about 0.5 gae/ha to about 35 gae/ha and the compound of formula (I) of salt or ester thereof is applied at a rate from about 2 gae/ha to about 300 gae/ha. In some embodiments, the halauxifen-methyl or carboxylic acid or carboxylate salt thereof or other ester is applied at a rate from about 1 gai/ha to about 30 gai/ha and the compound of formula (I) of salt or ester thereof is applied at a rate from about 1 g acid equivalent per hectare (gae/ha) to about 100 gae/ha. In some embodiments, the halauxifen-methyl or carboxylic acid or carboxylate salt thereof or other ester is applied at a rate from about 2.19 gai/ha to about 15 gai/ha and the compound of formula (I) of salt or ester thereof is applied at a rate from about 3.75 g acid equivalent per hectare (gae/ha) to about 42.4 gae/ha. In certain embodiments, the methods utilize the compound of formula (I), or its benzyl ester and halauxifen-methyl or halauxifen K$^+$. In one embodiment, the methods utilize the compound of formula (I) and halauxifen-methyl, wherein the compound of formula (I) is applied at a rate of from about 4.38 g acid equivalent per hectare (gae/ha) to about 42.4 gae/ha, and halauxifen-methyl is applied at a rate of about 2.19 gai/ha to about 8.75 gai/ha. In one embodiment, the methods utilize the benzyl ester of the compound of formula (I) and halauxifen-methyl, wherein the benzyl ester of the compound of formula (I) is applied at a rate of from about 3.75 g acid equivalent per hectare (gae/ha) to about 17.5 gae/ha, and halauxifen-methyl is applied at a rate of about 2.19 gai/ha to about 15 gai/ha. In one embodiment, the methods utilize the benzyl ester of the compound of formula (I) and halauxifen K$^+$, wherein the benzyl ester of the compound of formula (I) is applied at a rate of about 3.75 g acid equivalent per hectare (gae/ha) to about 42 gae/ha, and halauxifen K$^+$ is applied at a rate of about 3.75 gai/ha to about 15 gai/ha. In certain embodiments, the methods and compositions utilizing the compound of formula (I) or salt or ester thereof in combination with halauxifen-methyl or carboxylic acid or carboxylate salt thereof or other ester are used to control LEFCH, IPOHE, CYPIR, ECHCG, ECHOR, CYPRO, ELEIN, or SORHA.

The components of the mixtures described herein can be applied either separately or as part of a multipart herbicidal system.

The mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bialaphos, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, cloprop, cloproxydim, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dichlobenil, dichloralurea, dichlormate, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPB, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, SYN-523, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The compositions and methods described herein, can further be used in conjunction with glyphosate, 5-enolpyruvylshikimate-3-phosphate (EPSP) synthase inhibitors, glufosinate, glutamine synthetase inhibitors, dicamba, phenoxy auxins, pyridyloxy auxins, synthetic auxins, auxin transport inhibitors, aryloxyphenoxypropionates, cyclohexanediones, phenylpyrazolines, acetyl CoA carboxylase (ACCase) inhibitors, imidazolinones, sulfonylureas, pyrimidinylthiobenzoates, triazolopyrimidines, sulfonylaminocarbonyltriazolinones, acetolactate synthase (ALS) or acetohydroxy acid synthase (AHAS) inhibitors, 4-hydroxyphenyl-pyruvate dioxygenase (HPPD) inhibitors, phytoene desaturase inhibitors, carotenoid biosynthesis inhibitors, protoporphyrinogen oxidase (PPO) inhibitors, cellulose biosynthesis inhibitors, mitosis inhibitors, microtubule inhibitors, very long chain fatty acid inhibitors, fatty acid and lipid biosynthesis inhibitors, photosystem I inhibitors, photosystem II inhibitors, triazines, and bromoxynil on glyphosate-tolerant, EPSP synthase inhibitor-tolerant, glufosinate-tolerant, glutamine synthetase inhibitor-tolerant, dicamba-tolerant, phenoxy auxin-tolerant, pyridyloxy auxin-tolerant, auxin-tolerant, auxin transport inhibitor-tolerant, aryloxyphenoxypropionate-tolerant, cyclohexanedione-tolerant, phenylpyrazoline-tolerant, ACCase-tolerant, imidazolinone-tolerant, sulfonylurea-tolerant, pyrimidinylthiobenzoate-tolerant, triazolopyrimidine-tolerant, sulfonylaminocarbonyltriazolinone-tolerant, ALS- or AHAS-tolerant, HPPD-tolerant, phytoene desaturase inhibitor-tolerant, carotenoid biosynthesis inhibitor tolerant, PPO-tolerant, cellulose biosynthesis inhibitor-tolerant, mitosis inhibitor-tolerant, microtubule inhibitor-tolerant, very long chain fatty acid inhibitor-tolerant, fatty acid and lipid biosynthesis inhibitor-tolerant, photosystem I inhibitor-tolerant, photosystem II inhibitor-tolerant, triazine-tolerant, bromoxynil-tolerant, and crops possessing multiple or stacked traits conferring tolerance to multiple chemistries and/or multiple modes of action via single and/or multiple resistance mechanisms. In some embodiments, the compound of formula (I) or salt or ester thereof and complementary herbicide or salt or ester thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, corn, or maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, the compositions described herein are employed in combination with one or more plant growth regulators, such as 2,3,5-tri-iodobenzoic acid, IAA, IBA, naphthaleneacetamide, α-naphthaleneacetic acids, benzyladenine, 4-hydroxyphenethyl alcohol, kinetin, zeatin, endothal, ethephon, pentachlorophenol, thidiazuron, tribufos, aviglycine, ethephon, maleic hydrazide, gibberellins, gibberellic acid, abscisic acid, ancymidol, fosamine, glyphosine, isopyrimol, jasmonic acid, maleic hydrazide, mepiquat, 2,3,5-tri-iodobenzoic acid, morphactins, dichlorflurenol, flurprimidol, mefluidide, paclobutrazol, tetcyclacis, uniconazole, brassinolide, brassinolide-ethyl, cycloheximide, ethylene, methasulfocarb, prohexadione, triapenthenol and trinexapac.

In some embodiments, the plant growth regulators are employed in one or more crops or settings, such as rice, cereal crops, corn, maize, broadleaf crops, oilseed rape/canola, turf, pineapple, sugarcane, sunflower, pastures, grasslands, rangelands, fallowland, turf, tree and vine orchards, plantation crops, vegetables, and non-crop (ornamentals) settings. In some embodiments, the plant growth regulator is mixed with the compound of formula (I), or mixed with the compound of formula (I) and synthetic auxins to cause a preferentially advantageous effect on plants.

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG(400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, Water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiment's about 0.5 to 90 weight percent. Such compositions are, in certain embodiments, diluted with an inert carrier, such as water, before application. The diluted compositions usually applied to weeds or the locus of weeds contain, in certain embodiments, about 0.0006 to 3.0 weight percent active ingredient and in certain embodiments contain about 0.01 to 1.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Results in Examples I, II, III, IV, and V are greenhouse trial results.

Example I

Evaluation of Postemergence Foliar-Applied Herbicidal Mixtures for Weed Control in Direct Seeded Rice Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a volume of 1 quart and a surface area of 83.6 square centimeters ($cm^2$). When required to ensure good germination and healthy plants, a fungicide treatment and/or other chemical or physical treatment was applied. The plants were grown for 8-22 days in a greenhouse with an approximate 14 h photoperiod which was maintained at about 29° C. during the day and 26° C. during the night. Nutrients (Peters Excel® 15-5-15 5-Ca 2-Mg and iron chelate) were applied in the irrigation solution as needed and water was added on a regular basis. Supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl) pyridine-2-carboxylic acid (Compound A), each formulated as an SC (suspension concentrate), and various herbicidal components alone and in combination. Forms of compound A were applied on an acid equivalent basis.

Forms of Compound A (Compound of Formula I) Tested Include:

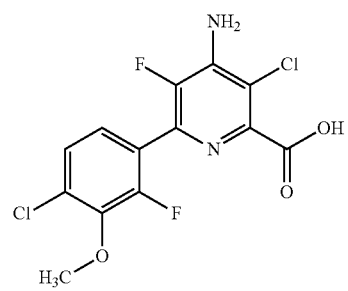

Compound A Acid

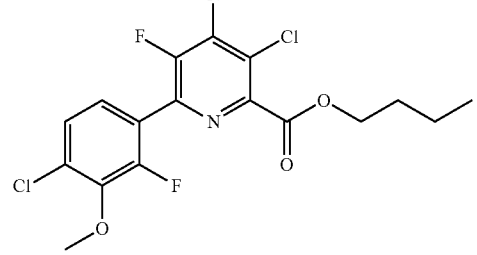

Compound A n-Butyl Ester

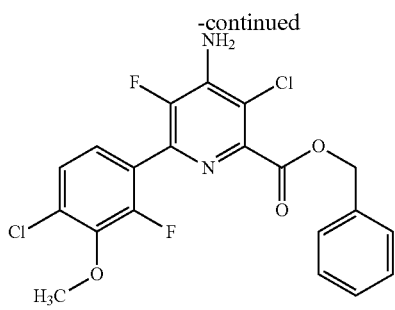

Compound A Benzyl Ester

Other herbicidal components were applied on an acid equivalent basis or active ingredient basis and included 2,4-D dimethylammonium (DMA) salt formulated as Weedar® 64, 2,4-D choline salt formulated as a soluble liquid (SL), 2,4-D 2-ethylhexyl ester (EHE) formulated as an SL, MCPA K+/Na+/DMA salt formulated as Agritox® 50, MCPA ethylhexyl ester formulated as MCPA2®, fluoroxypyr methylheptyl ester (MHE) formulated as Starane® or Starane® Ultra, triclopyr triethylamine (TEA) salt formulated as Grandstand® R, triclopyr choline salt formulated as an SL, triclopyr butotyl ester formulated as an EC, dicamba dimethylammonium (DMA) salt formulated as Banvel® 4S, quinclorac formulated as Facet® 75DF, and halauxifen-methyl formulated as an SC (suspension concentrate).

Treatment requirements were calculated based upon the rates being tested, the concentration of active ingredient or acid equivalent in the formulation, and a 12 mL application volume at a rate of 187 L/ha.

For treatments comprised of formulated compounds, measured amounts of compounds were placed individually in 25 mL glass vials and diluted in a volume of 1.25% (v/v) AgriDex® crop oil concentrated to obtain 12× stock solutions. If a test compound did not dissolve readily, the mixture was warmed and/or sonicated. Application solutions were prepared by adding an appropriate amount of each stock solution (e.g., 1 mL) and diluted to the appropriate final concentrations with the addition of 10 mL of an aqueous mixture of 1.25% (v/v) crop oil concentrate so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of 10 mL of an aqueous mixture of 1.5% (v/v) crop oil concentrate so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 12× stock solutions, and measured amounts of the formulated compounds can be placed individually in 25 mL glass vials and diluted in a volume of 1.5% (v/v) crop oil concentrate or water to obtain 12× stock solutions. If a test compound does not dissolve readily, the mixture can be warmed and/or sonicated. Application solutions can be prepared by adding an appropriate amount of each stock solution (e.g., 1 mL) and diluted to the appropriate final concentrations with the addition of an appropriate amount of an aqueous mixture of 1.5% (v/v) crop oil concentrate so that the final spray solutions contain 1.25% (v/v) crop oil concentrate. As required, additional water and/or 97:3 v/v acetone/DMSO can be added to individual application solutions so that the final acetone and DMSO concentrations of the application solutions being compared were 8.1% and 0.25%, respectively.

All stock solutions and applications solutions were visually inspected for compound compatibility prior to application. Spray solutions were applied to the plant material with an overhead Mandel track sprayer equipped with a 8002E nozzles calibrated to deliver 187 L/ha over an application area of 0.503 m² at a spray height of 18 to 20 inches (46 to 50 cm) above average plant canopy height. Control plants were sprayed in the same manner with the solvent blank.

The treated plants and control plants were placed in a greenhouse as described above and watered by sub-irrigation to prevent wash-off of the test compounds. After approximately 3 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 1-26.

TABLE 1

Synergistic Activity of Foliar-Applied Compound A Acid and 2,4-D Dimethylammonium (DMA) Salt Herbicidal Compositions on Weed Control in a Rice Cropping System.

| Compound A Acid | 2,4-D DMA Salt | Visual Weed Control (%) - 19 DAA ECHCG | |
|---|---|---|---|
| gae/ha | gae/ha | Obs | Exp |
| 4.38 | 0 | 60 | — |
| 0 | 70 | 0 | — |
| 0 | 140 | 10 | — |
| 0 | 280 | 25 | — |
| 4.38 | 70 | 75 | 60 |
| 4.38 | 140 | 75 | 64 |
| 4.38 | 280 | 75 | 70 |

TABLE 2

Synergistic Activity of Foliar-Applied Compound A Benzyl Ester and 2,4-D Dimethylammonium (DMA) Salt Herbicidal Compositions on Weed Control in a Rice Cropping System.

| Compound A Benzyl Ester | 2,4-D DMA Salt | Visual Weed Control (%) - 19 DAA ECHCG | |
|---|---|---|---|
| gae/ha | gae/ha | Obs | Exp |
| 4.38 | 0 | 55 | — |
| 0 | 70 | 0 | — |
| 0 | 140 | 10 | — |
| 0 | 280 | 25 | — |
| 4.38 | 70 | 70 | 55 |
| 4.38 | 140 | 80 | 60 |
| 4.38 | 280 | 70 | 66 |

TABLE 3

Synergistic Activity of Foliar-Applied Compound A Acid and 2,4-D Choline Salt Herbicidal Compositions on Weed Control in a Rice Cropping System.

| Compound A Acid | 2,4-D Choline Salt | Visual Weed Control (%) - 20 DAA | |
|---|---|---|---|
| gae/ha | gae/ha | Obs | Exp |
| | | DIGSA | |
| 4.38 | 0 | 30 | — |
| 17.5 | 0 | 40 | — |
| 0 | 105 | 0 | — |
| 0 | 210 | 0 | — |
| 0 | 420 | 10 | — |
| 4.38 | 105 | 40 | 30 |
| 17.5 | 105 | 70 | 40 |
| 4.38 | 210 | 50 | 30 |
| 17.5 | 210 | 75 | 40 |
| 4.38 | 420 | 50 | 37 |
| 17.5 | 420 | 65 | 46 |
| | | ECHCO | |
| 4.38 | 0 | 65 | — |
| 8.75 | 0 | 85 | — |
| 0 | 105 | 10 | — |
| 0 | 210 | 30 | — |
| 4.38 | 105 | 90 | 69 |
| 8.75 | 105 | 90 | 87 |
| 4.38 | 210 | 90 | 76 |
| 8.75 | 210 | 95 | 90 |
| | | CYPES | |
| 4.38 | 0 | 80 | — |
| 8.75 | 0 | 95 | — |
| 0 | 105 | 0 | — |
| 0 | 210 | 0 | — |
| 0 | 420 | 0 | — |
| 4.38 | 105 | 95 | 80 |
| 8.75 | 105 | 100 | 95 |
| 4.38 | 210 | 90 | 80 |
| 8.75 | 210 | 100 | 95 |
| 4.38 | 420 | 100 | 80 |
| 8.75 | 420 | 100 | 95 |
| | | CYPIR | |
| 4.38 | 0 | 40 | — |
| 0 | 105 | 50 | — |
| 0 | 210 | 100 | — |
| 0 | 420 | 70 | — |
| 4.38 | 105 | 100 | 70 |
| 4.38 | 210 | 100 | 100 |
| 4.38 | 420 | 100 | 82 |

TABLE 4

Synergistic Activity of Foliar-Applied Compound A Benzyl Ester and 2,4-D Choline Salt Herbicidal Compositions on Weed Control in a Rice Cropping System.

| Compound A Benzyl Ester | 2,4-D Choline Salt | Visual Weed Control (%) - 20 DAA | |
|---|---|---|---|
| gae/ha | gae/ha | Obs | Exp |
| | | DIGSA | |
| 4.38 | 0 | 50 | — |
| 8.75 | 0 | 60 | — |
| 17.5 | 0 | 70 | — |
| 0 | 420 | 10 | — |
| 4.38 | 420 | 65 | 55 |
| 8.75 | 420 | 70 | 64 |
| 17.5 | 420 | 99 | 73 |
| | | ECHCG | |
| 4.38 | 0 | 70 | — |
| 8.75 | 0 | 70 | — |
| 17.5 | 0 | 95 | — |
| 0 | 105 | 10 | — |
| 4.38 | 105 | 95 | 73 |
| 8.75 | 105 | 99 | 73 |
| 17.5 | 105 | 99 | 96 |
| | | ECHCO | |
| 4.38 | 0 | 60 | — |
| 8.75 | 0 | 85 | — |
| 0 | 105 | 10 | — |
| 0 | 210 | 30 | — |
| 4.38 | 105 | 85 | 64 |
| 8.75 | 105 | 90 | 87 |
| 4.38 | 210 | 85 | 72 |
| 8.75 | 210 | 95 | 90 |

TABLE 5

Synergistic Activity of Foliar-Applied Compound A Acid and 2,4-D Ethylhexyl ester (EHE) Herbicidal Compositions on Weed Control in a Rice Cropping System.

| Compound A Acid | 2,4-D EHE | Visual Weed Control (%) - 23 DAA | |
|---|---|---|---|
| gae/ha | gae/ha | Obs | Exp |
| | | BRAPP | |
| 4.38 | 0 | 40 | — |
| 8.75 | 0 | 55 | — |
| 0 | 70 | 0 | — |
| 0 | 140 | 0 | — |
| 0 | 280 | 0 | — |
| 4.38 | 70 | 55 | 40 |
| 8.75 | 70 | 65 | 55 |
| 4.38 | 140 | 55 | 40 |
| 8.75 | 140 | 65 | 55 |
| 4.38 | 280 | 60 | 40 |
| 8.75 | 280 | 70 | 55 |
| | | ECHCO | |
| 4.38 | 0 | 15 | — |
| 0 | 70 | 0 | — |
| 0 | 140 | 0 | — |
| 0 | 280 | 40 | — |
| 4.38 | 70 | 50 | 15 |
| 4.38 | 140 | 65 | 15 |
| 4.38 | 280 | 85 | 49 |

TABLE 5-continued

Synergistic Activity of Foliar-Applied Compound A Acid and 2,4-D Ethylhexyl ester (EHE) Herbicidal Compositions on Weed Control in a Rice Cropping System.

| Compound | | Visual Weed Control (%) - 23 DAA | | | |
|---|---|---|---|---|---|
| A Acid | 2,4-D EHE | DIGSA | | LEFCH | |
| gae/ha | gae/ha | Obs | Exp | Obs | Exp |
| 4.38 | 0 | 0 | — | 0 | — |
| 8.75 | 0 | 0 | — | 0 | — |
| 17.5 | 0 | 10 | — | 15 | — |
| 0 | 70 | 0 | — | 20 | — |
| 0 | 140 | 0 | — | 25 | — |
| 0 | 280 | 0 | — | 30 | — |
| 4.38 | 70 | 30 | 0 | 55 | 20 |
| 8.75 | 70 | 35 | 0 | 50 | 20 |
| 17.5 | 70 | 25 | 10 | 65 | 32 |
| 4.38 | 140 | 40 | 0 | 65 | 25 |
| 8.75 | 140 | 30 | 0 | 60 | 25 |
| 17.5 | 140 | 60 | 10 | 80 | 36 |
| 4.38 | 280 | 15 | 0 | 55 | 30 |
| 8.75 | 280 | 15 | 0 | 45 | 30 |
| 17.5 | 280 | 25 | 10 | 85 | 41 |

TABLE 6

Synergistic Activity of Foliar-Applied Compound A Benzyl Ester and 2,4-D Ethylhexyl ester (EHE) Herbicidal Compositions on Weed Control in a Rice Cropping System.

| Compound A Benzyl Ester | 2,4-D EHE | Visual Weed Control (%) - 23 DAA | | | |
|---|---|---|---|---|---|
| | | DIGSA | | ECHCO | |
| gae/ha | gae/ha | Obs | Exp | Obs | Exp |
| 4.38 | 0 | 0 | — | 40 | — |
| 8.75 | 0 | 0 | — | 40 | — |
| 17.5 | 0 | 15 | — | 75 | — |
| 0 | 70 | 0 | — | 0 | — |
| 0 | 140 | 0 | — | 0 | — |
| 0 | 280 | 0 | — | 40 | — |
| 4.38 | 70 | 20 | 0 | 50 | 40 |
| 8.75 | 70 | 25 | 0 | 65 | 40 |
| 17.5 | 70 | 35 | 15 | 70 | 75 |
| 4.38 | 140 | 25 | 0 | 55 | 40 |
| 8.75 | 140 | 25 | 0 | 75 | 40 |
| 17.5 | 140 | 35 | 15 | 85 | 75 |
| 4.38 | 280 | 60 | 0 | 60 | 64 |
| 8.75 | 280 | 40 | 0 | 80 | 64 |
| 17.5 | 280 | 60 | 15 | 100 | 85 |

| Compound A Benzyl Ester | 2,4-D EHE | Visual Weed Control (%) - 23 DAA | |
|---|---|---|---|
| gae/ha | gae/ha | Obs | Exp |
| | | LEFCH | |
| 4.38 | 0 | 20 | — |
| 8.75 | 0 | 20 | — |
| 17.5 | 0 | 45 | — |
| 0 | 70 | 20 | — |
| 0 | 280 | 30 | — |
| 4.38 | 70 | 75 | 36 |
| 8.75 | 70 | 80 | 36 |
| 17.5 | 70 | 55 | 56 |
| 4.38 | 280 | 70 | 44 |
| 8.75 | 280 | 80 | 44 |
| 17.5 | 280 | 80 | 62 |
| | | CYPES | |
| 4.38 | 0 | 85 | — |
| 0 | 70 | 0 | — |

TABLE 6-continued

Synergistic Activity of Foliar-Applied Compound A Benzyl Ester and 2,4-D Ethylhexyl ester (EHE) Herbicidal Compositions on Weed Control in a Rice Cropping System.

| 0 | 140 | 0 | — |
|---|---|---|---|
| 0 | 280 | 0 | — |
| 4.38 | 70 | 100 | 85 |
| 4.38 | 140 | 100 | 85 |
| 4.38 | 280 | 95 | 85 |

TABLE 7

Synergistic Activity of Foliar-Applied Compound A Acid and MCPA ($K^+$/$Na^+$/DMA Salt) Herbicidal Compositions on Weed Control in a Rice Cropping System.

| Compound A Acid | MCPA Salt | Visual Weed Control (%) - 21 DAA | |
|---|---|---|---|
| gae/ha | gai/ha | Obs | Exp |
| | | DIGSA | |
| 4.38 | 0 | 35 | — |
| 8.75 | 0 | 50 | — |
| 17.5 | 0 | 40 | — |
| 0 | 70 | 0 | — |
| 0 | 140 | 0 | — |
| 4.38 | 70 | 50 | 35 |
| 8.75 | 70 | 60 | 50 |
| 17.5 | 70 | 50 | 40 |
| 4.38 | 140 | 60 | 35 |
| 8.75 | 140 | 50 | 50 |
| 17.5 | 140 | 60 | 40 |
| | | ECHCG | |
| 4.38 | 0 | 15 | — |
| 8.75 | 0 | 50 | — |
| 0 | 70 | 0 | — |
| 0 | 140 | 0 | — |
| 4.38 | 70 | 75 | 15 |
| 8.75 | 70 | 70 | 50 |
| 4.38 | 140 | 65 | 15 |
| 8.75 | 140 | 70 | 50 |
| | | LEFCH | |
| 17.5 | 0 | 0 | — |
| 0 | 70 | 0 | — |
| 0 | 140 | 0 | — |
| 17.5 | 70 | 40 | 0 |
| 17.5 | 140 | 50 | 0 |

TABLE 8

Synergistic Activity of Foliar-Applied Compound A Benzyl Ester and MCPA ($K^+$/$Na^+$/DMA Salt) Herbicidal Compositions on Weed Control in a Rice Cropping System.

| Compound A Benzyl Ester | MCPA Salt | Visual Weed Control (%) - 21 DAA BRAPP | |
|---|---|---|---|
| gae/ha | gai/ha | Obs | Exp |
| 4.38 | 50 | 50 | — |
| 0 | 70 | 0 | — |
| 0 | 140 | 0 | — |
| 4.38 | 70 | 65 | 50 |
| 4.38 | 140 | 65 | 50 |

TABLE 8-continued

Synergistic Activity of Foliar-Applied Compound A Benzyl Ester and MCPA (K+/Na+/DMA Salt) Herbicidal Compositions on Weed Control in a Rice Cropping System.

| Compound A Benzyl Ester | MCPA Salt | Visual Weed Control (%) - 21 DAA | | | |
|---|---|---|---|---|---|
| | | DIGSA | | ECHCG | |
| gae/ha | gai/ha | Obs | Exp | Obs | Exp |
| 4.38 | 0 | 50 | — | 10 | — |
| 8.75 | 0 | 35 | — | 85 | — |
| 0 | 70 | 0 | — | 0 | — |
| 0 | 140 | 0 | — | 0 | — |
| 4.38 | 70 | 60 | 50 | 80 | 10 |
| 8.75 | 70 | 50 | 35 | 90 | 85 |
| 4.38 | 140 | 50 | 50 | 70 | 10 |
| 8.75 | 140 | 60 | 35 | 85 | 85 |

TABLE 9

Synergistic Activity of Foliar-Applied Compound A Benzyl Ester and MCPA Ethylhexyl ester (EHE) Herbicidal Compositions on Weed Control in a Rice Cropping System

| Compound A Benzyl Ester | MCPA EHE | Visual Weed Control (%) - 22 DAA | | | | | |
|---|---|---|---|---|---|---|---|
| | | DIGSA | | ECHCG | | LEFCH | |
| gae/ha | gai/ha | Obs | Exp | Obs | Exp | Obs | Exp |
| 8 | 0 | 10 | — | 35 | — | 15 | — |
| 16 | 0 | 15 | — | 65 | — | 50 | — |
| 32 | 0 | 30 | — | 80 | — | 60 | — |
| 0 | 70 | 0 | — | 0 | — | 0 | — |
| 0 | 140 | 0 | — | 0 | — | 0 | — |
| 0 | 280 | 0 | — | 0 | — | 0 | — |
| 8 | 70 | 10 | 10 | 60 | 35 | 30 | 15 |
| 16 | 70 | 30 | 15 | 85 | 65 | 70 | 50 |
| 32 | 70 | 50 | 30 | 95 | 80 | 75 | 60 |
| 8 | 140 | 15 | 10 | 80 | 35 | 30 | 15 |
| 16 | 140 | 25 | 15 | 90 | 65 | 55 | 50 |
| 32 | 140 | 40 | 30 | 95 | 80 | 65 | 60 |
| 8 | 280 | 40 | 10 | 65 | 35 | 40 | 15 |
| 16 | 280 | 50 | 15 | 90 | 65 | 70 | 50 |
| 32 | 280 | 55 | 30 | 95 | 80 | 75 | 60 |

TABLE 10

Synergistic Activity of Foliar-Applied Compound A n-Butyl Ester and MCPA Ethylhexyl ester (EHE) Herbicidal Compositions on Weed Control in a Rice Cropping System.

| Compound A n-Butyl Ester | MCPA EHE | Visual Weed Control (%) - 20 DAA | | | |
|---|---|---|---|---|---|
| | | DIGSA | | ECHCG | |
| gae/ha | gai/ha | Obs | Exp | Obs | Exp |
| 16 | 0 | 15 | — | 65 | — |
| 0 | 280 | 20 | — | 40 | — |
| 16 | 280 | 45 | 32 | 97 | 79 |

TABLE 11

Synergistic Activity of Foliar-Applied Compound A Acid and Triclopyr Triethylamine (TEA) Salt Herbicidal Compositions on Weed Control in a Rice Cropping System.

| Compound A Acid | Triclopyr TEA Salt | Visual Weed Control (%) - 21 DAA | |
|---|---|---|---|
| gae/ha | gae/ha | Obs | Exp |
| | | BRAPP | |
| 4.38 | 0 | 50 | — |
| 0 | 98.3 | 0 | — |
| 0 | 196.6 | 0 | — |
| 4.38 | 98.3 | 80 | 50 |
| 4.38 | 196.6 | 65 | 50 |
| | | DIGSA | |
| 4.38 | 0 | 35 | — |
| 8.75 | 0 | 50 | — |
| 17.5 | 0 | 40 | — |
| 0 | 98.3 | 0 | — |
| 4.38 | 98.3 | 60 | 35 |
| 8.75 | 98.3 | 65 | 50 |
| 17.5 | 98.3 | 65 | 40 |

| Compound A Acid | Triclopyr TEA Salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 15 | — | 70 | — |
| 8.75 | 0 | 50 | — | 75 | — |
| 0 | 98.3 | 30 | — | 0 | — |
| 0 | 196.6 | 20 | — | 0 | — |
| 4.38 | 98.3 | 65 | 41 | 70 | 70 |
| 8.75 | 98.3 | 95 | 65 | 85 | 75 |
| 4.38 | 196.6 | 90 | 32 | 90 | 70 |
| 8.75 | 196.6 | 95 | 60 | 90 | 75 |

| Compound A Acid | Triclopyr TEA Salt | Visual Weed Control (%) - 21 DAA | |
|---|---|---|---|
| | | LEFCH | |
| gae/ha | gae/ha | Obs | Exp |
| 8.75 | 0 | 0 | — |
| 17.5 | 0 | 0 | — |
| 0 | 196.6 | 0 | — |
| 8.75 | 196.6 | 20 | 0 |
| 17.5 | 196.6 | 35 | 0 |

| Compound A Acid | Triclopyr TEA Salt | Visual Weed Control (%) - 19 DAA | |
|---|---|---|---|
| | | LEFCH | |
| gae/ha | gae/ha | Obs | Exp |
| 19.4 | 0 | 5 | — |
| 0 | 280 | 20 | — |
| 19.4 | 280 | 60 | 24 |

TABLE 12

Synergistic Activity of Foliar-Applied Compound A Benzyl Ester and Triclopyr Triethylamine (TEA) Salt Herbicidal Compositions on Weed Control in a Rice Cropping System.

| Compound A Benzyl Ester | Triclopyr TEA Salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 10 | — | 70 | — |
| 8.75 | 0 | 85 | — | 75 | — |
| 0 | 98.3 | 30 | — | 0 | — |
| 0 | 196.6 | 20 | — | 0 | — |
| 4.38 | 98.3 | 65 | 37 | 85 | 70 |
| 8.75 | 98.3 | 95 | 90 | 90 | 75 |
| 4.38 | 196.6 | 70 | 28 | 85 | 70 |
| 8.75 | 196.6 | 90 | 88 | 85 | 75 |

| Compound A Benzyl Ester | Triclopyr TEA Salt | Visual Weed Control (%) - 19 DAA | |
|---|---|---|---|
| | | DIGSA | |
| gae/ha | gae/ha | Obs | Exp |
| 16 | 0 | 18 | — |
| 0 | 280 | 55 | — |
| 16 | 280 | 78 | 63 |

TABLE 13

Synergistic Activity of Foliar-Applied Compound A n-Butyl Ester and Triclopyr Triethylamine (TEA) Salt Herbicidal Compositions on Weed Control in a Rice Cropping System.

| Compound A n-Butyl TEA Salt | Triclopyr Ester | Visual Weed Control (%) - 19 DAA | |
|---|---|---|---|
| | | LEFCH | |
| gae/ha | gae/ha | Obs | Exp |
| 16 | 0 | 10 | — |
| 0 | 280 | 20 | — |
| 16 | 280 | 68 | 28 |

TABLE 14

Synergistic Activity of Foliar-Applied Compound A Acid and Triclopyr Choline Salt Herbicidal Compositions on Weed Control in a Rice Cropping System.

| Compound A Acid | Triclopyr Choline Salt | Visual Weed Control (%) - 21 DAA | |
|---|---|---|---|
| | | ECHCG | |
| gae/ha | gae/ha | Obs | Exp |
| 5.3 | 0 | 65 | — |
| 10.6 | 0 | 55 | — |
| 0 | 35 | 0 | — |
| 0 | 70 | 0 | — |
| 0 | 140 | 0 | — |
| 5.3 | 35 | 55 | 65 |
| 10.6 | 35 | 70 | 55 |
| 5.3 | 70 | 70 | 65 |
| 10.6 | 70 | 55 | 55 |
| 5.3 | 140 | 80 | 65 |
| 10.6 | 140 | 60 | 55 |

| Compound A Acid | Triclopyr Choline Salt | Visual Weed Control (%) - 21 DAA | | | |
|---|---|---|---|---|---|
| | | DIGSA | | LEFCH | |
| gae/ha | gae/ha | Obs | Exp | Obs | Exp |
| 5.3 | 0 | 10 | — | 0 | — |
| 10.6 | 0 | 10 | — | 10 | — |
| 21.2 | 0 | 15 | — | 10 | — |
| 0 | 35 | 0 | — | 0 | — |
| 0 | 70 | 10 | — | 20 | — |
| 0 | 140 | 20 | — | 0 | — |
| 5.3 | 35 | 20 | 10 | 15 | 0 |
| 10.6 | 35 | 30 | 10 | 30 | 10 |
| 21.2 | 35 | 40 | 15 | 80 | 10 |
| 5.3 | 70 | 10 | 19 | 20 | 20 |
| 10.6 | 70 | 60 | 19 | 25 | 28 |
| 21.2 | 70 | 75 | 24 | 60 | 28 |
| 5.3 | 140 | 55 | 28 | 20 | 0 |
| 10.6 | 140 | 50 | 28 | 20 | 10 |
| 21.2 | 140 | 60 | 32 | 60 | 10 |

| Compound A Acid | Triclopyr Choline Salt | Visual Weed Control (%) - 21 DAA | |
|---|---|---|---|
| | | SCPJU | |
| gae/ha | gae/ha | Obs | Exp |
| 5.3 | 0 | 60 | — |
| 10.6 | 0 | 75 | — |
| 0 | 35 | 0 | — |
| 0 | 70 | 50 | — |
| 5.3 | 35 | 99 | 60 |
| 10.6 | 35 | 100 | 75 |
| 5.3 | 70 | 99 | 80 |
| 10.6 | 70 | 99 | 88 |

TABLE 15

Synergistic Activity of Foliar-Applied Compound A Benzyl Ester and Triclopyr Choline Salt Herbicidal Compositions on Weed Control in a Rice Cropping System.

| Compound A Benzyl Ester | Triclopyr Choline Salt | Visual Weed Control (%) - 21 DAA | | | |
|---|---|---|---|---|---|
| | | ECHCG | | ECHCO | |
| gae/ha | gae/ha | Obs | Exp | Obs | Exp |
| 4.38 | 0 | 40 | — | 30 | — |
| 8.75 | 0 | 60 | — | 55 | — |
| 0 | 35 | 0 | — | 0 | — |
| 0 | 70 | 0 | — | 0 | — |
| 0 | 140 | 0 | — | 0 | — |
| 4.38 | 35 | 60 | 40 | 50 | 30 |
| 8.75 | 35 | 60 | 60 | 60 | 55 |
| 4.38 | 70 | 45 | 40 | 75 | 30 |
| 8.75 | 70 | 85 | 60 | 70 | 55 |
| 4.38 | 140 | 40 | 40 | 60 | 30 |
| 8.75 | 140 | 75 | 60 | 80 | 55 |

| Compound A Benzyl Ester | Triclopyr Choline Salt | Visual Weed Control (%) - 21 DAA | |
|---|---|---|---|
| | | DIGSA | |
| gae/ha | gae/ha | Obs | Exp |
| 4.38 | 0 | 10 | — |
| 0 | 35 | 0 | — |
| 0 | 70 | 10 | — |

TABLE 15-continued

Synergistic Activity of Foliar-Applied Compound A Benzyl Ester and Triclopyr Choline Salt Herbicidal Compositions on Weed Control in a Rice Cropping System.

| | | | |
|---|---|---|---|
| 0 | 140 | 20 | — |
| 4.38 | 35 | 10 | 10 |
| 4.38 | 70 | 30 | 19 |
| 4.38 | 140 | 45 | 28 |
| | | SCPJU | |
| 4.38 | 0 | 40 | — |
| 0 | 35 | 0 | — |
| 0 | 70 | 50 | — |
| 4.38 | 35 | 95 | 40 |
| 4.38 | 70 | 95 | 70 |

TABLE 16

Synergistic Activity of Foliar-Applied Compound A Acid and Triclopyr Butotyl Ester Herbicidal Compositions on Weed Control in a Rice Cropping System.

| Compound A Acid | Triclopyr Butotyl Ester | Visual Weed Control (%) - 23 DAA BRAPP | |
|---|---|---|---|
| gae/ha | gae/ha | Obs | Exp |
| 4.38 | 0 | 40 | — |
| 8.75 | 0 | 55 | — |
| 17.5 | 0 | 80 | — |
| 0 | 35 | 0 | — |
| 0 | 70 | 0 | — |
| 4.38 | 35 | 50 | 40 |
| 8.75 | 35 | 70 | 55 |
| 17.5 | 35 | 85 | 80 |
| 4.38 | 70 | 65 | 40 |
| 8.75 | 70 | 80 | 55 |
| 17.5 | 70 | 100 | 80 |

| Compound A Acid | Triclopyr Butotyl Ester | Visual Weed Control (%) - 23 DAA | | | |
|---|---|---|---|---|---|
| | | DIGSA | | ECHCO | |
| gae/ha | gae/ha | Obs | Exp | Obs | Exp |
| 4.38 | 0 | 0 | — | 15 | — |
| 8.75 | 0 | 0 | — | 60 | — |
| 17.5 | 0 | 10 | — | 80 | — |
| 0 | 35 | 0 | — | 0 | — |
| 0 | 70 | 0 | — | 0 | — |
| 0 | 140 | 0 | — | 0 | — |
| 4.38 | 35 | 40 | 0 | 40 | 15 |
| 8.75 | 35 | 40 | 0 | 65 | 60 |
| 17.5 | 35 | 40 | 10 | 85 | 80 |
| 4.38 | 70 | 40 | 0 | 40 | 15 |
| 8.75 | 70 | 50 | 0 | 75 | 60 |
| 17.5 | 70 | 45 | 10 | 90 | 80 |
| 4.38 | 140 | 60 | 0 | 45 | 15 |
| 8.75 | 140 | 60 | 0 | 65 | 60 |
| 17.5 | 140 | 50 | 10 | 95 | 80 |

| Compound A Acid | Triclopyr Butotyl Ester | Visual Weed Control (%) - 23 DAA ECHCG | |
|---|---|---|---|
| gae/ha | gae/ha | Obs | Exp |
| 4.38 | 0 | 45 | — |
| 8.75 | 0 | 55 | — |
| 0 | 35 | 0 | — |
| 0 | 70 | 0 | — |
| 0 | 140 | 15 | — |
| 4.38 | 35 | 45 | 45 |
| 8.75 | 35 | 70 | 55 |

TABLE 16-continued

Synergistic Activity of Foliar-Applied Compound A Acid and Triclopyr Butotyl Ester Herbicidal Compositions on Weed Control in a Rice Cropping System.

| | | | |
|---|---|---|---|
| 4.38 | 70 | 55 | 45 |
| 8.75 | 70 | 65 | 55 |
| 4.38 | 140 | 65 | 53 |
| 8.75 | 140 | 65 | 62 |

TABLE 17

Synergistic Activity of Foliar-Applied Compound A Benzyl Ester and Triclopyr Butotyl Ester Herbicidal Compositions on Weed Control in a Rice Cropping System.

| Compound A Benzyl Ester | Triclopyr Butotyl Ester | Visual Weed Control (%) - 23 DAA DIGSA | |
|---|---|---|---|
| gae/ha | gae/ha | Obs | Exp |
| 4.38 | 0 | 0 | — |
| 8.75 | 0 | 0 | — |
| 17.5 | 0 | 15 | — |
| 0 | 35 | 0 | — |
| 0 | 70 | 0 | — |
| 0 | 140 | 0 | — |
| 4.38 | 35 | 40 | 0 |
| 8.75 | 35 | 40 | 0 |
| 17.5 | 35 | 25 | 15 |
| 4.38 | 70 | 25 | 0 |
| 8.75 | 70 | 50 | 0 |
| 17.5 | 70 | 25 | 15 |
| 4.38 | 140 | 20 | 0 |
| 8.75 | 140 | 60 | 0 |
| 17.5 | 140 | 30 | 15 |

| Compound A Benzyl Ester | Triclopyr Butotyl Ester | Visual Weed Control (%) - 23 DAA ECHCG | |
|---|---|---|---|
| gae/ha | gae/ha | Obs | Exp |
| 4.38 | 0 | 40 | — |
| 8.75 | 0 | 55 | — |
| 0 | 35 | 0 | — |
| 0 | 70 | 0 | — |
| 0 | 140 | 15 | — |
| 4.38 | 35 | 45 | 40 |
| 8.75 | 35 | 70 | 55 |
| 4.38 | 70 | 40 | 40 |
| 8.75 | 70 | 60 | 55 |
| 4.38 | 140 | 65 | 49 |
| 8.75 | 140 | 65 | 62 |

| Compound A Benzyl Ester | Triclopyr Butotyl Ester | Visual Weed Control (%) - 23 DAA ECHCO | |
|---|---|---|---|
| gae/ha | gae/ha | Obs | Exp |
| 4.38 | 0 | 40 | — |
| 8.75 | 0 | 40 | — |
| 17.5 | 0 | 75 | — |
| 0 | 70 | 0 | — |
| 0 | 140 | 0 | — |
| 4.38 | 70 | 45 | 40 |
| 8.75 | 70 | 80 | 40 |
| 17.5 | 70 | 90 | 75 |
| 4.38 | 140 | 60 | 40 |
| 8.75 | 140 | 70 | 40 |
| 17.5 | 140 | 70 | 75 |

TABLE 18

Synergistic Activity of Foliar-Applied Compound A Acid and Fluroxypyr Methylheptyl Ester (MHE) Herbicidal Compositions on Weed Control in a Rice Cropping System.

| Compound A Acid | Fluroxypyr MHE | Visual Weed Control (%) - 21 DAA | | | | | |
|---|---|---|---|---|---|---|---|
| | | ECHCG | | ECHCO | | CYPDI | |
| gae/ha | gae/ha | Obs | Exp | Obs | Exp | Obs | Exp |
| 4.38 | 0 | 15 | — | 70 | — | 50 | — |
| 8.75 | 0 | 50 | — | 75 | — | 85 | — |
| 0 | 70 | 0 | — | 0 | — | 15 | — |
| 0 | 140 | 0 | — | 0 | — | 80 | — |
| 4.38 | 70 | 70 | 15 | 60 | 70 | 100 | 58 |
| 8.75 | 70 | 95 | 50 | 90 | 75 | 100 | 87 |
| 4.38 | 140 | 90 | 15 | 85 | 70 | 100 | 90 |
| 8.75 | 140 | 95 | 50 | 95 | 75 | 100 | 97 |

| Compound A Acid | Fluroxypyr MHE | Visual Weed Control (%) - 19 DAA | | | |
|---|---|---|---|---|---|
| | | ECHCG | | LEFCH | |
| gae/ha | gae/ha | Obs | Exp | Obs | Exp |
| 19.4 | 0 | 80 | — | 5 | — |
| 0 | 280 | 25 | — | 28 | — |
| 19.4 | 280 | 97 | 85 | 75 | 31 |

TABLE 19

Synergistic Activity of Foliar-Applied Compound A Benzyl Ester and Fluroxypyr Methylheptyl Ester (MHE) Herbicidal Compositions on Weed Control in a Rice Cropping System.

| Compound A Benzyl Ester | Fluroxypyr MHE | Visual Weed Control (%) - 21 DAA | | | |
|---|---|---|---|---|---|
| | | ECHCG | | ECHCO | |
| gae/ha | gae/ha | Obs | Exp | Obs | Exp |
| — | 0 | 10 | — | 70 | — |
| — | 0 | 85 | — | 75 | — |
| — | 70 | 0 | — | 0 | — |
| — | 140 | 0 | — | 0 | — |
| 4.38 | 70 | 60 | 10 | 85 | 70 |
| 8.75 | 70 | 95 | 85 | 95 | 75 |
| 4.38 | 140 | 85 | 10 | 90 | 70 |
| 8.75 | 140 | 95 | 85 | 90 | 75 |

| Compound A Benzyl Ester | Fluroxypyr MHE | Visual Weed Control (%) - 19 DAA LEFCH | |
|---|---|---|---|
| gae/ha | gae/ha | Obs | Exp |
| 16 | 0 | 58 | — |
| 0 | 280 | 28 | — |
| 16 | 280 | 83 | 69 |

TABLE 20

Synergistic Activity of Foliar-Applied Compound A n-Butyl Ester and Fluroxypyr Methylheptyl Ester (MHE) Herbicidal Compositions on Weed Control in a Rice Cropping System.

| Compound A n-Butyl Ester | Fluroxypyr MHE | Visual Weed Control (%) - 19 DAA ECHCG | |
|---|---|---|---|
| gae/ha | gae/ha | Obs | Exp |
| 16 | 0 | 65 | — |
| 0 | 280 | 25 | — |
| 16 | 280 | 95 | 74 |

TABLE 21

Synergistic Activity of Foliar-Applied Compound A Acid and Dicamba Dimethylammonium (DMA) Salt Herbicidal Compositions on Control of Weeds Common to Rice Cropping Systems.

| Compound A Acid | Dicamba DMA Salt | Visual Weed Control (%) - 20 DAA | | | |
|---|---|---|---|---|---|
| | | LEFCH | | CYPIR | |
| gae/ha | gae/ha | Obs | Exp | Obs | Exp |
| 5.3 | 0 | 10 | — | 65 | — |
| 0 | 140 | 0 | — | 0 | — |
| 0 | 280 | 0 | — | 35 | — |
| 5.3 | 140 | 25 | 10 | 90 | 65 |
| 5.3 | 280 | 25 | 10 | 100 | 77 |

TABLE 22

Synergistic Activity of Foliar-Applied Compound A Benzyl Ester and Dicamba Dimethylammonium (DMA) Salt Herbicidal Compositions on Control of Weeds Common to Rice Cropping Systems.

| Compound A Benzyl Ester | Dicamba DMA Salt | Visual Weed Control (%) - 20 DAA | | | |
|---|---|---|---|---|---|
| | | ECHCO | | CYPIR | |
| gae/ha | gae/ha | Obs | Exp | Obs | Exp |
| 4.38 | 0 | 50 | — | 35 | — |
| 8.75 | 0 | 75 | — | 35 | — |
| 0 | 70 | 0 | — | 0 | — |
| 0 | 140 | 0 | — | 0 | — |
| 0 | 280 | 0 | — | 35 | — |
| 4.38 | 70 | 70 | 50 | 80 | 35 |
| 8.75 | 70 | 75 | 75 | 100 | 35 |
| 4.38 | 140 | 55 | 50 | 65 | 35 |
| 8.75 | 140 | 75 | 75 | 100 | 35 |
| 4.38 | 280 | 70 | 50 | 50 | 58 |
| 8.75 | 280 | 95 | 75 | 95 | 58 |

TABLE 23

Synergistic Activity of Foliar-Applied Compound A Acid and Halauxifen-Methyl Ester Herbicidal Compositions on Weed Control in a Rice Cropping System.

| Compound A Acid | Halauxifen-Methyl Ester | Visual Weed Control (%) - 20 DAA | | | |
|---|---|---|---|---|---|
| | | LEFCH | | IPOHE | |
| gae/ha | gae/ha | Obs | Exp | Obs | Exp |
| 4.38 | 0 | 0 | — | 10 | — |
| 8.75 | 0 | 0 | — | 15 | — |

TABLE 23-continued

Synergistic Activity of Foliar-Applied Compound A Acid and Halauxifen-Methyl Ester Herbicidal Compositions on Weed Control in a Rice Cropping System.

| Compound A Acid | Halauxifen-Methyl Ester | Visual Weed Control (%) - 20 DAA | | | |
|---|---|---|---|---|---|
| | | LEFCH | | IPOHE | |
| gae/ha | gae/ha | Obs | Exp | Obs | Exp |
| 17.5 | 0 | 10 | — | 30 | — |
| 0 | 2.19 | 0 | — | 0 | — |
| 0 | 4.38 | 10 | — | 0 | — |
| 4.38 | 2.19 | 30 | 0 | 45 | 10 |
| 8.75 | 2.19 | 20 | 0 | 50 | 15 |
| 17.5 | 2.19 | 50 | 10 | 55 | 30 |
| 4.38 | 4.38 | 30 | 10 | 30 | 10 |
| 8.75 | 4.38 | 35 | 10 | 40 | 15 |
| 17.5 | 4.38 | 40 | 19 | 25 | 30 |

TABLE 24

Synergistic Activity of Foliar-Applied Compound A Benzyl Ester and Halauxifen-Methyl Ester Herbicidal Compositions on Weed Control in a Rice Cropping System.

| Compound A Benzyl Ester | Halauxifen-Methyl Ester | Visual Weed Control (%) - 20 DAA LEFCH | |
|---|---|---|---|
| gae/ha | gae/ha | Obs | Exp |
| 4.38 | 0 | 0 | — |
| 8.75 | 0 | 20 | — |
| 0 | 2.19 | 0 | — |
| 0 | 4.38 | 10 | — |
| 4.38 | 2.19 | 30 | 0 |
| 8.75 | 2.19 | 30 | 20 |
| 4.38 | 4.38 | 45 | 10 |
| 8.75 | 4.38 | 45 | 28 |

| Compound A Benzyl Ester | Halauxifen-Methyl Ester | Visual Weed Control (%) - 20 DAA CYPIR | |
|---|---|---|---|
| gae/ha | gae/ha | Obs | Exp |
| 4.38 | 0 | 15 | — |
| 0 | 2.19 | 25 | — |
| 0 | 4.38 | 70 | — |
| 4.38 | 2.19 | 85 | 36 |
| 4.38 | 4.38 | 90 | 75 |

| Compound A Benzyl Ester | Halauxifen-Methyl Ester | Visual Weed Control (%) - 20 DAA IPOHE | |
|---|---|---|---|
| gae/ha | gae/ha | Obs | Exp |
| 4.38 | 0 | 0 | — |
| 8.75 | 0 | 10 | — |
| 17.5 | 0 | 25 | — |
| 0 | 2.19 | 0 | — |
| 0 | 4.38 | 0 | — |
| 4.38 | 2.19 | 20 | 0 |
| 8.75 | 2.19 | 25 | 10 |
| 17.5 | 2.19 | 45 | 25 |
| 4.38 | 4.38 | NT | 0 |
| 8.75 | 4.38 | 30 | 10 |
| 17.5 | 4.38 | 35 | 25 |

TABLE 25

Synergistic Activity of Foliar-Applied Compound A Acid and Quinclorac Herbicidal Compositions on Weed Control in a Rice Cropping System.

| Compound A Acid | Quinclorac | Visual Weed Control (%) - 21 DAA CYPES | |
|---|---|---|---|
| gae/ha | gai/ha | Obs | Exp |
| 4.38 | 0 | 18 | — |
| 0 | 70 | 0 | — |
| 0 | 140 | 0 | — |
| 0 | 280 | 0 | — |
| 4.38 | 70 | 70 | 18 |
| 4.38 | 140 | 20 | 18 |
| 4.38 | 280 | 50 | 18 |

| Compound A Acid | Quinclorac | Visual Weed Control (%) - 21 DAA DIGSA | |
|---|---|---|---|
| gae/ha | gai/ha | Obs | Exp |
| 21.2 | 0 | 10 | — |
| 0 | 560 | 8 | — |
| 21.2 | 560 | 40 | 17 |

TABLE 26

Synergistic Activity of Foliar-Applied Compound A Benzyl Ester and Quinclorac Herbicidal Compositions on Weed Control in a Rice Cropping System.

| Compound A Benzyl Ester | Quinclorac | Visual Weed Control (%) - 21 DAA | | | |
|---|---|---|---|---|---|
| | | ECHCG | | CYPIR | |
| gae/ha | gai/ha | Obs | Exp | Obs | Exp |
| 4.38 | 0 | 48 | — | 75 | — |
| 8.75 | 0 | 55 | — | 85 | — |
| 0 | 70 | 15 | — | 0 | — |
| 0 | 140 | 30 | — | 0 | — |
| 0 | 280 | 30 | — | 0 | — |
| 4.38 | 70 | 50 | 55 | 95 | 75 |
| 8.75 | 70 | 80 | 62 | 100 | 85 |
| 4.38 | 140 | 70 | 63 | 30 | 75 |
| 8.75 | 140 | 80 | 69 | 100 | 85 |
| 4.38 | 280 | 99 | 63 | 95 | 75 |
| 8.75 | 280 | 70 | 69 | 100 | 85 |

| Compound A Benzyl Ester | Quinclorac | Visual Weed Control (%) - 20 DAA DIGSA | |
|---|---|---|---|
| gae/ha | gai/ha | Obs | Exp |
| 35 | 0 | 38 | — |
| 0 | 560 | 8 | — |
| 35 | 560 | 70 | 42 |

| Compound A Benzyl Ester | Quinclorac | Visual Weed Control (%) - 21 DAA ISCRU | |
|---|---|---|---|
| gae/ha | gai/ha | Obs | Exp |
| 8 | 0 | 20 | — |
| 16 | 0 | 0 | — |
| 0 | 140 | 0 | — |
| 0 | 280 | 0 | — |
| 0 | 560 | 0 | — |
| 8 | 140 | 50 | 20 |

TABLE 26-continued

Synergistic Activity of Foliar-Applied Compound A Benzyl Ester and Quinclorac Herbicidal Compositions on Weed Control in a Rice Cropping System.

| 16 | 140 | 100 | 0 |
| 8 | 280 | 100 | 20 |
| 16 | 280 | 50 | 0 |
| 8 | 560 | 20 | 20 |
| 16 | 560 | 70 | 0 |

| | | |
|---|---|---|
| BRAPP | *Brachiaria platyphylla* (Griseb.) Nash or *Urochloa platyphylla* (Nash) R. D. Webster | signalgrass, broadleaf |
| CYPDI | *Cyperus difformis* L. | sedge, smallflower umbrella |
| CYPES | *Cyperus esculentus* L. | nutsedge, yellow |
| CYPIR | *Cyperus iria* L. | flatsedge, rice |
| DIGSA | *Digitaria sanguinalis* (L.) Scop. | crabgrass, large |
| ECHCG | *Echinochloa crusgalli* (L.) Beauv. | barnyardgrass |
| ECHCO | *Echinochloa colona* (L.) Link | junglerice |
| IPOHE | *Ipomoea hederacea* Jacq. | morningglory, ivyleaf |
| ISCRU | *Ischaemum rugosum* Salisb. | saramollagrass |
| LEFCH | *Leptochloa chinensis* (L.) Nees | sprangletop, Chinese |
| SCPJU | *Schoenoplectus juncoides* (Roxb.) Palla | bulrush, Japanese | gae/ha = grams acid equivalent per hectare
gai/ha = grams active ingredient per hectare
Obs = observed value
Exp = expected value as calculated by Colby's equation
DAA = days after application
NT = not tested

Example II

Evaluation of In-Water Applied Herbicidal Mixtures for Weed Control in Transplanted Paddy Rice Weed seeds or nutlets of the desired test plant species were planted in puddled soil (mud) prepared by mixing a shredded, non-sterilized mineral soil (50.5 percent silt, 25.5 percent clay, and 24 percent sand, with a pH of about 7.6 and an organic matter content of about 2.9 percent) and water at a 1:1 volumetric ratio. The prepared mud was dispensed in 365 mL aliquots into 16-ounce (oz.) non-perforated plastic pots with a surface area of 86.59 square centimeters (cm²) leaving a headspace of 3 centimeters (cm) in each pot Mud was allowed to dry overnight prior to planting or transplanting. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 840 mL of mud contained in 32-oz. non-perforated plastic pots with a surface area of 86.59 cm² 4 days prior to herbicide application. The paddy was created by filling the headspace of the pots with 2.5 to 3 cm of water. When required to ensure good germination and healthy plants, a fungicide treatment and/or other chemical or physical treatment was applied. The plants were grown for 4-22 days in a greenhouse with an approximate 14 h photoperiod which was maintained at about 29° C. during the day and 26° C. during the night. Nutrients were added as Osmocote® (19:6:12, N:P:K⁺ minor nutrients) at 2 g per 16-oz. pot and 4 g per 32-oz. pot. Water was added on a regular basis to maintain the paddy flood, and supplemental lighting was provided with overhead metal halide 1000-Watt lamps as necessary. The plants were employed for testing when they reached the first through fourth true leaf stage.

Treatments consisted of the acid or esters of 4-amino-3-chloro-5-fluoro-6-(4-chloro-2-fluoro-3-methoxy-phenyl)pyridine-2-carboxylic acid (compound A) each formulated as an SC and various herbicidal components alone and in combination. Forms of compound A were applied on an acid equivalent basis.

Forms of Compound A (Compound of Formula I) Tested Include:

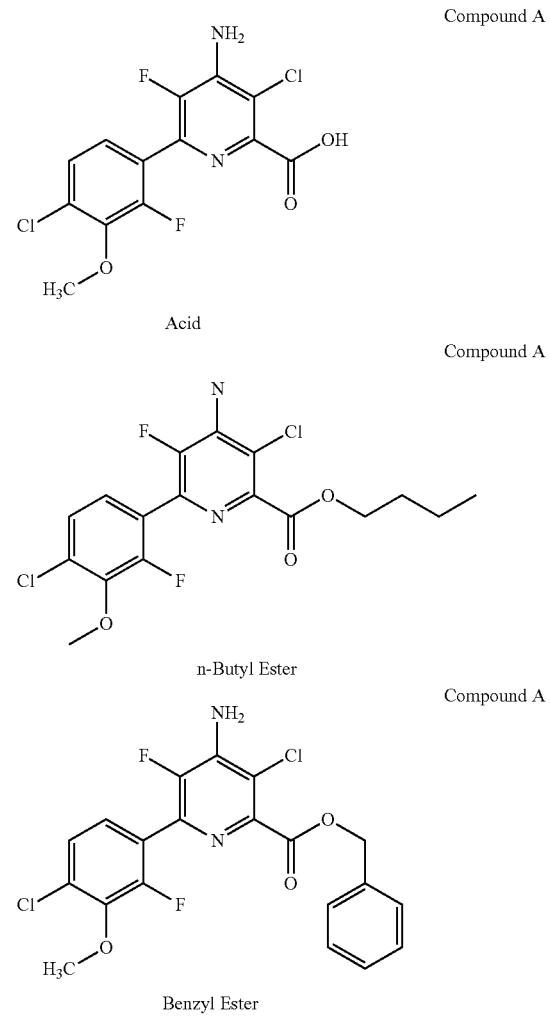

Other herbicidal components were applied on an acid equivalent basis or active ingredient basis and included 2,4-D dimethylammonium (DMA) salt formulated as Weedar® 64, 2,4-D choline salt formulated as a soluble liquid (SL), 2,4-D 2-ethylhexyl ester (EHE) formulated as an SL, MCPA K⁺/Na⁺/DMA salt formulated as Agritox 50, MCPA ethylhexyl ester formulated as MCPA2, fluoroxypyr methylheptyl ester (MHE) formulated as Starane® or Starane® Ultra, triclopyr choline salt formulated as an SL, triclopyr butotyl ester formulated as an EC, triclopyr triethylamine (TEA) salt formulated as Grandstand® R, dicamba dimethylammonium (DMA) salt formulated as Banvel® 4S, quinclorac formulated as Facet® 75DF, and halauxifen-methyl formulated as an SC.

Treatment requirements for each compound or herbicidal component were calculated based upon the rates being tested, the concentration of active ingredient or acid equivalent in the formulation, an application volume of 2 mL per component per pot, and an application area of 86.59 cm² per pot.

For formulated compounds, a measured amount was placed in an individual 100 or 200 mL glass vial and was dissolved in a volume of 1.25% (v/v) Agri-Dex® crop oil concentrate to obtain application solutions. If the test compound did not dissolve readily, the mixture was warmed and/or sonicated.

For technical grade compounds, a weighed amount can be placed in an individual 100 to 200 mL glass vial and dissolved in a volume of acetone to obtain concentrated stock solutions. If the test compound does not dissolve readily, the mixture can be warmed and/or sonicated. The concentrated stock solutions obtained can be diluted with an equivalent volume of an aqueous mixture containing 2.5% (v/v) crop oil concentrate so that the final application solutions contain 1.25% (v/v) crop oil concentrate.

Applications were made by injecting with a pipetter appropriate amounts of the application solutions, individually and sequentially, into the aqueous layer of the paddy. Control plants were treated in the same manner with the solvent blank. Applications were made so that all treated plant material received the same concentrations of acetone and crop oil concentrate.

The treated plants and control plants were placed in a greenhouse as described above and water was added as needed to maintain a paddy flood. After approximately 3 weeks the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.
B=observed efficacy of active ingredient B at the same concentration as used in the mixture.

Some of the compounds tested, application rates employed, plant species tested, and results are given in Tables 27-53.

TABLE 27

Synergistic Activity of In-Water Applications of Compound A Acid and 2,4-D Dimethylammonium (DMA) Salt Herbicidal Compositions on Weed Control in a Rice Cropping System.

| Compound A Acid | 2,4-D DMA Salt | Visual Weed Control (%) - 21 DAA | | | |
|---|---|---|---|---|---|
| | | ECHCG | | LEFCH | |
| gae/ha | gae/ha | Obs | Exp | Obs | Exp |
| 8.75 | 0 | 0 | — | 0 | — |
| 17.5 | 0 | 0 | — | 0 | — |
| 35 | 0 | 20 | — | 30 | — |
| 0 | 140 | 0 | — | 0 | — |
| 0 | 280 | 0 | — | 60 | — |
| 8.75 | 140 | 25 | 0 | 30 | 0 |
| 17.5 | 140 | 20 | 0 | 10 | 0 |
| 35 | 140 | 50 | 20 | 90 | 30 |
| 8.75 | 280 | 40 | 0 | 95 | 60 |
| 17.5 | 280 | 65 | 0 | 55 | 60 |
| 35 | 280 | 80 | 20 | 90 | 72 |

| Compound A Acid | 2,4-D DMA salt | Visual Weed Control (%) - 21 DAA | | | |
|---|---|---|---|---|---|
| | | ECHOR | | CYPRO | |
| gae/ha | gae/ha | Obs | Exp | Obs | Exp |
| 8.75 | 0 | 10 | — | 0 | — |
| 17.5 | 0 | 15 | — | 30 | — |
| 35 | 0 | 20 | — | 85 | — |
| 0 | 280 | 15 | — | 0 | — |
| 8.75 | 280 | 40 | 24 | 30 | 0 |
| 17.5 | 280 | 40 | 28 | 85 | 30 |
| 35 | 280 | 40 | 32 | 95 | 85 |

| Compound A Acid | 2,4-D DMA Salt | Visual Weed Control (%) - 21 DAA | |
|---|---|---|---|
| | | SCPJU | |
| gae/ha | gae/ha | Obs | Exp |
| 8.75 | 0 | 15 | — |
| 17.5 | 0 | 80 | — |
| 0 | 140 | 0 | — |
| 0 | 280 | 0 | — |
| 8.75 | 140 | 100 | 15 |
| 17.5 | 140 | 95 | 80 |
| 8.75 | 280 | 80 | 15 |
| 17.5 | 280 | 90 | 80 |

TABLE 28

Synergistic Activity of In-Water Applications of Compound A Benzyl Ester and 2,4-D Dimethylammonium (DMA) Salt Herbicidal Compositions on Weed Control in a Rice Cropping System.

| Compound A Benzyl Ester | 2,4-D DMA Salt | Visual Weed Control (%) - 21 DAA | | | |
|---|---|---|---|---|---|
| | | ECHCG | | LEFCH | |
| gae/ha | gae/ha | Obs | Exp | Obs | Exp |
| 4.38 | 0 | 0 | — | 0 | — |
| 8.75 | 0 | 0 | — | 0 | — |
| 17.5 | 0 | 25 | — | 0 | — |
| 0 | 140 | 0 | — | 0 | — |
| 0 | 280 | 0 | — | 60 | — |
| 4.38 | 140 | 40 | 0 | 30 | 0 |
| 8.75 | 140 | 35 | 0 | 30 | 0 |
| 17.5 | 140 | 75 | 25 | 55 | 0 |
| 4.38 | 280 | 20 | 0 | 80 | 60 |
| 8.75 | 280 | 20 | 0 | 65 | 60 |
| 17.5 | 280 | 70 | 25 | 85 | 60 |

| Compound A Benzyl Ester | 2,4-D DMA Salt | Visual Weed Control (%) - 21 DAA | |
|---|---|---|---|
| | | CYPRO | |
| gae/ha | gae/ha | Obs | Exp |
| 4.38 | 0 | 0 | — |
| 8.75 | 0 | 0 | — |
| 0 | 280 | 0 | — |
| 4.38 | 280 | 70 | 0 |
| 8.75 | 280 | 90 | 0 |

TABLE 29

Synergistic Activity of In-Water Applications of Compound A Acid and 2,4-D Choline Salt Herbicidal Compositions on Weed Control in a Rice Cropping System.

| Compound A Acid | 2,4-D Choline Salt | Visual Weed Control (%) - 20 DAA ECHOR | |
|---|---|---|---|
| gae/ha | gae/ha | Obs | Exp |
| 8.75 | 0 | 10 | — |
| 17.5 | 0 | 25 | — |
| 35 | 0 | 25 | — |
| 0 | 240 | 0 | — |
| 0 | 480 | 20 | — |
| 8.75 | 240 | 35 | 10 |
| 17.5 | 240 | 45 | 25 |
| 35 | 240 | 95 | 25 |
| 8.75 | 480 | 55 | 28 |
| 17.5 | 480 | 50 | 40 |
| 35 | 480 | 65 | 40 |

| Compound A Acid | 2,4-D Choline Salt | Visual Weed Control (%) - 20 DAA CYPRO | |
|---|---|---|---|
| gae/ha | gae/ha | Obs | Exp |
| 8.75 | 0 | 0 | — |
| 17.5 | 0 | 70 | — |
| 0 | 240 | 30 | — |
| 0 | 480 | 30 | — |
| 8.75 | 240 | 95 | 30 |
| 17.5 | 240 | 90 | 79 |
| 8.75 | 480 | 100 | 30 |
| 17.5 | 480 | 100 | 79 |

| Compound A Acid | 2,4-D Choline Salt | Visual Weed Control (%) - 20 DAA SCPMA | |
|---|---|---|---|
| gae/ha | gae/ha | Obs | Exp |
| 8.75 | 0 | 0 | — |
| 17.5 | 0 | 0 | — |
| 35 | 0 | 0 | — |
| 0 | 240 | 0 | — |
| 8.75 | 240 | 100 | 0 |
| 17.5 | 240 | 100 | 0 |
| 35 | 240 | 100 | 0 |

TABLE 30

Synergistic Activity of In-Water Applications of Compound A Benzyl Ester and 2,4-D Choline Salt Herbicidal Compositions on Weed Control in a Rice Cropping System.

| Compound A Benzyl Ester | 2,4-D Choline Salt | Visual Weed Control (%) - 20 DAA ECHOR | |
|---|---|---|---|
| gae/ha | gae/ha | Obs | Exp |
| 4.38 | 0 | 10 | — |
| 8.75 | 0 | 20 | — |
| 17.5 | 0 | 50 | — |
| 0 | 240 | 0 | — |
| 0 | 480 | 20 | — |
| 4.38 | 240 | 40 | 10 |
| 8.75 | 240 | 50 | 20 |
| 17.5 | 240 | 100 | 50 |
| 4.38 | 480 | 40 | 28 |
| 8.75 | 480 | 70 | 36 |
| 17.5 | 480 | 90 | 60 |

TABLE 31

Synergistic Activity of In-Water Applications of Compound A Acid and 2,4-D Ethylhexyl ester (EHE) Herbicidal Compositions on Weed Control in a Rice Cropping System.

| Compound A Acid | 2,4-D EHE | Visual Weed Control (%) - 22 DAA | | | | | |
|---|---|---|---|---|---|---|---|
| | | ECHCG | | ECHOR | | CYPRO | |
| gae/ha | gae/ha | Obs | Exp | Obs | Exp | Obs | Exp |
| 8.75 | 0 | 0 | — | 0 | — | 0 | — |
| 17.5 | 0 | 20 | — | 0 | — | 20 | — |
| 35 | 0 | 25 | — | 20 | — | 50 | — |
| 0 | 140 | 0 | — | 0 | — | 0 | — |
| 0 | 280 | 0 | — | 0 | — | 0 | — |
| 8.75 | 140 | 15 | 0 | 10 | 0 | 80 | 0 |
| 17.5 | 140 | 20 | 20 | 20 | 0 | 100 | 20 |
| 35 | 140 | 45 | 25 | 25 | 20 | 100 | 50 |
| 8.75 | 280 | 35 | 0 | 20 | 0 | 100 | 0 |
| 17.5 | 280 | 60 | 20 | 25 | 0 | 100 | 20 |
| 35 | 280 | 75 | 25 | 65 | 20 | 95 | 50 |

TABLE 32

Synergistic Activity of In-Water Applications of Compound A Benzyl Ester and 2,4-D Ethylhexyl ester (EHE) Herbicidal Compositions on Weed Control in a Rice Cropping System.

| Compound A Benzyl Ester | 2,4-D EHE | Visual Weed Control (%) - 22 DAA ECHOR | |
|---|---|---|---|
| gae/ha | gae/ha | Obs | Exp |
| 8.75 | 0 | 25 | — |
| 17.5 | 0 | 45 | — |
| 0 | 140 | 0 | — |
| 0 | 280 | 0 | — |
| 8.75 | 140 | 55 | 25 |
| 17.5 | 140 | 50 | 45 |
| 8.75 | 280 | 75 | 25 |
| 17.5 | 280 | 85 | 45 |

| Compound A Benzyl Ester | 2,4-D EHE | Visual Weed Control (%) - 22 DAA | | | |
|---|---|---|---|---|---|
| | | ECHCG | | CYPRO | |
| gae/ha | gae/ha | Obs | Exp | Obs | Exp |
| 4.38 | 0 | 30 | — | 90 | — |
| 8.75 | 0 | 45 | — | 70 | — |
| 0 | 140 | 0 | — | 0 | — |
| 0 | 280 | 0 | — | 0 | — |
| 4.38 | 140 | 15 | 30 | 100 | 90 |
| 8.75 | 140 | 60 | 45 | 100 | 70 |
| 4.38 | 280 | 45 | 30 | 100 | 90 |
| 8.75 | 280 | 45 | 45 | 100 | 70 |

TABLE 33

Synergistic Activity of In-Water Applications of Compound A Acid and MCPA (K+/Na+/DMA Salt) Herbicidal Compositions on Weed Control in a Rice Cropping System.

| Compound A Acid | MCPA Salt | Visual Weed Control (%) - 25 DAA ECHOR | |
|---|---|---|---|
| gae/ha | gai/ha | Obs | Exp |
| 8.75 | 0 | 0 | — |
| 17.5 | 0 | 0 | — |
| 35 | 0 | 40 | — |
| 0 | 140 | 0 | — |
| 8.75 | 140 | 10 | 0 |
| 17.5 | 140 | 20 | 0 |
| 35 | 140 | 60 | 40 |

| Compound A Acid | MCPA Salt | Visual Weed Control (%) - 25 DAA LEFCH | |
|---|---|---|---|
| gae/ha | gai/ha | Obs | Exp |
| 8.75 | 0 | 50 | — |
| 17.5 | 0 | 50 | — |
| 35 | 0 | 85 | — |
| 0 | 70 | 0 | — |
| 0 | 140 | 0 | — |
| 8.75 | 70 | 50 | 50 |
| 17.5 | 70 | 30 | 50 |
| 35 | 70 | 100 | 85 |
| 8.75 | 140 | 100 | 50 |
| 17.5 | 140 | 100 | 50 |
| 35 | 140 | 100 | 85 |

| Compound A Acid | MCPA Salt | Visual Weed Control (%) - 25 DAA SCPJU | |
|---|---|---|---|
| gae/ha | gai/ha | Obs | Exp |
| 8.75 | 0 | 65 | — |
| 17.5 | 0 | 80 | — |
| 35 | 0 | 95 | — |
| 0 | 70 | 0 | — |
| 8.75 | 70 | 85 | 65 |
| 17.5 | 70 | 90 | 80 |
| 35 | 70 | 100 | 95 |

TABLE 34

Synergistic Activity of In-Water Applications of Compound A Benzyl Ester and MCPA (K+/Na+/DMA Salt) Herbicidal Compositions on Weed Control in a Rice Cropping System.

| Compound A Benzyl Ester | MCPA Salt | Visual Weed Control (%) - 25 DAA LEFCH | |
|---|---|---|---|
| gae/ha | gai/ha | Obs | Exp |
| 8.75 | 0 | 50 | — |
| 17.5 | 0 | 90 | — |
| 0 | 70 | 0 | — |
| 0 | 140 | 0 | — |
| 8.75 | 70 | 100 | 50 |
| 17.5 | 70 | 100 | 90 |
| 8.75 | 140 | 100 | 50 |
| 17.5 | 140 | 100 | 90 |

TABLE 35

Synergistic Activity of In-Water Applications of Compound A Acid and MCPA Ethylhexyl Ester (EHE) Herbicidal Compositions on Weed Control in a Rice Cropping System.

| Compound A Acid | MCPA EHE | Visual Weed Control (%) - 19 DAA | | | |
|---|---|---|---|---|---|
| | | ECHOR | | LEFCH | |
| gae/ha | gai/ha | Obs | Exp | Obs | Exp |
| 42.4 | 0 | 15 | — | 10 | — |
| 0 | 280 | 30 | — | 0 | — |
| 42.4 | 280 | 97 | 40 | 70 | 10 |

TABLE 36

Synergistic Activity of In-Water Applications of Compound A Benzyl Ester and MCPA Ethylhexyl Ester (EHE) Herbicidal Compositions on Weed Control in a Rice Cropping System.

| Compound A Benzyl Ester | MCPA EHE | Visual Weed Control (%) - 19 DAA LEFCH | |
|---|---|---|---|
| gae/ha | gai/ha | Obs | Exp |
| 35 | 0 | 80 | — |
| 0 | 280 | 0 | — |
| 35 | 280 | 97 | 80 |

TABLE 37

Synergistic Activity of In-Water Applications of Compound A n-Butyl Ester and MCPA Ethylhexyl Ester (EHE) Herbicidal Compositions on Weed Control in a Rice Cropping System.

| Compound A n-Butyl Ester | MCPA EHE | Visual Weed Control (%) - 19 DAA LEFCH | |
|---|---|---|---|
| gae/ha | gai/ha | Obs | Exp |
| 35 | 0 | 43 | — |
| 0 | 280 | 0 | — |
| 35 | 280 | 85 | 43 |

TABLE 38

Synergistic Activity of In-Water Applications of Compound A Acid and Triclopyr Triethylamine (TEA) Salt Herbicidal Compositions on Weed Control in a Rice Cropping System.

| Compound A Acid | Triclopyr TEA Salt | Visual Weed Control (%) - 25 DAA | | | |
|---|---|---|---|---|---|
| gae/ha | gae/ha | Obs | Exp | Obs | Exp |
| | | ECHCG | | SCPJU | |
| 8.75 | 0 | 0 | — | 65 | — |
| 17.5 | 0 | 0 | — | 80 | — |
| 0 | 70 | 0 | — | 20 | — |
| 0 | 140 | 0 | — | 30 | — |
| 8.75 | 70 | 40 | 0 | 90 | 72 |
| 17.5 | 70 | 15 | 0 | 95 | 84 |
| 8.75 | 140 | 30 | 0 | 95 | 76 |
| 17.5 | 140 | 40 | 0 | 95 | 86 |
| | | ECHOR | | LEFCH | |
| 8.75 | 0 | 0 | — | 50 | — |
| 17.5 | 0 | 0 | — | 50 | — |

TABLE 38-continued

Synergistic Activity of In-Water Applications of Compound A Acid and Triclopyr Triethylamine (TEA) Salt Herbicidal Compositions on Weed Control in a Rice Cropping System.

| 35    | 0   | 40 | —  | 85  | —  |
|-------|-----|----|----|-----|----|
| 0     | 70  | 0  | —  | 0   | —  |
| 0     | 140 | 0  | —  | 0   | —  |
| 8.75  | 70  | 0  | 0  | 40  | 50 |
| 17.5  | 70  | 20 | 0  | 100 | 50 |
| 35    | 70  | 75 | 40 | 100 | 85 |
| 8.75  | 140 | 20 | 0  | 100 | 50 |
| 17.5  | 140 | 75 | 0  | 100 | 50 |
| 35    | 140 | 65 | 40 | 100 | 85 |

| Compound A Acid | Triclopyr TEA Salt | Visual Weed Control (%) - 19 DAA ECHOR | |
|---|---|---|---|
| gae/ha | gae/ha | Obs | Exp |
| 42.4 | 0   | 15 | —  |
| 0    | 280 | 35 | —  |
| 42.4 | 280 | 97 | 45 |

TABLE 39

Synergistic Activity of In-Water Applications of Compound A Benzyl Ester and Triclopyr Triethylamine (TEA) Salt Herbicidal Compositions on Weed Control in a Rice Cropping System.

| Compound A Benzyl Ester | Triclopyr TEA Salt | Visual Weed Control (%) - 25 DAA | | | |
|---|---|---|---|---|---|
| | | ECHOR | | LEFCH | |
| gae/ha | gae/ha | Obs | Exp | Obs | Exp |
| 8.75  | 0   | 85  | —  | 50  | —  |
| 17.5  | 0   | 90  | —  | 90  | —  |
| 0     | 70  | 0   | —  | 0   | —  |
| 0     | 140 | 0   | —  | 0   | —  |
| 8.75  | 70  | 99  | 85 | 100 | 50 |
| 17.5  | 70  | 100 | 90 | 100 | 90 |
| 8.75  | 140 | 99  | 85 | 100 | 50 |
| 17.5  | 140 | 100 | 90 | 100 | 90 |

TABLE 40

Synergistic Activity of In-Water Applications of Compound A Acid and Triclopyr Choline Salt Herbicidal Compositions on Weed Control in a Rice Cropping System.

| Compound A Acid | Triclopyr Choline Salt | Visual Weed Control (%) - 22 DAA | |
|---|---|---|---|
| gae/ha | gae/ha | Obs | Exp |
| | | ECHCG | |
| 21.2 | 0   | 25 | —  |
| 42.4 | 0   | 30 | —  |
| 0    | 140 | 20 | —  |
| 21.2 | 140 | 55 | 40 |
| 42.4 | 140 | 95 | 44 |
| | | LEFCH | |
| 10.6 | 0   | 20  | —  |
| 21.2 | 0   | 40  | —  |
| 42.4 | 0   | 60  | —  |
| 0    | 70  | 0   | —  |
| 0    | 140 | 0   | —  |
| 10.6 | 70  | 100 | 20 |
| 21.2 | 70  | 70  | 40 |

TABLE 40-continued

Synergistic Activity of In-Water Applications of Compound A Acid and Triclopyr Choline Salt Herbicidal Compositions on Weed Control in a Rice Cropping System.

| 42.4 | 70  | 100 | 60 |
| 10.6 | 140 | 100 | 20 |
| 21.2 | 140 | 100 | 40 |
| 42.4 | 140 | 100 | 60 |
| | | CYPRO | |
| 10.6 | 0   | 0   | —  |
| 21.2 | 0   | 40  | —  |
| 0    | 70  | 0   | —  |
| 0    | 140 | 0   | —  |
| 10.6 | 70  | 0   | 0  |
| 21.2 | 70  | 90  | 40 |
| 10.6 | 140 | 30  | 0  |
| 21.2 | 140 | 100 | 40 |

| Compound A Acid | Triclopyr Choline Salt | Visual Weed Control (%) - 22 DAA | | | |
|---|---|---|---|---|---|
| | | FIMMI | | SCPJU | |
| gae/ha | gae/ha | Obs | Exp | Obs | Exp |
| 10.6 | 0   | 40  | —  | 60 | —  |
| 0    | 70  | 15  | —  | 15 | —  |
| 0    | 140 | 80  | —  | 50 | —  |
| 10.6 | 70  | 100 | 49 | 90 | 66 |
| 10.6 | 140 | 100 | 88 | 99 | 80 |

TABLE 41

Synergistic Activity of In-Water Applications of Compound A Benzyl Ester and Triclopyr Choline Salt Herbicidal Compositions on Weed Control in a Rice Cropping System.

| Compound A Benzyl Ester | Triclopyr Choline Salt | Visual Weed Control (%) - 22 DAA | |
|---|---|---|---|
| gae/ha | gae/ha | Obs | Exp |
| | | ECHCG | |
| 4.38 | 0   | 30 | —  |
| 8.75 | 0   | 45 | —  |
| 17.5 | 0   | 90 | —  |
| 0    | 70  | 15 | —  |
| 0    | 140 | 20 | —  |
| 4.38 | 70  | 70 | 41 |
| 8.75 | 70  | 80 | 53 |
| 17.5 | 70  | 99 | 92 |
| 4.38 | 140 | 80 | 44 |
| 8.75 | 140 | 30 | 56 |
| 17.5 | 140 | 95 | 92 |
| | | ECHOR | |
| 8.75 | 0   | 35 | —  |
| 17.5 | 0   | 30 | —  |
| 0    | 70  | 10 | —  |
| 0    | 140 | 15 | —  |
| 8.75 | 70  | 90 | 42 |
| 17.5 | 70  | 95 | 37 |
| 8.75 | 140 | 85 | 45 |
| 17.5 | 140 | 85 | 41 |

TABLE 42

Synergistic Activity of In-Water Applications of Compound A Acid and Triclopyr Butotyl Ester Herbicidal Compositions on Weed Control in a Rice Cropping System.

| Compound A Acid gae/ha | Triclopyr Butotyl Ester gae/ha | Visual Weed Control (%) - 22 DAA | | | |
|---|---|---|---|---|---|
| | | Obs | Exp | Obs | Exp |
| | | ECHCG | | ECHOR | |
| 8.75 | 0 | 0 | — | 0 | — |
| 17.5 | 0 | 20 | — | 0 | — |
| 35 | 0 | 25 | — | 20 | — |
| 0 | 70 | 0 | — | 0 | — |
| 0 | 140 | 0 | — | 0 | — |
| 8.75 | 70 | 20 | 0 | 20 | 0 |
| 17.5 | 70 | 30 | 20 | 40 | 0 |
| 35 | 70 | 50 | 25 | 20 | 20 |
| 8.75 | 140 | 30 | 0 | 20 | 0 |
| 17.5 | 140 | 25 | 20 | 40 | 0 |
| 35 | 140 | 40 | 25 | 40 | 20 |
| | | CYPRO | | SCPMA | |
| 8.75 | 0 | 0 | — | 0 | — |
| 17.5 | 0 | 20 | — | 0 | — |
| 35 | 0 | 50 | — | 0 | — |
| 0 | 70 | 0 | — | 50 | — |
| 0 | 140 | 40 | — | 60 | — |
| 8.75 | 70 | 30 | 0 | 20 | 50 |
| 17.5 | 70 | 100 | 20 | 60 | 50 |
| 35 | 70 | 100 | 50 | 100 | 50 |
| 8.75 | 140 | 50 | 40 | 100 | 60 |
| 17.5 | 140 | 100 | 52 | 100 | 60 |
| 35 | 140 | 95 | 70 | 100 | 60 |

TABLE 43

Synergistic Activity of In-Water Applications of Compound A Benzyl Ester and Triclopyr Butotyl Ester Herbicidal Compositions on Weed Control in a Rice Cropping System.

| Compound A Benzyl Ester gae/ha | Triclopyr Butotyl Ester gae/ha | Visual Weed Control (%) - 22 DAA SCPMA | |
|---|---|---|---|
| | | Obs | Exp |
| 4.38 | 0 | 0 | — |
| 8.75 | 0 | 0 | — |
| 17.5 | 0 | 0 | — |
| 0 | 70 | 50 | — |
| 0 | 140 | 60 | — |
| 4.38 | 70 | 100 | 50 |
| 8.75 | 70 | 100 | 50 |
| 17.5 | 70 | 90 | 50 |
| 4.38 | 140 | 100 | 60 |
| 8.75 | 140 | 100 | 60 |
| 17.5 | 140 | 100 | 60 |

TABLE 44

Synergistic Activity of In-Water Applications of Compound A Acid and Fluroxypyr Methylheptyl Ester (MHE) Herbicidal Compositions on Weed Control in a Rice Cropping System.

| Compound A Acid gae/ha | Fluroxypyr MHE gae/ha | Visual Weed Control (%) - 25 DAA | |
|---|---|---|---|
| | | Obs | Exp |
| | | ECHCG | |
| 8.75 | 0 | 0 | — |
| 17.5 | 0 | 0 | — |
| 35 | 0 | 70 | — |
| 0 | 140 | 0 | — |
| 8.75 | 140 | 40 | 0 |
| 17.5 | 140 | 50 | 0 |
| 35 | 140 | 90 | 70 |
| | | LEFCH | |
| 8.75 | 0 | 50 | — |
| 17.5 | 0 | 50 | — |
| 35 | 0 | 85 | — |
| 0 | 70 | 20 | — |
| 8.75 | 70 | 100 | 60 |
| 17.5 | 70 | 100 | 60 |
| 35 | 70 | 100 | 88 |

| Compound A Acid gae/ha | Fluroxypyr MHE gae/ha | Visual Weed Control (%) - 25 DAA | | | |
|---|---|---|---|---|---|
| | | ECHOR | | SCPJU | |
| | | Obs | Exp | Obs | Exp |
| 8.75 | 0 | 0 | — | 65 | — |
| 17.5 | 0 | 0 | — | 80 | — |
| 35 | 0 | 40 | — | 95 | — |
| 0 | 70 | 0 | — | 20 | — |
| 0 | 140 | 0 | — | 30 | — |
| 8.75 | 70 | 50 | 0 | 90 | 65 |
| 17.5 | 70 | 50 | 0 | 90 | 80 |
| 35 | 70 | 100 | 40 | 99 | 95 |
| 8.75 | 140 | 15 | 0 | 95 | 76 |
| 17.5 | 140 | 70 | 0 | 95 | 86 |
| 35 | 140 | 95 | 40 | 100 | 97 |

| Compound A Acid gae/ha | Fluroxypyr MHE gae/ha | Obs | Exp |
|---|---|---|---|
| | | Visual Weed Control (%) - 22 DAA SCPMA | |
| 16 | 0 | 0 | — |
| 32 | 0 | 0 | — |
| 64 | 0 | 30 | — |
| 0 | 149 | 30 | — |
| 16 | 149 | 100 | 30 |
| 32 | 149 | 100 | 30 |
| 64 | 149 | 100 | 51 |
| | | Visual Weed Control (%) - 19 DAA ECHOR | |
| 42.4 | 0 | 15 | — |
| 0 | 280 | 15 | — |
| 42.4 | 280 | 98 | 28 |

TABLE 45

Synergistic Activity of In-Water Applications of Compound A Benzyl Ester and Fluroxypyr Methylheptyl Ester (MHE) Herbicidal Compositions on Weed Control in a Rice Cropping System.

| Compound A Benzyl Ester gae/ha | Fluroxypyr MHE gae/ha | Obs | Exp |
|---|---|---|---|
| | | Visual Weed Control (%) - 25 DAA ECHOR | |
| 8.75 | 0 | 85 | — |
| 0 | 70 | 0 | — |
| 0 | 140 | 0 | — |
| 8.75 | 70 | 99 | 85 |
| 8.75 | 140 | 99 | 85 |
| | | Visual Injury (%) - 25 DAA LEFCH | |
| 8.75 | 0 | 50 | — |
| 17.5 | 0 | 90 | — |
| 0 | 70 | 20 | — |
| 8.75 | 70 | 100 | 60 |
| 17.5 | 70 | 100 | 92 |
| | | Visual Weed Control (%) - 19 DAA ECHCG | |
| 8 | 0 | 35 | — |
| 16 | 0 | 85 | — |
| 0 | 70 | 0 | — |
| 0 | 140 | 0 | — |
| 0 | 280 | 0 | — |
| 8 | 70 | 60 | 35 |
| 16 | 70 | 90 | 85 |
| 8 | 140 | 65 | 35 |
| 16 | 140 | 95 | 85 |
| 8 | 280 | 80 | 35 |
| 16 | 280 | 100 | 85 |
| | | Visual Weed Control (%) - 19 DAA ECHOR | |
| 8 | 0 | 10 | — |
| 16 | 0 | 25 | — |
| 32 | 0 | 35 | — |
| 0 | 70 | 0 | — |
| 0 | 140 | 0 | — |
| 0 | 280 | 0 | — |
| 8 | 70 | 20 | 10 |
| 16 | 70 | 40 | 25 |
| 32 | 70 | 75 | 35 |
| 8 | 140 | 25 | 10 |
| 16 | 140 | 75 | 25 |
| 32 | 140 | 70 | 35 |
| 8 | 280 | 50 | 10 |
| 16 | 280 | 70 | 25 |
| 32 | 280 | 60 | 35 |

TABLE 46

Synergistic Activity of In-Water Applications of Compound A n-Butyl Ester and Fluroxypyr Methylheptyl Ester (MHE) Herbicidal Compositions on Weed Control in a Rice Cropping System.

| Compound A n-Butyl Ester gae/ha | Fluroxypyr MHE gae/ha | Visual Weed Control (%) - 19 DAA ECHOR | |
|---|---|---|---|
| | | Obs | Exp |
| 35 | 0 | 80 | — |
| 0 | 280 | 15 | — |
| 35 | 280 | 100 | 83 |

TABLE 47

Synergistic Activity of In-Water Applications of Compound A Acid and Dicamba Dimethylammonium (DMA) Salt Herbicidal Compositions on Control of Weeds Common to Rice Cropping Systems.

| Compound A Acid gae/ha | Dicamba DMA Salt gae/ha | Visual Weed Control (%) - 21 DAA ECHCG | |
|---|---|---|---|
| | | Obs | Exp |
| 10.6 | 0 | 0 | — |
| 0 | 140 | 0 | — |
| 0 | 280 | 10 | — |
| 10.6 | 140 | 25 | 0 |
| 10.6 | 280 | 30 | 10 |

| Compound A Acid | Dicamba DMA Salt | Visual Weed Control (%) - 21 DAA | | | |
|---|---|---|---|---|---|
| | | ECHOR | | SCPMA | |
| gae/ha | gae/ha | Obs | Exp | Obs | Exp |
| 42.4 | 0 | 15 | — | 0 | — |
| 0 | 140 | 10 | — | 0 | — |
| 0 | 280 | 15 | — | 0 | — |
| 42.4 | 140 | 35 | 24 | 60 | 0 |
| 42.4 | 280 | 50 | 28 | 100 | 0 |

TABLE 48

Synergistic Activity of In-Water Applications of Compound A Benzyl Ester and Dicamba Dimethylammonium (DMA) Salt Herbicidal Compositions on Control of Weeds Common to Rice Cropping Systems

| Compound A Benzyl Ester gae/ha | Dicamba DMA Salt gai/ha | Visual Weed Control (%) - 21 DAA | |
|---|---|---|---|
| | | Obs | Exp |
| | | ECHOR | |
| 4.38 | 0 | 15 | — |
| 8.75 | 0 | 15 | — |
| 17.5 | 0 | 20 | — |
| 0 | 140 | 10 | — |
| 0 | 280 | 15 | — |
| 4.38 | 140 | 30 | 24 |
| 8.75 | 140 | 30 | 24 |
| 17.5 | 140 | 40 | 28 |
| 4.38 | 280 | 40 | 28 |
| 8.75 | 280 | 45 | 28 |
| 17.5 | 280 | 50 | 32 |

TABLE 48-continued

Synergistic Activity of In-Water Applications of Compound A Benzyl Ester and Dicamba Dimethylammonium (DMA) Salt Herbicidal Compositions on Control of Weeds Common to Rice Cropping Systems

| Compound A Benzyl Ester | Dicamba DMA Salt | Visual Weed Control (%) - 21 DAA | |
|---|---|---|---|
| gae/ha | gai/ha | Obs | Exp |
| | | SCPMA | |
| 4.38 | 0 | 0 | — |
| 8.75 | 0 | 0 | — |
| 17.5 | 0 | 0 | — |
| 0 | 140 | 0 | — |
| 4.38 | 140 | 95 | 0 |
| 8.75 | 140 | 70 | 0 |
| 17.5 | 140 | 100 | 0 |

TABLE 49

Synergistic Activity of In-Water Applications of Compound A Acid and Halauxifen-Methyl Ester Herbicidal Compositions on Weed Control in a Rice Cropping System.

| Compound A Acid | Halauxifen-Methyl Ester | Visual Weed Control (%) - 20 DAA | |
|---|---|---|---|
| gae/ha | gae/ha | Obs | Exp |
| | | ECHCG | |
| 10.6 | 0 | 20 | — |
| 21.2 | 0 | 20 | — |
| 42.4 | 0 | 50 | — |
| 0 | 4.38 | 50 | — |
| 0 | 8.75 | 60 | — |
| 10.6 | 4.38 | 80 | 60 |
| 21.2 | 4.38 | 90 | 60 |
| 42.4 | 4.38 | 100 | 75 |
| 10.6 | 8.75 | 100 | 68 |
| 21.2 | 8.75 | 95 | 68 |
| 42.4 | 8.75 | 99 | 80 |
| | | ECHOR | |
| 21.2 | 0 | 30 | — |
| 42.4 | 0 | 45 | — |
| 0 | 4.38 | 25 | — |
| 0 | 8.75 | 35 | — |
| 21.2 | 4.38 | 95 | 48 |
| 42.4 | 4.38 | 40 | 59 |
| 21.2 | 8.75 | 95 | 55 |
| 42.4 | 8.75 | 95 | 64 |
| | | CYPRO | |
| 10.6 | 0 | 10 | — |
| 21.2 | 0 | 20 | — |
| 0 | 4.38 | 70 | — |
| 0 | 8.75 | 50 | — |
| 10.6 | 4.38 | 20 | 73 |
| 21.2 | 4.38 | 100 | 76 |
| 10.6 | 8.75 | 100 | 55 |
| 21.2 | 8.75 | 100 | 60 |

TABLE 50

Synergistic Activity of In-Water Applications of Compound A Benzyl Ester and Halauxifen-Methyl Ester Herbicidal Compositions on Weed Control in a Rice Cropping System.

| Compound A Benzyl Ester | Halauxifen-Methyl Ester | Visual Weed Control (%) - 20 DAA | | | |
|---|---|---|---|---|---|
| | | ECHCG | | ECHOR | |
| gae/ha | gae/ha | Obs | Exp | Obs | Exp |
| 4.38 | 0 | 15 | — | 25 | — |
| 8.75 | 0 | 20 | — | 20 | — |
| 17.5 | 0 | 40 | — | 30 | — |
| 0 | 4.38 | 50 | — | 25 | — |
| 0 | 8.75 | 60 | — | 35 | — |
| 4.38 | 4.38 | 99 | 58 | 85 | 44 |
| 8.75 | 4.38 | 95 | 60 | 85 | 40 |
| 17.5 | 4.38 | 80 | 70 | 99 | 48 |
| 4.38 | 8.75 | 95 | 66 | 50 | 51 |
| 8.75 | 8.75 | 90 | 68 | 90 | 48 |
| 17.5 | 8.75 | 99 | 76 | 100 | 55 |

| Compound A Benzyl Ester | Halauxifen-Methyl Ester | Visual Weed Control (%) - 20 DAA CYPRO | |
|---|---|---|---|
| gae/ha | gae/ha | Obs | Exp |
| 4.38 | 0 | 0 | — |
| 8.75 | 0 | 0 | — |
| 0 | 4.38 | 70 | — |
| 0 | 8.75 | 50 | — |
| 4.38 | 4.38 | 70 | 85 |
| 8.75 | 4.38 | 100 | 70 |
| 4.38 | 8.75 | 95 | 75 |
| 8.75 | 8.75 | 90 | 50 |

TABLE 51

Synergistic Activity of In-Water Applications of Compound A Acid and Quinclorac Herbicidal Compositions on Weed Control in a Rice Cropping System.

| Compound A Acid | Quinclorac | Visual Weed Control (%) - 21 DAA | | | |
|---|---|---|---|---|---|
| | | ECHOR | | CYPIR | |
| gae/ha | gai/ha | Obs | Exp | Obs | Exp |
| 8.75 | 0 | 0 | — | 0 | — |
| 17.5 | 0 | 0 | — | 0 | — |
| 35 | 0 | 20 | — | 95 | — |
| 0 | 560 | 0 | — | 0 | — |
| 8.75 | 560 | 20 | 0 | 50 | 0 |
| 17.5 | 560 | 30 | 0 | 85 | 0 |
| 35 | 560 | 30 | 20 | 95 | 95 |

| Compound A Acid | Quinclorac | Visual Weed Control (%) - 20 DAA | | | |
|---|---|---|---|---|---|
| | | ECHOR | | SCPMA | |
| gae/ha | gai/ha | Obs | Exp | Obs | Exp |
| 42.4 | 0 | 18 | — | 0 | — |
| 84.8 | 0 | 33 | — | 0 | — |
| 0 | 560 | 20 | — | 0 | — |
| 42.4 | 560 | 50 | 34 | 0 | 0 |
| 84.8 | 560 | 68 | 46 | 100 | 0 |

TABLE 52

Synergistic Activity of In-Water Applications of Compound A n-Butyl Ester and Quinclorac Herbicidal Compositions on Weed Control in a Rice Cropping System.

| Compound A n-Butyl Ester | Quinclorac | Visual Weed Control (%) - 20 DAA SCPMA | |
|---|---|---|---|
| gae/ha | gai/ha | Obs | Exp |
| 35 | 0 | 0 | — |
| 70 | 0 | 0 | — |
| 0 | 560 | 0 | — |
| 35 | 560 | 65 | 0 |
| 70 | 560 | 100 | 0 |

TABLE 53

Synergistic Activity of In-Water Applications of Compound A Benzyl Ester and Quinclorac Herbicidal Compositions on Weed Control in a Rice Cropping System.

| Compound A Benzyl Ester | Quinclorac | Visual Weed Control (%) - 20 DAA | |
|---|---|---|---|
| gae/ha | gai/ha | Obs | Exp |
| | | ECHOR | |
| 35 | 0 | 73 | — |
| 0 | 560 | 20 | — |
| 35 | 560 | 97 | 78 |
| | | SCPMA | |
| 35 | 0 | 0 | — |
| 70 | 0 | 0 | — |
| 0 | 560 | 0 | — |
| 35 | 560 | 100 | 0 |
| 70 | 560 | 100 | 0 |

CYPIR — *Cyperus iria* L. — flatsedge, rice
CYPRO — *Cyperus rotundus* L. — nutsedge, purple
ECHCG — *Echinochloa crusgalli* (L.) Beauv. — barnyardgrass
ECHOR — *Echinochloa oryzoides* (Ard.) Fritsch — watergrass, early
FIMMI — *Fimbristylis miliacea* (L.) Vahl — fringerush, globe
LEFCH — *Leptochloa chinensis* (L.) Nees — sprangletop, Chinese
SCPJU — *Schoenoplectus juncoides* (Roxb.) Palla — bulrush, Japanese
SCPMA — *Schoenoplectus maritimus* (L.) Lye — clubrush, sea
gae/ha = grams acid equivalent per hectare
gai/ha = grams active ingredient per hectare
Obs = observed value
Exp = expected value as calculated by Colby's equation
DAA = days after application
NT = not tested

Example III

Evaluation of Postemergence Foliar-Applied Herbicidal Mixtures for Control of Weeds Common to Row Crops such as Corn and Soybeans Seeds or nutlets of the desired test plant species were planted in a soil matrix prepared by mixing a loam or sandy loam soil (e.g., 28.6 percent silt, 18.8 percent clay, and 52.6 percent sand, with a pH of about 5.8 and an organic matter content of about 1.8 percent) and calcareous grit in an 80 to 20 ratio. The soil matrix was contained in plastic pots with a surface area of 84.6 square centimeters ($cm^2$) and a volume of 560 cubic centimeters ($cm^3$). When required to ensure good germination and healthy plants, a fungicide treatment and/or other chemical or physical treatment was applied. The plants were grown for 7-31 days (d) in a greenhouse with an approximate 15 hour (h) photoperiod which was maintained at about 23-29° C. during the day and 22-28° C. during the night. Nutrients (Peters Excel® 15-5-15 5-Ca 2-Mg) and water were added on a regular basis and supplemental lighting was provided with overhead metal halide 1000-Watt lamps as necessary. The plants were employed for testing when they reached the first, second, or third true leaf stage.

Treatment requirements were calculated based upon the rates being tested, the concentration of active ingredient or acid equivalent in the formulation, and a 12 mL application volume at a rate of 187 L/ha.

Treatments consisted of the acid or esters of 4-amino-3-chloro-5-fluoro-6-(4-chloro-2-fluoro-3-methoxy-phenyl)pyridine-2-carboxylic acid (Compound A), each formulated as an SC, and various herbicidal components alone and in combination. Forms of compound A were applied on an acid equivalent basis.

Forms of Compound A (Compound of Formula I) Tested Include:

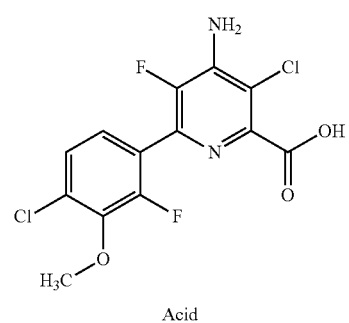

Compound A Acid

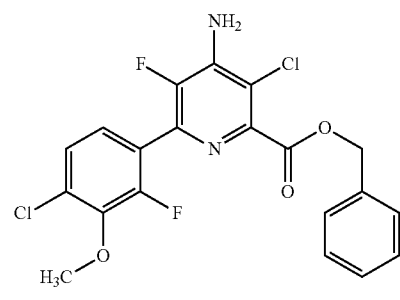

Compound A Benzyl Ester

Other herbicidal components were applied on an acid equivalent basis and included the synthetic auxin herbicides 2,4-D dimethylamine salt formulated as Weedar® 64 and Halauxifen K+ salt formulated as a soluble liquid (SL). For treatments comprised of formulated compounds, measured amounts of compounds were placed individually in 25 mL glass vials and diluted in a volume of 1.5% (v/v) Agri-Dex® crop oil concentrated to obtain 6× stock solutions. If a test compound did not dissolve readily, the mixture was warmed and/or sonicated. Application solutions were prepared by adding an appropriate amount of each stock solution (typically 2 mL) and diluted to the appropriate final concentrations with the addition of an appropriate amount of an aqueous mixture of 1.5% (v/v) crop oil concentrate and water so that the final spray solutions contained 1.25+/−0.05% (v/v) crop oil concentrate.

For treatments comprised of technical compounds, weighed amounts can be placed individually in 25 mL glass vials and dissolved in a volume of 97:3 v/v acetone/DMSO to obtain 6× stock solutions. If a test compound does not dissolve readily, the mixture can be warmed and/or sonicated. Application solutions can be prepared by adding an appropriate amount of each stock solution (e.g., 2 mL) and diluted to the appropriate final concentrations with the addition of an appropriate amount of an aqueous mixture of 1.5% (v/v) crop oil concentrate and water so that the final spray solutions contain 1.25% (v/v) crop oil concentrate. When technical materials are used, the concentrated stock solutions can be added to the spray solutions so that the final acetone and DMSO concentrations of the application solutions are 16.2% and 0.5%, respectively.

For treatments comprised of formulated and technical compounds, weighed amounts of the technical materials can be placed individually in 25 mL glass vials and dissolved in a volume of 97:3 v/v acetone/DMSO to obtain 6× stock solutions, and measured amounts of the formulated compounds can be placed individually in 25 mL glass vials and diluted in a volume of 1.5% (v/v) crop oil concentrate or water to obtain 6× stock solutions. If a test compound does not dissolve readily, the mixture was warmed and/or sonicated. Application solutions can be prepared by adding an appropriate amount of each stock solution (e.g., 2 mL) and diluted to the appropriate final concentrations with the addition of an appropriate amount of an aqueous mixture of 1.5% (v/v) crop oil concentrate and water so that the final spray solutions contained 1.25% (v/v) crop oil concentrate. When required, additional water and/or 97:3 v/v acetone/DMSO can be added to individual application solutions so that the final acetone and DMSO concentrations of the application solutions being compared are 16.2% and 0.5%, respectively.

All stock solutions and applications solutions were visually inspected for compound compatibility prior to application. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters ($m^2$) at a spray height of 18 to 20 inches (46 to 50 cm) above the average plant canopy height. Control plants were sprayed in the same manner with the solvent blank.

The treated plants and control plants were placed in a greenhouse as described above and watered by sub-irrigation to prevent wash-off of the test compounds. After approximately 2 weeks, the condition of the test plants as compared with that of the untreated plants was determined visually and scored on a scale of 0 to 100 percent where 0 corresponds to no injury or growth inhibition and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 54-56.

TABLE 54

Synergistic Activity of Foliar-Applied Compound A Acid and 2,4-D DMA Salt Herbicidal Compositions on Control of Weeds Common to Row Crops, Corn and Soybeans.

| Compound A Acid | 2,4-D DMA Salt | Visual Weed Control (%) - 16 DAA PANDI | |
|---|---|---|---|
| gae/ha | gae/ha | Obs | Exp |
| 3.75 | 0 | 60 | — |
| 0 | 105 | 0 | — |
| 0 | 210 | 0 | — |
| 3.75 | 105 | 75 | 60 |
| 3.75 | 210 | 80 | 60 |

TABLE 55

Synergistic Activity of Foliar-Applied Compound A Benzyl Ester and 2,4-D DMA Salt Herbicidal Compositions on Control of Weeds Common to Corn and Soybeans.

| Compound A Benzyl Ester | 2,4-D DMA Salt | Visual Weed Control (%) - 14 DAA ELEIN | |
|---|---|---|---|
| gae/ha | gae/ha | Obs | Exp |
| 3.75 | 0 | 0 | — |
| 0 | 52.5 | 0 | — |
| 0 | 105 | 0 | — |
| 3.75 | 52.5 | 15 | 0 |
| 3.75 | 105 | 15 | 0 |

| Compound A Benzyl Ester | 2,4-D DMA Salt | Visual Weed Control (%) - 16 DAA PANMI | |
|---|---|---|---|
| gae/ha | gae/ha | Obs | Exp |
| 3.75 | 0 | 15 | — |
| 7.5 | 0 | 50 | — |
| 15 | 0 | 75 | — |
| 0 | 52.5 | 0 | — |
| 0 | 105 | 10 | — |
| 3.75 | 52.5 | 50 | 15 |
| 7.5 | 52.5 | 45 | 50 |
| 15 | 52.5 | 90 | 75 |
| 3.75 | 105 | 60 | 24 |
| 7.5 | 105 | 75 | 55 |
| 15 | 105 | 75 | 78 |

TABLE 56

Synergistic Activity of Foliar-Applied Compound A Benzyl Ester and Halauxifen $K^+$ Salt Herbicidal Compositions on Control of Weeds Common to Corn and Soybeans.

| Compound A Benzyl Ester | Halauxifen $K^+$ Salt | Visual Weed Control (%) - 17 DAA ELEIN | |
|---|---|---|---|
| gae/ha | gae/ha | Obs | Exp |
| 7.5 | 0 | 20 | — |
| 0 | 3.75 | 30 | — |

TABLE 56-continued

Synergistic Activity of Foliar-Applied Compound A Benzyl Ester and Halauxifen K+ Salt Herbicidal Compositions on Control of Weeds Common to Corn and Soybeans.

| 0 | 7.5 | 40 | — |
| 0 | 15 | 50 | — |
| 7.5 | 3.75 | 45 | 44 |
| 7.5 | 7.5 | 60 | 52 |
| 7.5 | 15 | 75 | 60 |

| Compound A Benzyl Ester | Halauxifen K+ Salt | Visual Weed Control (%) - 13 DAA SORHA | |
|---|---|---|---|
| gae/ha | gae/ha | Obs | Exp |
| 3.75 | 0 | 0 | — |
| 7.5 | 0 | 0 | — |
| 15 | 0 | 10 | — |
| 0 | 7.5 | 0 | — |
| 3.75 | 7.5 | 20 | 0 |
| 7.5 | 7.5 | 15 | 0 |
| 15 | 7.5 | 10 | 10 |

| | | |
|---|---|---|
| ELEIN | *Eleusine indica* (L.) Gaertn. | goosegrass |
| PANDI | *Panicum dichotomiflorum* Michx. | panicum, fall |
| PANMI | *Panicum miliaceum* L. | millet, wild-proso |
| SORHA | *Sorghum halepense* (L.) Pers. | johnsongrass | gae/ha = grams acid equivalent per hectare
gai/ha = grams active ingredient per hectare
Obs = observed value
Exp = expected value as calculated by Colby's equation
DAA = days after application

Example IV

Evaluation of Postemergence Foliar-Applied Herbicidal Mixtures for Weed Control in Cereal Crops in the Greenhouse Seeds of the desired test plant species were planted in Sun Gro MetroMix 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as an SC, and a second cereal herbicide alone and in combination. Forms of Compound A (Compound of Formula I) Tested Include:

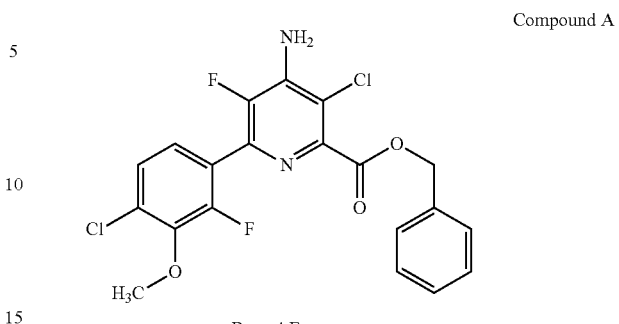

Benzyl Ester

Measured aliquots of benzyl ester of 4-amino-3-chloro-5-fluoro-6-(4-chloro-2-fluoro-3-methoxy-phenyl)pyridine-2-carboxylic acid (Compound A) were placed in 25 milliliter (mL) glass vials and diluted in a volume of 1.25% (v/v) Agri-Dex® crop oil concentrated to obtain stock solutions. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

$$Expected = A + B - (A \times B/100)$$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 57-66.

TABLE 57

Synergistic Activity of Foliar-Applied Compound A Benzyl Ester and 2,4-DB Herbicidal Compositions on Weed Control in a Cereal Cropping System.

| Application Rate (gai/ha) | | POLCO | |
|---|---|---|---|
| Compound A Benzyl Ester | 2,4-DB | Ob | Ex |
| 8.75 | 0 | 50 | — |
| 0 | 150 | 17 | — |
| 8.75 | 150 | 67 | 58 |

TABLE 58

Synergistic Activity of Foliar-Applied Compound A Benzyl Ester and Dichlorprop-P Herbicidal Compositions on Weed Control in a Cereal Cropping System.

| Application Rate (gai/ha) | | VIOTR | | BRSNN | |
|---|---|---|---|---|---|
| Compound A Benzyl Ester | Dichlorprop-P | Ob | Ex | Ob | Ex |
| 8.75 | 0 | 30 | — | 23 | — |
| 0 | 140 | 27 | — | 57 | — |
| 8.75 | 140 | 57 | 49 | 77 | 67 |

TABLE 59

Synergistic Activity of Foliar-Applied Compound A Benzyl Ester and MCPA Herbicidal Compositions on Weed Control in a Cereal Cropping System.

| Application Rate (gai/ha) | | VIOTR | | POLCO | | BRSNN | |
|---|---|---|---|---|---|---|---|
| Compound A Benzyl Ester | MCPA | Ob | Ex | Ob | Ex | Ob | Ex |
| 8.75 | 0 | 30 | — | 50 | — | 23 | — |
| 0 | 140 | 40 | — | 0 | — | 70 | — |
| 8.75 | 140 | 78 | 58 | 62 | 50 | 87 | 77 |

TABLE 60

Synergistic Activity of Foliar-Applied Compound A Benzyl Ester and Mecoprop Herbicidal Compositions on Weed Control in a Cereal Cropping System.

| Application Rate (gai/ha) | | BRSNN | |
|---|---|---|---|
| Compound A Benzyl Ester | Mecoprop-P | Ob | Ex |
| 8.75 | 0 | 23 | — |
| 0 | 200 | 70 | — |
| 8.75 | 200 | 83 | 77 |

TABLE 61

Synergistic Activity of Foliar-Applied Compound A Benzyl Ester and Dicamba Herbicidal Compositions on Weed Control in a Cereal Cropping System.

| Application Rate (gai/ha) | | AMARE | | POLCO | | BRSNN | |
|---|---|---|---|---|---|---|---|
| Compound A Benzyl Ester | Dicamba | Ob | Ex | Ob | Ex | Ob | Ex |
| 8.75 | 0 | 60 | — | 50 | — | 23 | — |
| 0 | 35 | 53 | — | 13 | — | 8 | — |
| 8.75 | 35 | 97 | 81 | 77 | 57 | 43 | 30 |

TABLE 62

Synergistic Activity of Foliar-Applied Compound A Benzyl Ester and Aminopyralid Herbicidal Compositions on Weed Control in a Cereal Cropping System.

| Application Rate (gai/ha) | | POLCO | | CIRAR | | BRSNN | |
|---|---|---|---|---|---|---|---|
| Compound A Benzyl Ester | Aminopyralid | Ob | Ex | Ob | Ex | Ob | Ex |
| 8.75 | 0 | 50 | — | 70 | — | 23 | — |
| 0 | 3 | 3 | — | 13 | — | 0 | — |
| 8.75 | 3 | 67 | 52 | 82 | 74 | 40 | 23 |

TABLE 63

Synergistic Activity of Foliar-Applied Compound A Benzyl Ester and Clopyralid Herbicidal Compositions on Weed Control in a Cereal Cropping System.

| Application Rate (gai/ha) | | AMARE | |
|---|---|---|---|
| Compound A Benzyl Ester | Clopyralid | Ob | Ex |
| 8.75 | 0 | 60 | — |
| 0 | 50 | 17 | — |
| 8.75 | 50 | 73 | 67 |

TABLE 64

Synergistic Activity of Foliar-Applied Compound A Benzyl Ester and Picloram Herbicidal Compositions on Weed Control in a Cereal Cropping System.

| Application Rate (gai/ha) | | VIOTR | | STEME | | POLCO | |
|---|---|---|---|---|---|---|---|
| Compound A Benzyl Ester | Picloram | Ob | Ex | Ob | Ex | Ob | Ex |
| 8.75 | 0 | 30 | — | 70 | — | 50 | — |
| 0 | 10 | 3 | — | 0 | — | 40 | — |
| 8.75 | 10 | 43 | 32 | 80 | 70 | 78 | 70 |

TABLE 65

Synergistic Activity of Foliar-Applied Compound A Benzyl Ester and Fluroxypyr Herbicidal Compositions on Weed Control in a Cereal Cropping System.

| Application Rate (gai/ha) | | AMARE | | VIOTR | | POLCO | | CIRAR | |
|---|---|---|---|---|---|---|---|---|---|
| Compound A Benzyl Ester | Fluroxypyr | Ob | Ex | Ob | Ex | Ob | Ex | Ob | Ex |
| 8.75 | 0 | 60 | — | 30 | — | 50 | — | 70 | — |
| 0 | 35 | 33 | — | 10 | — | 23 | — | 3 | — |
| 8.75 | 35 | 83 | 73 | 60 | 37 | 78 | 62 | 78 | 71 |

TABLE 66

Synergistic Activity of Foliar-Applied Compound A Benzyl Ester and Quinclorac Herbicidal Compositions on Weed Control in a Cereal Cropping System.

| Application Rate (gai/ha) | | AMARE | | VIOTR | | POLCO | |
|---|---|---|---|---|---|---|---|
| Compound A Benzyl Ester | Quinclorac | Ob | Ex | Ob | Ex | Ob | Ex |
| 8.75 | 0 | 60 | — | 30 | — | 50 | — |
| 0 | 140 | 27 | — | 0 | — | 3 | — |
| 8.75 | 140 | 83 | 71 | 50 | 30 | 58 | 52 |

| | | |
|---|---|---|
| AMARE | *Amaranthus retroflexus* (L.) | pigweed, redroot |
| VIOTR | *Viola tricolor* (L.) | pansy, wild |
| CIRAR | *Cirsium arvense* (L.) Scop. | thistle, Canada |
| POLCO | *Polygonum convolvulus* | buckwheat, wild |
| BRSNN | *Brassica napus* (L.) | canola, volunteer |
| STEME | *Stellaria media* (L.) Vill. | chickweed, common | gae/ha = grams acid equivalent per hectare
gai/ha = grams active ingredient per hectare
Ob = observed value
Ex = expected value as calculated by Colby's equation
DAA = days after application

Example V

Evaluation of Postemergence Herbicidal Activity of Mixtures in Forage Crops

Seeds or root cuttings of the desired test plant species were planted in Sun Gro MetroMix® 306 planting mixture, which typically has a pH of 6.0 to 6.8 and an organic matter content of about 30 percent, in plastic pots with a surface area of 126.6 square centimeters (cm²). When required to ensure good germination and healthy plants, a fungicide treatment and/or other chemical or physical treatment was applied. The plants were grown for 14-60 days in a greenhouse with an approximate 14 hour photoperiod which was maintained at approximately 28° C. during the day and 24° C. during the night. Nutrients and water were added on a regular basis and supplemental lighting was provided with overhead metal halide 1000-Watt lamps as necessary. The plants were employed for testing when they reached the BBCH13 to BBCH23 leaf stage.

Treatments consisted of the benzyl ester of 4-amino-3-chloro-5-fluoro-6-(4-chloro-2-fluoro-3-methoxy-phenyl)pyridine-2-carboxylic acid (Compound A), formulated as a SC, and a second herbicide alone and in combination.

Forms of Compound A (Compound of Formula I) Tested Include:

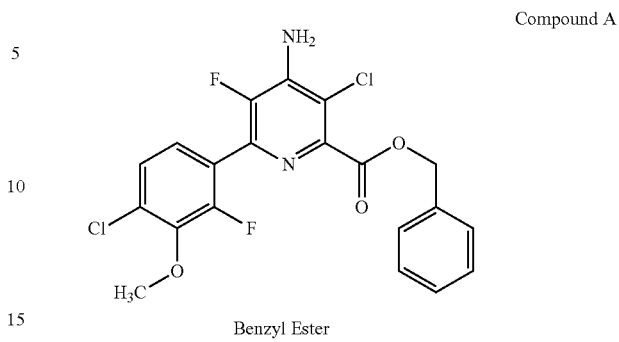

Compound A
Benzyl Ester

A measured aliquot of Compound A was placed in 25 milliliter (mL) glass vial and diluted in a volume of 1.25% (v/v) Agri-Dex® crop oil concentrated to obtain stock solutions. Compound requirements are based upon a 12 mL application volume at a rate of 187 liters per hectare (L/ha). Spray solutions of the second herbicide or experimental compound mixtures were prepared by adding the stock solutions to the appropriate amount of dilution solution to form 12 mL spray solution with active ingredients in two-way combinations. Formulated compounds were applied to the plant material with an overhead Mandel track sprayer equipped with 8002E nozzles calibrated to deliver 187 L/ha over an application area of 0.503 square meters (m²) at a spray height of 18 inches (46 cm) above average plant canopy. Control plants were sprayed in the same manner with the solvent blank.

The treated plants and control plants were placed in a greenhouse as described above and watered by sub-irrigation to prevent wash-off of the test compounds. After approximately 21 days, the condition of the test plants, as compared with that of the control plants, was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22).

The following equation was used to calculate the expected activity of mixtures containing two active ingredients, A and B:

Expected=$A+B-(A \times B/100)$

A=observed efficacy of active ingredient A at the same concentration as used in the mixture.

B=observed efficacy of active ingredient B at the same concentration as used in the mixture.

The compounds tested, application rates employed, plant species tested, and results are given in Tables 67-75.

TABLE 67

Synergistic Activity of Foliar-Applied Compound A Benzyl Ester and Triclopyr Butoxyethyl Ester (BEE; Garlon 4) Herbicidal Compositions on Weed Control in a Forage System

| Application Rate (gae/ha) | | CENMA | | SONAR | | CIRAR | | CASOB | |
|---|---|---|---|---|---|---|---|---|---|
| Compound A Benzyl Ester | Triclopyr BEE | Obs | Exp | Obs | Exp | Obs | Exp | Obs | Exp |
| 4.4 | 0 | 70 | — | 65 | — | 30 | — | 38 | — |
| 8.8 | 0 | 85 | — | 100 | — | 30 | — | — | — |
| 17.5 | 0 | 95 | — | 95 | — | — | — | — | — |
| 0 | 35 | 30 | — | 60 | — | — | — | — | — |

TABLE 67-continued

Synergistic Activity of Foliar-Applied Compound A Benzyl Ester and
Triclopyr Butoxyethyl Ester (BEE; Garlon 4) Herbicidal Compositions
on Weed Control in a Forage System

| Application Rate (gae/ha) | | CENMA | | SONAR | | CIRAR | | CASOB | |
|---|---|---|---|---|---|---|---|---|---|
| Compound A Benzyl Ester | Triclopyr BEE | Obs | Exp | Obs | Exp | Obs | Exp | Obs | Exp |
| 0 | 50 | — | — | — | — | — | — | 18 | — |
| 0 | 70 | 45 | — | 60 | — | 40 | — | — | — |
| 4.4 | 35 | 100 | 79 | 100 | 86 | — | — | — | — |
| 8.8 | 35 | 100 | 90 | 100 | 100 | — | — | — | — |
| 17.5 | 35 | 100 | 97 | 100 | 98 | — | — | — | — |
| 4.4 | 50 | — | — | — | — | — | — | 70 | 50 |
| 4.4 | 70 | 100 | 84 | 100 | 86 | 70 | 58 | — | — |
| 8.8 | 70 | 100 | 92 | 100 | 100 | 85 | 58 | — | — |
| 17.5 | 70 | 100 | 97 | 100 | 98 | — | — | — | — |

TABLE 68

Synergistic Activity of Foliar-Applied Compound A Benzyl Ester and Fluroxypyr
Meptyl Ester (ME; Starane) Herbicidal Compositions on Weed Control in a Forage System

| Application Rate (gae/ha) | | CENMA | | SONAR | | TRFRE | | CIRAR | | SOOSS | |
|---|---|---|---|---|---|---|---|---|---|---|---|
| Compound A Benzyl Ester | Fluroxypyr ME | Obs | Exp | Obs | Exp | Obs | Exp | Obs | Exp | Obs | Exp |
| 2.2 | 0 | — | — | — | — | — | — | 25 | — | 15 | — |
| 4.4 | 0 | 70 | — | 65 | — | 0 | — | 30 | — | 45 | — |
| 8.8 | 0 | 85 | — | 100 | — | 10 | — | 30 | — | 100 | — |
| 17.5 | 0 | 95 | — | 95 | — | 30 | — | — | — | — | — |
| 0 | 35 | 0 | — | 0 | — | 15 | — | — | — | — | — |
| 0 | 70 | 0 | — | 15 | — | 20 | — | 10 | — | 50 | — |
| 4.4 | 35 | 100 | 70 | 100 | 65 | 30 | 15 | — | — | — | — |
| 8.8 | 35 | 100 | 85 | 100 | 100 | 40 | 24 | — | — | — | — |
| 17.5 | 35 | 100 | 95 | 100 | 95 | 50 | 41 | — | — | — | — |
| 2.2 | 70 | — | — | — | — | — | — | 35 | 32 | 100 | 57 |
| 4.4 | 70 | 100 | 70 | 100 | 70 | 70 | 20 | 45 | 37 | 98 | 72 |
| 8.8 | 70 | 100 | 85 | 100 | 100 | 90 | 28 | 60 | 37 | 98 | 100 |
| 17.5 | 70 | 100 | 95 | 100 | 96 | 90 | 44 | — | — | — | — |

TABLE 69

Synergistic Activity of Foliar-Applied Compound A Benzyl Ester
and 2,4-D Dimethylamine Salt (DMA) Herbicidal Compositions
on Weed Control in a Forage System

| Application Rate (gae/ha) | | CENMA | | SINAR | | SONAR | |
|---|---|---|---|---|---|---|---|
| Compound A Benzyl Ester | 2,4-D DMA Salt | Obs | Exp | Obs | Exp | Obs | Exp |
| 4.4 | 0 | 70 | — | 80 | — | 65 | — |
| 8.8 | 0 | 85 | — | 100 | — | 100 | — |
| 17.5 | 0 | 95 | — | 100 | — | 95 | — |
| 0 | 35 | 30 | — | 35 | — | 20 | — |
| 0 | 70 | 50 | — | 80 | — | 85 | — |
| 4.4 | 35 | 100 | 79 | 100 | 87 | 95 | 72 |
| 8.8 | 35 | 100 | 90 | 100 | 100 | 100 | 100 |
| 17.5 | 35 | 100 | 97 | 100 | 100 | 100 | 96 |
| 4.4 | 70 | 100 | 85 | 100 | 96 | 95 | 95 |
| 8.8 | 70 | 100 | 93 | 100 | 100 | 100 | 100 |
| 17.5 | 70 | 100 | 98 | 100 | 100 | 100 | 99 |

TABLE 70

Synergistic Activity of Foliar-Applied Compound A Benzyl Ester
and 2,4-D Choline Salt Herbicidal Compositions
on Weed Control in a Forage System

| Application Rate (gae/ha) | | CASOB | |
|---|---|---|---|
| Compound A Benzyl Ester | 2,4-D Choline Salt | Obs | Exp |
| 1.1 | 0 | 28 | — |
| 2.2 | 0 | 33 | — |
| 4.4 | 0 | 38 | — |
| 0 | 50 | 3 | — |
| 1.1 | 50 | 27 | 31 |
| 2.2 | 50 | 45 | 36 |
| 4.4 | 50 | 55 | 40 |

TABLE 71

Synergistic Activity of Foliar-Applied Compound A Benzyl Ester and Picloram Potassium Salt (K+ salt; Tordon 22K) Herbicidal Compositions on Weed Control in a Forage System

| Application Rate (gae/ha) | | CENMA | | SINAR | |
|---|---|---|---|---|---|
| Compound A Benzyl Ester | Picloram K+ Salt | Obs | Exp | Obs | Exp |
| 4.4 | 0 | 70 | — | 80 | — |
| 8.8 | 0 | 85 | — | 100 | — |
| 17.5 | 0 | 95 | — | 100 | — |
| 0 | 35 | 20 | — | 30 | — |
| 0 | 70 | 50 | — | 70 | — |
| 4.4 | 35 | 100 | 76 | 100 | 86 |
| 8.8 | 35 | 100 | 88 | 100 | 100 |
| 17.5 | 35 | 100 | 96 | 100 | 100 |
| 4.4 | 70 | 100 | 85 | 98 | 94 |
| 8.8 | 70 | 100 | 93 | 100 | 100 |
| 17.5 | 70 | 100 | 98 | 100 | 100 |

TABLE 72

Synergistic Activity of Foliar-Applied Compound A Benzyl Ester and Clopyralid Monoethanolamine Salt (MEA salt; Lontrel) Herbicidal Compositions on Weed Control in a Forage System

| Application Rate (gae/ha) | | CIRAR | | SOOSS | |
|---|---|---|---|---|---|
| Compound A Benzyl Ester | Clopyralid MEA Salt | Obs | Exp | Obs | Exp |
| 2.2 | 0 | 25 | — | 15 | — |
| 4.4 | 0 | 30 | — | 45 | — |
| 8.8 | 0 | 30 | — | 100 | — |
| 0 | 35 | 75 | — | 25 | — |
| 2.2 | 35 | 90 | 81 | 75 | 36 |
| 4.4 | 35 | 90 | 82 | 95 | 59 |
| 8.8 | 35 | 95 | 82 | 95 | 100 |

TABLE 73

Synergistic Activity of Foliar-Applied Compound A Benzyl Ester and Aminopyralid Triisopropanolammonium Salt (TIPA salt; milestone) Herbicidal Compositions on Weed Control in a Forage System

| Application Rate (gae/ha) | | TRFRE | | SINAR | | SOOSS | | CIRAR | |
|---|---|---|---|---|---|---|---|---|---|
| Compound A Benzyl Ester | Aminopyralid TIPA Salt | Obs | Exp | Obs | Exp | Obs | Exp | Obs | Exp |
| 4.4 | 0 | 0 | — | 80 | — | 15 | — | 25 | — |
| 8.8 | 0 | 10 | — | 100 | — | 45 | — | 30 | — |
| 17.5 | 0 | 30 | — | 100 | — | 100 | — | 30 | — |
| 0 | 17.5 | 35 | — | 25 | — | 45 | — | 45 | — |
| 0 | 35 | — | — | 45 | — | — | — | — | — |
| 4.4 | 17.5 | 45 | 35 | 95 | 85 | 90 | 53 | 90 | 89 |
| 8.8 | 17.5 | 45 | 42 | 98 | 100 | 90 | 70 | 98 | 90 |
| 17.5 | 17.5 | 65 | 55 | 100 | 100 | 95 | 100 | 98 | 90 |
| 4.4 | 35 | — | — | 100 | 89 | — | — | — | — |
| 8.8 | 35 | — | — | 100 | 100 | — | — | — | — |
| 17.5 | 35 | — | — | 100 | 100 | — | — | — | — |

TABLE 74

Synergistic Activity of Foliar-Applied Compound A Benzyl Ester and Dicamba Dimethylamine Salt (DMA Salt; Banvel) Herbicidal Compositions on Weed Control in a Forage System

| Application Rate (gae/ha) | | SIDSP | | SINAR | | CASOB | |
|---|---|---|---|---|---|---|---|
| Compound A Benzyl Ester | Dicamba DMA Salt | Obs | Exp | Obs | Exp | Obs | Exp |
| 1.1 | 0 | 72 | — | 72 | — | 28 | — |
| 2.2 | 0 | 77 | — | 98 | — | 33 | — |
| 4.4 | 0 | 85 | — | 100 | — | 38 | — |
| 0 | 50 | 25 | — | 65 | — | 20 | — |
| 1.1 | 50 | 87 | 79 | 100 | 90 | 32 | 43 |
| 2.2 | 50 | 93 | 83 | 100 | 100 | 52 | 47 |
| 4.4 | 50 | 97 | 89 | 100 | 100 | 67 | 51 |

TABLE 75

Synergistic Activity of Foliar-Applied Compound A Benzyl Ester and Aminocyclopyrachlor Herbicidal Compositions on Weed Control in a Forage System

| Application Rate (gae/ha) | | TRFRE | | SINAR | | CENMA | |
|---|---|---|---|---|---|---|---|
| Compound A Benzyl Ester | Amino-cyclopyrachlor | Obs | Exp | Obs | Exp | Obs | Exp |
| 4.4 | 0 | 0 | — | 80 | — | 70 | — |
| 8.8 | 0 | 10 | — | 100 | — | 85 | — |
| 17.5 | 0 | 30 | — | 100 | — | 95 | — |
| 0 | 8.75 | 45 | — | 25 | — | 55 | — |
| 0 | 17.5 | 55 | — | 45 | — | 60 | — |
| 4.4 | 8.75 | 55 | 45 | 95 | 85 | 100 | 87 |
| 8.8 | 8.75 | 60 | 51 | 98 | 100 | 100 | 93 |
| 17.5 | 8.75 | 65 | 62 | 100 | 100 | 100 | 98 |
| 4.4 | 17.5 | 65 | 55 | 100 | 89 | 100 | 88 |
| 8.8 | 17.5 | 70 | 60 | 100 | 100 | 100 | 94 |
| 17.5 | 17.5 | 75 | 69 | 100 | 100 | 100 | 98 |

| | | |
|---|---|---|
| CASOB | *Cassia obtusifolia* L. | sicklepod |
| CENMA | *Centaurea maculosa* LAM. | knapweed, spotted |
| CIRAR | *Cirsium arvense* (L.) SCOP. | thistle, Canada |
| SIDSP | *Sida spinosa* L. | sida, prickly |
| SINAR | *Sinapis arvensis* L. | mustard, wild |
| SONAR | *Sonchus arvensis* L. | sowthistle, field |
| SOOSS | *Solidago* L. spec. | goldenrod |
| TRFRE | *Trifolium repens* L. | clover, Dutch | gae/ha = grams acid equivalent per hectare
gai/ha = grams active ingredient per hectare
Obs = observed value
Exp = expected value as calculated by Colby's equation
DAA = days after application

What is claimed is:

1. A herbicidal composition comprising a herbicidally effective amount of (a) a compound of the formula (I):

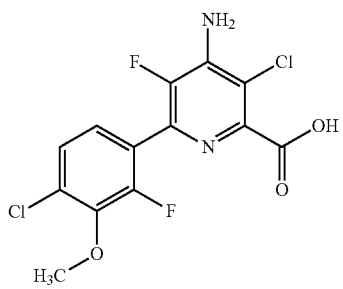

(I)

or an agriculturally acceptable salt or alkyl ester or benzyl ester thereof and (b) a synthetic auxin herbicide; wherein the (a) and (b) are present in the composition in a ratio such that the composition exhibits synergy.

2. The composition of claim 1, wherein (b) the synthetic auxin herbicide is at least one compound selected from the group consisting of: 2,4-D, 2,4-D EHE, 2,4-DMA, 2,4-D choline, aminocyclopyrachlor, aminopyralid, aminopyralid TIPA, clomeprop-P, clopyralid, clopyralid MEA, dicamba, dicamba DMA, diclorprop-P, fluoroxypyr, fluoroxypyr MHE, MCPA, MCPA EHE, mecoprop-P, picloram, picloram $K^+$ salt, quinclorac, triclopyr, triclopyr TEA, triclopyr choline, triclopyr BEE, halauxifen-methyl, halauxifen-methyl (methyl 4-amino-3-chloro-6-(4-chloro-2-fluoro-3-methoxyphenyl)picolinate) or its carboxylate potassium salt, or an agriculturally acceptable salt, ester, or carboxylate salt thereof of at least one of the aforementioned synthetic auxin herbicide.

3. The composition of claim 1, wherein the synthetic auxin herbicide is 2,4-D, 2,4-D EHE, 2,4-DMA, or 2,4-D choline wherein the weight ratio of the compound of formula (I) to 2,4-D, 2,4-D EHE, 2,4-DMA, or 2,4-D choline given in units of gae/ha to gai/ha is from about 1:2 to about 1:110.

4. The composition of claim 1, wherein the synthetic auxin herbicide is aminocyclopyrachlor wherein the weight ratio of the compound of formula (I) to aminocyclopyrachlor given in units of gae/ha to gai/ha is from about 1:1 to about 1:4.

5. The composition of claim 1, wherein the synthetic auxin herbicide is aminopyralid or aminopyralid TIPA wherein the weight ratio of the compound of formula (I) to aminopyralid or aminopyralid TIPA given in units of gae/ha to gai/ha is from about 1:1 to about 1:8.

6. The composition of claim 1, wherein the synthetic auxin herbicide is clomeprop-P having a weight ratio of the compound of formula (I) or salt or ester thereof to clomeprop-P or salt or ester thereof is within the range of from about 1:200 to about 1:1.

7. The composition of claim 1, wherein the synthetic auxin herbicide is clopyralid or clopyralid MEA wherein the weight ratio of the compound of formula (I) to clopyralid or clopyralid MEA given in units of gae/ha to gai/ha is from 1:4 to 1:16.

8. The composition of claim 1, wherein the synthetic auxin herbicide is dicamba or dicamba DMA wherein the weight ratio of the compound of formula (I) to dicamba or dicamba DMA given in units of gae/ha to gai/ha is from 1:3.3 to 1:64.

9. The composition of claim 1, wherein the synthetic auxin herbicide is diclorprop-P wherein the weight ratio of the compound of formula (I) to diclorprop-P given in units of gae/ha to gai/ha is about 1:16.

10. The composition of claim 1, wherein the synthetic auxin herbicide is fluoroxypyr or fluoroxypyr MHE wherein the weight ratio of the compound of formula (I) to fluoroxypyr or fluoroxypyr MHE given in units of gae/ha to gai/ha is from 1:2 to 1:35.

11. The composition of claim 1, wherein the synthetic auxin herbicide is MCPA or MCPA EHE wherein the weight ratio of the compound of formula (I) to MCPA or MCPA EHE given in units of gae/ha to gai/ha is from 1:2 to 1:35.

12. The composition of claim 1, wherein the synthetic auxin herbicide is mecoprop-P wherein the weight ratio of the compound of formula (I) to mecoprop-P given in units of gae/ha to gai/ha is about 1:23.

13. The composition of claim 1, wherein the synthetic auxin herbicide is picloram or picloram $K^+$ salt wherein the weight ratio of the compound of formula (I) to picloram or picloram $K^+$ salt given in units of gae/ha to gai/ha is from 1:1.1 to 1:16.

14. The composition of claim 1, wherein the synthetic auxin herbicide is quinclorac wherein the weight ratio of the compound of formula (I) to quinclorac given in units of gae/ha to gai/ha is from 1:1.7 to 1:16.

15. The composition of claim 1, wherein the synthetic auxin herbicide is triclopyr, triclopyr TEA, triclopyr choline or triclopyr BEE wherein the weight ratio of the compound of formula (I) to triclopyr, triclopyr TEA, triclopyr choline or triclopyr BEE given in units of gae/ha to gai/ha is from 1:7 to 1:45.

16. The composition of claim 1, wherein the synthetic auxin herbicide is halauxifen-methyl(methyl 4-amino-3-chloro-6-(4-chloro-2-fluoro-3-methoxyphenyl)picolinate) or its carboxylate potassium salt wherein the weight ratio of the compound of formula (I) to halauxifen-methyl(methyl 4-amino-3-chloro-6-(4-chloro-2-fluoro-3-methoxyphenyl) picolinate) or its carboxylate potassium salt given in units of gae/ha to gai/ha is from 1:4 to 10:1.

17. The composition of claim 1, further comprising an agriculaturally acceptable adjuvant, carrier, or safener.

18. A method of controlling undesirable vegetation which comprises contacting the vegetation or the locus thereof with or applying to the soil or water to prevent the emergence or growth of vegetation, a herbicidally effective amount of cobination comprising (a) a compound of the formula (I)

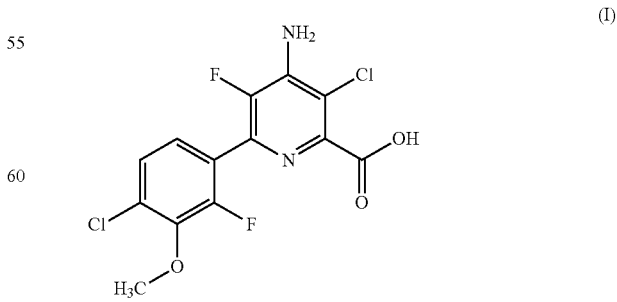

(I)

or an agriculturally acceptable salt or alkyl ester or benzyl ester thereof and (b) a synthetic auxin herbicide; wherein the (a) and (b) are present in the combination in a ratio such that the combination exhibits synergy, and wherein the undesirable vegetation is controlled in direct-seeded, water-seeded and transplanted rice, cereals, wheat, barley, oats, rye, sorghum, maize or canola crop.

19. The method of claim 18, wherein the undesirable vegetation is immature.

20. The method of claim 18, wherein the water is part of a flooded rice paddy.

21. The method of claim 18 wherein a herbicidally effective amount of (a) is applied either pre- or post-emergently to at least one of the following: the crop, a fieled, or a paddy.

22. The method of claim 18, wherein the undesirable vegetation is controlled in glyphosate-, 5-enolpyruvylshikimate-3-phosphate synthase inhibitor-, glufosinate-, glutamine synthetase inhibitor-, dicamba-, phenoxy auxin-, pyridyloxy auxin-, synthetic auxin-, auxin transport inhibitor-, aryloxyphenoxypropionate-, cyclohexanedione-, phenylpyrazoline-, acetyl CoA carboxylase inhibitor-, imidazolinone-, sulfonylurea-, pyrimidinylthiobenzoate-, triazolopyrimidine-, sulfonylaminocarbonyltriazolinone-, acetolactate synthase or acetohydroxy acid synthase inhibitor-, 4-hydroxyphenyl-pyruvate dioxygenase inhibitor-, phytoene desaturase inhibitor-, carotenoid biosynthesis inhibitor-, protoporphyrinogen oxidase inhibitor-, cellulose biosynthesis inhibitor-, mitosis inhibitor-, microtubule inhibitor-, very long chain fatty acid inhibitor-, fatty acid and lipid biosynthesis inhibitor-, photosystem I inhibitor-, photosystem II inhibitor-, triazine-, or bromoxynil-tolerant crops.

23. The method of claim 22, wherein the tolerant crop possesses multiple or stacked traits conferring tolerance to multiple herbicides.

24. The method of claim 22, wherein the undesirable vegetation comprises a herbicide resistant or tolerant plant.

25. The method of claim 22 wherein the resistant or tolerant plant is resistant or tolerant to multiple herbicides.

26. The method of claim 25, wherein the resistant or tolerant plant is resistant or tolerant to acetolactate synthase or acetohydroxy acid synthase inhibitors, photosystem II inhibitors, acetyl CoA carboxylase inhibitors, synthetic auxins, auxin transport inhibitors, photosystem I inhibitors, 5-enolpyruvylshikimate-3-phosphate synthase inhibitors, microtubule assembly inhibitors, fatty acid and lipid biosynthesis inhibitors, protoporphyrinogen oxidase inhibitors, carotenoid biosynthesis inhibitors, very long chain fatty acid inhibitors, phytoene desaturase inhibitors, glutamine synthetase inhibitors, 4-hydroxyphenyl-pyruvate-dioxygenase inhibitors, mitosis inhibitors, cellulose biosynthesis inhibitors, herbicides with multiple modes-of-action, quinclorac, arylaminopropionic acids, difenzoquat, endothall, or organoarsenicals.

* * * * *

UNITED STATES PATENT AND TRADEMARK OFFICE
CERTIFICATE OF CORRECTION

| | | |
|---|---|---|
| PATENT NO. | : 8,912,120 B2 | Page 1 of 1 |
| APPLICATION NO. | : 13/833923 | |
| DATED | : December 16, 2014 | |
| INVENTOR(S) | : Carla N. Yerkes et al. | |

It is certified that error appears in the above-identified patent and that said Letters Patent is hereby corrected as shown below:

In the claims,

Please amend the first paragraph of Claim 18, Column 94, line 49 as follows:

18. A method of controlling undesirable vegetation which comprises contacting the vegetation or the locus thereof with, or applying to the soil or water to prevent the emergence or growth of vegetation, a herbicidally effective amount of combination comprising (a) a compound of the formula (I):

Please amend Claim 21, Column 95, line 12 as follows:

a [fieled] field

Signed and Sealed this
Twenty-eighth Day of April, 2015

Michelle K. Lee
*Director of the United States Patent and Trademark Office*